(12) United States Patent
Roberts et al.

(10) Patent No.: US 12,252,513 B2
(45) Date of Patent: Mar. 18, 2025

(54) THERMOSTABLE PHYCOBILIPROTEINS PRODUCED FROM RECOMBINANT ARTHROSPIRA

(71) Applicant: LUMEN BIOSCIENCE, INC., Seattle, WA (US)

(72) Inventors: James Roberts, Seattle, WA (US); Ryo Takeuchi, Seattle, WA (US); Nhi Khuong, Kenmore, WA (US); Barry L Stoddard, Bellevue, WA (US); Rolf Kuestner, Seattle, WA (US)

(73) Assignee: Lumen Bioscience, Inc., Seattle, WA (US)

( * ) Notice: Subject to any disclaimer, the term of this patent is extended or adjusted under 35 U.S.C. 154(b) by 52 days.

(21) Appl. No.: 17/260,693

(22) PCT Filed: Jul. 16, 2019

(86) PCT No.: PCT/US2019/042072
§ 371 (c)(1),
(2) Date: Jan. 15, 2021

(87) PCT Pub. No.: WO2020/018586
PCT Pub. Date: Jan. 23, 2020

(65) Prior Publication Data
US 2022/0135627 A1    May 5, 2022

Related U.S. Application Data

(60) Provisional application No. 62/698,712, filed on Jul. 16, 2018.

(51) Int. Cl.
*C07K 14/195* (2006.01)
*C12N 1/20* (2006.01)

(52) U.S. Cl.
CPC .............. *C07K 14/195* (2013.01); *C12N 1/20* (2013.01)

(58) Field of Classification Search
CPC ................................. C07K 14/195; C12N 1/20
See application file for complete search history.

(56) References Cited

U.S. PATENT DOCUMENTS 4,751,180 A    6/1988  Cousens et al.
4,873,192 A    10/1989 Kunkel
(Continued)

FOREIGN PATENT DOCUMENTS

CN    1177002 A    3/1998
CN    1528902 A    9/2004
(Continued)

OTHER PUBLICATIONS

Adir et al. "Structure of c-Phycocyanin from the Thermophilic Cyanobacterium Synechococcus vulcanus at 2.5 A: Structural Implications for Thermal Stability in Phycobilisome Assembly", 2001, vol. 313, p. 71-81. (Year: 2001).*
(Continued)

*Primary Examiner* — Gary B Nickol
*Assistant Examiner* — Amelia Nicole Dickens
(74) *Attorney, Agent, or Firm* — COOLEY LLP

(57) ABSTRACT

Provided herein are novel thermostable phycobiliproteins. These proteins may be stabilized by the introduction of disulfide bonds which stabilize the protein. Modified cells expressing these thermostable phycobiliproteins and methods of making them are also provided.

18 Claims, 18 Drawing Sheets

Specification includes a Sequence Listing.

(56) References Cited

U.S. PATENT DOCUMENTS

| | | |
|---|---|---|
| 4,935,233 A | 6/1990 | Bell et al. |
| 5,429,939 A | 7/1995 | Misawa et al. |
| 5,589,581 A | 12/1996 | Misawa et al. |
| 5,661,017 A | 8/1997 | Dunahay et al. |
| 5,684,238 A | 11/1997 | Ausich et al. |
| 5,811,273 A | 9/1998 | Misawa et al. |
| 5,910,433 A | 6/1999 | Kajiwara et al. |
| 5,972,690 A | 10/1999 | Misawa et al. |
| 6,087,152 A | 7/2000 | Hohmann et al. |
| 6,124,113 A | 9/2000 | Hohmann et al. |
| 6,150,130 A | 11/2000 | Misawa et al. |
| 6,207,409 B1 | 3/2001 | Hohmann et al. |
| 6,214,575 B1 | 4/2001 | Yano et al. |
| 6,291,204 B1 | 9/2001 | Pasamontes et al. |
| 6,306,639 B1 | 10/2001 | Woods et al. |
| 6,528,314 B1 | 3/2003 | Le Mouellic et al. |
| 6,677,134 B2 | 1/2004 | Pasamontes et al. |
| 6,929,928 B2 | 8/2005 | Cheng et al. |
| 6,969,595 B2 | 11/2005 | Brzostowicz et al. |
| 6,989,472 B1 | 1/2006 | Carol et al. |
| 7,063,957 B2 | 6/2006 | Chen |
| 7,064,196 B2 | 6/2006 | Cheng et al. |
| 7,070,952 B2 | 7/2006 | Cheng et al. |
| 7,074,604 B1 | 7/2006 | Tang et al. |
| 7,091,031 B2 | 8/2006 | Cheng et al. |
| 7,118,896 B2 | 10/2006 | Kalscheuer et al. |
| 7,157,619 B1 | 1/2007 | Lassner et al. |
| 7,176,000 B2 | 2/2007 | Glazer et al. |
| 7,217,537 B2 | 5/2007 | Miller, Jr. et al. |
| 7,223,909 B2 | 5/2007 | Hauptmann et al. |
| 7,232,665 B2 | 6/2007 | Cheng et al. |
| 7,232,666 B2 | 6/2007 | Sharpe et al. |
| 7,252,964 B2 | 8/2007 | Giraud et al. |
| 7,252,985 B2 | 8/2007 | Cheng et al. |
| 7,288,387 B2 | 10/2007 | Cheng et al. |
| 7,291,482 B2 | 11/2007 | Cheng et al. |
| 7,385,123 B2 | 6/2008 | Sauer et al. |
| 7,393,671 B2 | 7/2008 | Cheng et al. |
| 7,422,873 B2 | 9/2008 | Stead et al. |
| 7,425,625 B2 | 9/2008 | Tang et al. |
| 7,427,593 B1 | 9/2008 | Dahlqvist et al. |
| 7,498,026 B2 | 3/2009 | Dahlqvist et al. |
| 7,504,236 B2 | 3/2009 | Miller, Jr. et al. |
| 7,522,162 B2 | 4/2009 | Cubicciotti |
| 7,695,931 B2 | 4/2010 | Nishida et al. |
| 7,695,932 B2 | 4/2010 | Stephanopoulos et al. |
| 7,741,070 B2 | 6/2010 | Stephanopoulos et al. |
| 7,794,696 B2 | 9/2010 | Van et al. |
| 7,794,969 B1 | 9/2010 | Reppas et al. |
| 7,999,151 B2 | 8/2011 | Choi et al. |
| 8,030,022 B2 | 10/2011 | Tanaka et al. |
| 8,110,670 B2 | 2/2012 | Hu et al. |
| 8,394,614 B2 | 3/2013 | Roberts et al. |
| 8,394,621 B2 | 3/2013 | Roberts et al. |
| 8,569,014 B2 | 10/2013 | Tanaka et al. |
| 8,835,137 B2 | 9/2014 | Roberts et al. |
| 9,029,120 B2 | 5/2015 | Roberts et al. |
| 9,040,264 B2 | 5/2015 | Kristof et al. |
| 9,523,096 B2 | 12/2016 | Roberts et al. |
| 9,914,907 B2 | 3/2018 | Roberts et al. |
| 10,131,870 B2 | 11/2018 | Takeuchi et al. |
| 10,336,982 B2 | 7/2019 | Takeuchi et al. |
| 10,415,012 B2 | 9/2019 | Takeuchi et al. |
| 10,415,013 B2 | 9/2019 | Takeuchi et al. |
| 10,563,168 B2 | 2/2020 | Roberts et al. |
| 10,654,901 B2 | 5/2020 | Roberts et al. |
| 10,760,045 B2 | 9/2020 | Roberts et al. |
| 10,787,488 B2 | 9/2020 | Roberts et al. |
| 11,174,294 B2 | 11/2021 | Roberts et al. |
| 11,279,912 B2 | 3/2022 | Roberts et al. |
| 2003/0003528 A1 | 1/2003 | Brzostowicz et al. |
| 2003/0104379 A1 | 6/2003 | Lagarias et al. |
| 2003/0148319 A1 | 8/2003 | Brzostowicz et al. |
| 2003/0233675 A1 | 12/2003 | Cao et al. |
| 2004/0077068 A1 | 4/2004 | Brzostowicz et al. |
| 2004/0078846 A1 | 4/2004 | Desouza et al. |
| 2004/0219629 A1 | 11/2004 | Cheng et al. |
| 2004/0224383 A1 | 11/2004 | Cheng et al. |
| 2005/0003474 A1 | 1/2005 | Desouza et al. |
| 2005/0260699 A1 | 11/2005 | Desouza et al. |
| 2005/0281839 A1 | 12/2005 | Belay et al. |
| 2006/0053513 A1 | 3/2006 | Steiger et al. |
| 2006/0059584 A1 | 3/2006 | Klebsattel et al. |
| 2006/0088550 A1 | 4/2006 | Bachmann et al. |
| 2006/0099670 A1 | 5/2006 | Matuschek et al. |
| 2006/0121468 A1 | 6/2006 | Allnutt et al. |
| 2006/0121557 A1 | 6/2006 | Hoshino et al. |
| 2006/0137043 A1 | 6/2006 | Puzio et al. |
| 2006/0185038 A1 | 8/2006 | De Block |
| 2006/0234333 A1 | 10/2006 | Matuschek et al. |
| 2007/0059790 A1 | 3/2007 | Miller et al. |
| 2007/0065900 A1 | 3/2007 | Dicosimo et al. |
| 2007/0065901 A1 | 3/2007 | Dicosimo et al. |
| 2007/0065902 A1 | 3/2007 | Dicosimo et al. |
| 2007/0065903 A1 | 3/2007 | Dicosimo et al. |
| 2007/0269859 A1 | 11/2007 | Lassner et al. |
| 2008/0107652 A1 | 5/2008 | Durvasula et al. |
| 2008/0124755 A1 | 5/2008 | Louie et al. |
| 2008/0160592 A1 | 7/2008 | Dahlqvist et al. |
| 2008/0193970 A1 | 8/2008 | Fardoux et al. |
| 2008/0301839 A1 | 12/2008 | Ravanello |
| 2009/0035832 A1 | 2/2009 | Koshland, Jr. |
| 2009/0142322 A1 | 6/2009 | Ye |
| 2009/0155864 A1 | 6/2009 | Bauer et al. |
| 2009/0175911 A1 | 7/2009 | Cutting et al. |
| 2009/0197321 A1 | 8/2009 | Chiou et al. |
| 2009/0203070 A1 | 8/2009 | Devroe et al. |
| 2009/0215179 A1 | 8/2009 | Gressel et al. |
| 2009/0220537 A1 | 9/2009 | Tindle et al. |
| 2009/0226582 A1 | 9/2009 | Ide et al. |
| 2009/0298143 A1 | 12/2009 | Roessler et al. |
| 2010/0068776 A1 | 3/2010 | Woods et al. |
| 2010/0081178 A1 | 4/2010 | Roberts et al. |
| 2010/0184169 A1 | 7/2010 | Roberts et al. |
| 2010/0251601 A1 | 10/2010 | Hu et al. |
| 2010/0255551 A1 | 10/2010 | Roberts et al. |
| 2011/0053216 A1 | 3/2011 | Vermaas |
| 2011/0072714 A1 | 3/2011 | Gaertner |
| 2011/0129474 A1 | 6/2011 | Shoemaker et al. |
| 2011/0184152 A1 | 7/2011 | Adams et al. |
| 2011/0244532 A1 | 10/2011 | Hu et al. |
| 2011/0250659 A1 | 10/2011 | Roberts et al. |
| 2011/0250663 A1 | 10/2011 | Schirmer et al. |
| 2011/0252501 A1 | 10/2011 | Abad et al. |
| 2011/0277190 A1 | 11/2011 | Abad |
| 2012/0115208 A1 | 5/2012 | Ellison et al. |
| 2012/0142082 A1 | 6/2012 | Sharpe et al. |
| 2012/0252080 A1 | 10/2012 | Kristof et al. |
| 2013/0039889 A1 | 2/2013 | McDonagh et al. |
| 2013/0058962 A1 | 3/2013 | Shoemaker et al. |
| 2013/0078686 A1 | 3/2013 | Holtzapple et al. |
| 2013/0143284 A1 | 6/2013 | Roberts et al. |
| 2013/0171677 A1* | 7/2013 | Bryant ............... C12N 9/88 435/254.2 |
| 2013/0224811 A1 | 8/2013 | Holtzapple et al. |
| 2013/0230537 A1* | 9/2013 | Hussack ......... G01N 33/56911 435/7.1 |
| 2013/0344549 A1 | 12/2013 | Roberts et al. |
| 2014/0004580 A1 | 1/2014 | Roberts et al. |
| 2014/0011264 A1 | 1/2014 | Duhring et al. |
| 2014/0030785 A1 | 1/2014 | Kallas et al. |
| 2014/0325710 A1 | 10/2014 | Abad et al. |
| 2014/0356867 A1 | 12/2014 | Peter et al. |
| 2015/0024442 A1 | 1/2015 | Roberts et al. |
| 2015/0329868 A1 | 11/2015 | Hickman et al. |
| 2016/0046902 A1 | 2/2016 | Roberts et al. |
| 2017/0240872 A1 | 8/2017 | Guo et al. |
| 2017/0240944 A1 | 8/2017 | Heinnickel et al. |
| 2017/0298319 A1 | 10/2017 | Takeuchi et al. |
| 2018/0051057 A1 | 2/2018 | Roberts et al. |
| 2018/0134755 A1 | 5/2018 | Roberts et al. |
| 2018/0222945 A1 | 8/2018 | Roberts et al. |
| 2018/0305660 A1 | 10/2018 | Takeuchi et al. |
| 2018/0312801 A1 | 11/2018 | Takeuchi et al. |

(56) References Cited

U.S. PATENT DOCUMENTS

| | | |
|---|---|---|
| 2019/0002820 A1 | 1/2019 | Takeuchi et al. |
| 2019/0062763 A1 | 2/2019 | Roberts et al. |
| 2019/0093066 A1 | 3/2019 | Roberts et al. |
| 2020/0017822 A1 | 1/2020 | Takeuchi et al. |
| 2020/0172859 A1 | 6/2020 | Roberts et al. |
| 2020/0392189 A1 | 12/2020 | Roberts et al. |
| 2021/0047610 A1 | 2/2021 | Roberts et al. |
| 2021/0213124 A1 | 7/2021 | Roberts et al. |
| 2021/0338751 A1 | 11/2021 | Roberts et al. |
| 2024/0002481 A1 | 1/2024 | Roberts |
| 2024/0150440 A1 | 5/2024 | Roberts et al. |

FOREIGN PATENT DOCUMENTS

| | | |
|---|---|---|
| CN | 1608132 A | 4/2005 |
| CN | 1843150 A | 10/2006 |
| CN | 101173214 A | 5/2008 |
| CN | 103382482 A | 11/2013 |
| CN | 103820459 A | 5/2014 |
| CN | 104311649 A | 1/2015 |
| CN | 104479010 A | 4/2015 |
| CN | 108495685 A | 9/2018 |
| CN | 112094342 A | 12/2020 |
| EP | 0393690 A1 | 10/1990 |
| EP | 0872554 A2 | 10/1998 |
| EP | 1854889 A1 | 11/2007 |
| JP | H06253863 A | 9/1994 |
| JP | H1156360 A | 3/1999 |
| JP | 200424232 | 1/2004 |
| JP | 2006075097 A | 3/2006 |
| JP | 2006191919 A | 7/2006 |
| JP | 2006520254 A | 9/2006 |
| JP | 3874897 B2 | 1/2007 |
| JP | 2011512841 A | 4/2011 |
| JP | 2015535224 A | 12/2015 |
| JP | 2017526372 A | 9/2017 |
| JP | 6253863 B1 | 12/2017 |
| KR | 100788479 B1 | 12/2007 |
| KR | 100845582 B1 | 7/2008 |
| KR | 20090046376 A | 5/2009 |
| KR | 20100051306 A | 5/2010 |
| TW | 200811098 A | 3/2008 |
| WO | WO-9839457 A1 | 9/1998 |
| WO | WO-9963055 A1 | 12/1999 |
| WO | WO-0241833 A2 | 5/2002 |
| WO | WO-02097137 A1 | 12/2002 |
| WO | WO-2004029234 A1 | 4/2004 |
| WO | WO-2004087892 A1 | 10/2004 |
| WO | WO-2006078050 A2 | 7/2006 |
| WO | WO-2006096392 A2 | 9/2006 |
| WO | WO-2007136762 A2 | 11/2007 |
| WO | WO-2008119082 A2 | 10/2008 |
| WO | WO-2008130437 A2 | 10/2008 |
| WO | WO-2009009391 A2 | 1/2009 |
| WO | WO-2009010826 A2 | 1/2009 |
| WO | WO-2009036095 A1 | 3/2009 |
| WO | WO-2009042950 A1 | 4/2009 |
| WO | WO-2009062190 A2 | 5/2009 |
| WO | WO-2009076559 A1 | 6/2009 |
| WO | WO-2009089185 A1 | 7/2009 |
| WO | WO-2009098089 A2 | 8/2009 |
| WO | WO-2009111513 A1 | 9/2009 |
| WO | WO-2009140696 A2 | 11/2009 |
| WO | WO-2010006312 A2 | 1/2010 |
| WO | WO-2010017245 A1 | 2/2010 |
| WO | WO-2010019813 A2 | 2/2010 |
| WO | WO-2010021711 A1 | 2/2010 |
| WO | WO-2010022090 A1 | 2/2010 |
| WO | WO-2010027516 A2 | 3/2010 |
| WO | WO-2010033921 A2 | 3/2010 |
| WO | WO-2010036951 A2 | 4/2010 |
| WO | WO-2010042664 A2 | 4/2010 |
| WO | WO-2010044960 A1 | 4/2010 |
| WO | WO-2010048568 A1 | 4/2010 |
| WO | WO-2010062480 A2 | 6/2010 |
| WO | WO-2010062707 A1 | 6/2010 |
| WO | WO-2010075440 A1 | 7/2010 |
| WO | WO-2010075483 A2 | 7/2010 |
| WO | WO-2010078584 A1 | 7/2010 |
| WO | WO-2010104763 A1 | 9/2010 |
| WO | WO-2010118410 A1 | 10/2010 |
| WO | WO-2010126891 A1 | 11/2010 |
| WO | WO-2010130725 A1 | 11/2010 |
| WO | WO-2011008535 A1 | 1/2011 |
| WO | WO-2011008565 A1 | 1/2011 |
| WO | WO-2011011568 A2 | 1/2011 |
| WO | WO-2011018116 A1 | 2/2011 |
| WO | WO-2011029013 A2 | 3/2011 |
| WO | WO-2011038132 A1 | 3/2011 |
| WO | WO-2011038134 A1 | 3/2011 |
| WO | WO-2011052003 A1 | 5/2011 |
| WO | WO-2011059745 A1 | 5/2011 |
| WO | WO-2011127069 A1 | 10/2011 |
| WO | WO-2011127118 A1 | 10/2011 |
| WO | WO-2012017199 A1 | 2/2012 |
| WO | WO-2012033870 A1 | 3/2012 |
| WO | WO-2012087963 A1 | 6/2012 |
| WO | WO-2012087982 A2 | 6/2012 |
| WO | WO-2013116517 A2 | 8/2013 |
| WO | WO-2014013489 A1 | 1/2014 |
| WO | WO-2014063253 A1 | 5/2014 |
| WO | WO-2014164232 A1 | 10/2014 |
| WO | WO-2014164566 A2 | 10/2014 |
| WO | WO-2016040499 A1 | 3/2016 |
| WO | WO-2016044336 A1 | 3/2016 |
| WO | WO-2016073562 A1 | 5/2016 |
| WO | WO-2016172438 A1 | 10/2016 |
| WO | WO-2017011273 A1 | 1/2017 |
| WO | WO-2017066468 A1 | 4/2017 |
| WO | WO-2017139687 A1 | 8/2017 |
| WO | WO-2019222711 A1 | 11/2019 |
| WO | WO-2022140696 A1 | 6/2022 |

OTHER PUBLICATIONS

Fukui et al. "Relationship between color development and protein conformation in the phycocyanin molecule", 2004, Dyes and Pigments, vol. 63, p. 89-94. (Year: 2004).*

Glazer et al. "Fluorescent Tandem Phycobiliprotein Conjugates", Sep. 1983, Biophysical Journal, vol. 43, p. 383-386. (Year: 1983).*

Moran, "Synechococcus vulcanus J.J.Copeland 1936" page from AlgaeBase, last updated Apr. 6, 2021. G.M. Guiry in Guiry, M.D. & Guiry, G.M. AlgaeBase. World-wide electronic publication, National University of Ireland, Galway. www.algaebase.org; searched on Oct. 11, 2023. p. 1-2. (Year: 2021).*

Rastogi et al. "Physico-chemical factors affecting the in vitro stability of phycobiliproteins from Phormidium rubidum A09DM", Apr. 29, 2015, Bioresource Technology, vol. 190, p. 219-226. (Year: 2015).*

MacColl, "Cyanobacterial Phycobilisomes", Dec. 15, 1998, Journal of Structural Biology, vol. 124, pp. 311-334. (Year: 1998).*

Fass, "Disulfide Bonding in Protein Biophysics", published online Dec. 20, 2011, Annual Review of Biophysics, vol. 41, p. 63-79. (Year: 2011).*

Puzorjov et al. "Phycobiliproteins from extreme environments and their potential applications", published online Mar. 19, 2020, Journal of Experimental Botany, vol. 71, Issue 13, p. 3827-3842. (Year: 2020).*

Business Wire, "Lumen Bioscience Announces Issuance of US Patent for Genetic Modification of Spirulina," Nov. 26, 2018, 3 pages.

David et al. "High-Resolution Crystal Structures of Trimeric and Rod Phycocyanin," Journal of Molecular Biology 405(1):201-213 (2010).

International Search Report and Written Opinion issued by the International Searching Authority for Application No. PCT/US2019/042072, dated Oct. 22, 2019, 15 pages.

IP et al. "pH-induced conformational changes of AcrA, the membrane fusion protein of Escherichia coli multidrug efflux system," Journal of Biological Chemistry 278(50):50474-50482 (2003).

(56) References Cited

OTHER PUBLICATIONS

Maccoll, "Allophycocyanin and energy transfer," Biochima et Biophys Acta. 1657:73-81 (2004).
Martelli et al. "Thermal stability improvement of blue colorant C-Phycocyanin from Spirulina platensis for food industry applications," Process Biochemistry 49(1):154-159 (2014).
Su et al. Structural insights into the cold adaptation of the photosynthetic pigment-protein C—phycocyanin from an Arctic cyanobacterium. Biochimica et Biophysica Acta 1858:325-335 (2017).
A935Y7—UniProtKB Database—2008, 2 pages.
Agarwal et al., "Gastrointestinal and Liver Manifestations of COVID-19," J Clin Exp Hepatol. May-Jun. 2020; 10(3): 263-265. Published online Apr. 1, 2020.
Akiyama, et al., "Nucleotide Sequence of Plasmid pAG1 of Marine Cyanobacterium synechococcus sp. PCC7002", DNA Res., 1998, vol. 5, pp. 127-129.
Altschul et al., Basic Local Alignment Search Tool, Journal of molecular biology, Oct. 1990, pp. 403-410.
Alvarez et al., "Triacylglycerols in prokaryotic microorganisms," Appl. Microbial. Biotechnol. 60:367-376, 2002.
Alvey et al., "Attachment of noncognate chromophores to CpcA of Synechocystis sp. PCC 6803 and Synechococcus sp. PCC 7002 by heterologous expression in Escherichia coli.," Biochemistry 50(22):4890-4902 (2011).
Alvey et al., "Effects of Modified Phycobilin Biosynthesis in the Cyanobacterium synechococcus sp. Strain PCC 7002," Journal of Bacteriology, 193(7):1663-1671 (2011).
Alvin, J. W and Lacy, D.B., Clostridium difficile toxin glucosyltransferase domains in complex with a non-hydrolyzable UDP-glucose analogue. J Struct Bioi. Jun. 2017;198(3):203-209. doi: 10.1016/j.jsb.2017.04.006. Epub Apr. 19, 2017. PMID: 28433497; PMCID:PMC5534367. (Year: 2017).
Ambati et al., "Astaxanthin: Sources, Extraction, Stability, Biological Activities and its Commercial Applications—a Review", Marine Drugs, Jan. 2014, vol. 12, 25 pgs.
Andersen K, et.al., "Neutralization of Clostridium difficile Toxin B Mediated by Engineered Lactobacilli That Produce Single-Domain Antibodies", Infection and Immunity, Nov. 2015, vol. 84 No. 2, pp. 395-406.
Angermayr, et al., "Engineering a cyanobacterial cell factory for production of lactic acid," (2012) Applied and Environmental Microbiology 78: 7098-7106 (2012).
Anonymous: UPI0000000F3D, Jul. 23, 2007 (Jul. 23, 2007), Retrieved from the Internet: URL:https://www.uniprot.org/uniparcUPI0000000F3D [retrieved on Nov. 8, 2018], 3 pages.
Anonymous: UPI0000000F3E, Jan. 23, 2007 (Jan. 23, 2007), Retrieved from the Internet: URL:https://www.uniprot.org/uniparc/UPI0000000F3E [retrieved on Nov. 8, 2018], 3 pages.
Anonymous: UPI00001BA0B6, Oct. 1, 2003 (Oct. 1, 2003), XP055522054, Retrieved from the Internet: URL:https://www.uniprot.org/uniparc/UPI00001BAOB6 [retrieved on Nov. 8, 2018], 2 pages.
Anonymous: UPI00001BA0C5, Oct. 1, 2003 (Oct. 1, 2003), Retrieved from the Internet: URL:https://www.uniprot.org/uniparc/UPI00001BA0C5[retrieved on Nov. 8, 2018], 2 pages.
Anonymous: UPI00001BAOCB, Oct. 1, 2003 (Oct. 1, 2003), Retrieved from the Internet: URL:https://www.uniprot.org/uniparc/UPI00001BAOCB[retrieved on Nov. 8, 2018], 2 pages.
Assiri et al., "Epidemiological, demographic, and clinical characteristics of 47 cases of Middle East respiratory syndrome coronavirus disease from Saudi Arabia: a descriptive study," Lancet Infect Dis Sep. 2013;13(9):752-61.
Bailey, et al., "Photoprotection in Cyanobacteria: Regulation of Light Harvesting", Photochemistry and Photobiology, vol. 84, No. 6, Nov. 1, 2008, pp. 1410-1420.
Ballicora et al, "ADP-Glucose Pyrophosphorylase, a Regulatory Enzyme for Bacterial Glycogen Synthesis", Microbiology and Molecular Biology Reviews, Jun. 2003, vol. 67, No. 2, 14 pgs.

Barrera., et al. "Algal chloroplast produced camelid VHH antitoxins are capable of neutralizing botulinum neurotoxin." Plant biotechnology journal 13.1 (2015): 117-124. (Year: 2015).
Barzegari et al. "The Search for a Promising Cell Factory System for Production of Edible Vaccine," Human Vaccines & Immunotherapeutics 10(8):2497-2502 (2014).
Beckmann, et al., "Improvement of light to biomass conversion by de-regulation of light-harvesting protein translation in Chlamydomonas reinhardtii", Journal of Biotechnology, vol. 142, No. 1, Jun. 1, 2009, Elsevier Science Publishers, pp. 70-77.
Bhattacharya et al., "Evaluation of Three Spirulina Species Grown Under Similar Conditions for Their Growth and Biochemicals," Journal of the Science of Food and Agriculture, 2005, vol. 85, pp. 333-336.
Biswas, Avijit, "Identification and characterization of enzymes involved in the biosynthesis of different phycobiliproteins in cyanobacteria" ( 2011). University of New Orleans Theses and Dissertations. 446. Retrieved from the Internet Nov. 19, 2018: URL:https://scholarworks.uno.edu/cgi/viewcontent.cgi?referer=https://www.bing.com/&httpsredir=l&article=1244&context=td, 211 pages.
Blot et al., "Phycourobilin in Trichromatic Phycocyanin from Oceanic Cyanobacteria Is Formed Post-translationally by a Phycoerythrobilin Lyase-Isomerase," J. Biol. Chem., 284(14):9290-8 (2009).
Bouvier-Nave, et al., "Expression in yeast and tobacco of plant cDNAs encoding acyl CoA: diacylglycerol acyltransferase", Eur. J. Biochem, 2000, vol. 267, pp. 85-96.
Buikema et al., "Expression of the Anabaena hetR gene from a copper-regulated promoter leads to heterocyst differentiation under repressing conditions," Proc. Natl. Acad. Sci. USA, 98:2729-2734 (2001).
Burgers et al., "Structure of smAKAP and its regulation by PKA-mediated phosphorylation," FEBS J. 283(11):2132-2148 (2016).
Buschiazzo et al., "Crystal structure of Glycogen Synthase: Homologous Enzymes Catalyze Glycogen Synthesis and Degradation", The EMBO Journal, Jul. 2004, vol. 23, No. 16, 10 pgs.
Cai Y.A., et al., "Recombinant Phycobiliproteins: Recombinant C-Phycocyanins Equipped with Affinity Tags, Oligomerization, and Biospecific Recognition Domains," Analytical Biochemistry, Mar. 2001, vol. 290(2), pp. 186-204.
Cao Breeding and characterization of amino acid-analogue-resistant mutants of Arthrospira platensis. World Journal of Microbiology and Biotechnology, Rapid Communications of Oxford 30. 423-428 (2013).
Chen, et al., "Structure of the full-length Clostridium difficile toxin B." Nature structural & molecular biology 26.8 (2019): 712-719. (Year: 2019).
Chen et al., "Well-tolerated Spirulina extract inhibits influenza virus replication and reduces virus-induced mortality," Scientific Reports 6(1), pp. 1-11 (2016). Retrieved from the Internet: URL:https://www.nature.com/articles/srep24 253.pdf.
Christensen et al., "Lipid domains of mycobacteria studied with fluorescent molecular probes," Molecular Microbiolof!V 31(5):1561-1572, 1999.
Christie, "Coenzyme A and Acyl Carrier Protein: Structure, Occurrence, Biology and Analysis", retrieved on Sep. 14, 2012, at lipidlibrary.aocs.org, Scottish Crop Research Institute, Feb. 24, 2011, pp. 1-4.
Chung et al., "Insertional inactivation studies of the csmA and csmC genes of the green sulfur bacterium Chlorobium vibrioforme 8327: the chlorosome protein CsmA is required for viability but CsmC is dispensable," FEMS Microbiol. Lett., 1998; 164: 353-361.
Chungjatupornchai et al., "Isolation and Characterization of Synechococcus PCC7942 Promoters: tRNApro Gene Functions as a Promoter" Current Microbiology 38: 210-216, 1999.
Coates et al, "Characterization of Cyanobacterial Hydrocarbon Composition and Distribution of Biosynthetic Pathways", PLOS one, vol. 9, Jan. 2014, pp. 1-12.
Cohen et al., "Construction of biologically functional bacterial plasmids in vitro," Proc. Natl. Acad Sci. US.A. 70:3240-3244 (Nov. 1973).

(56) References Cited

OTHER PUBLICATIONS

Coleman et al., "Physiological and Nutritional Regulation of Enzymes of TriacylglycerolSynthesis," Annu. Rev. Nutr. 20:77-103, Jan. 1, 2000.

Cooper, et al., "Evolution of Thermal Dependence of Growth Rate of *Escherichia coli* Populations during 20,000 Generations in a Constant Environment", Evolution, vol. 55, No. 5, 2001, pp. 889-896.

Courchesne, et al., "Enhancement of lipid production using biochemical, genetic and transcription factor engineering approaches", Journal of Biotechnology, Elsevier Science Publishers, Amsterdam, NL, vol. 141, No. 1-2, Apr. 20, 2009, pp. 31-41.

Crawford et al., "Protocol and Reagents for Pseudotyping Lentiviral Particles with SARS-CoV-2 Spike Protein for Neutralization Assays," Viruses. May 6, 2020;12(5):513, 15 pages.

Dahlqvist, et al., "Phospholipid:diacylglycerol acyltransferase: An enzyme that catalyzes the acyl-CoA-independent formation of triacylglycerol in yeast and plants." Proc Natl Acad Sci USA (2000); 97 (12): 6487-6492.

Daniel et al., "Induction of a Novel Class of Diacylglycerol Acyltransferases and Triacylglycerol Accumulation in *Mycobacterium tuberculosis* as It Goes into a Dormancy-Like State in Culture" Journal of Bacteriology 186(15): 5017-5030, Aug. 2004.

Database UNIPROT entry P00308. C-phycocyanin-1 alpha chain. [online]. Oct. 24, 2015 [retrieved Nov. 17, 2016). Available on the internet: , 2 pages.

Database UNIPROT entry P00312. C-phycocyanin-1 beta chain. [online]. Jun. 24, 2015, 6 pages retrieved Nov. 17, 2016). Available on the internet: , 3 pages.

Daum et al., "Biochemistry, Cell Biology and Molecular Biology of Lipids of *Saccharomyces cerevisiae*," Yeast 14:1471-1510, 1998.

Dauvillee David et al., "Engineering the Chloroplast Targeted Malarial Vaccine Antigens in Chlamydomonas Starch Granules," PloS One 2010, vol. 5, issue 12, e15424, 8 pages.

Davis et al., "Overproduction of Acetyl-CoA Carboxylase Activity Increases the Rate of Fatty Acid Biosynthesis in *Escherichia coli*," The Journal of Biological Chemistry 275(37):28593-28598, Sep. 15. 2000.

De Philippis et al., "Exocellular polysaccharides from cyanobacteriaand their possible applications," FEMS Microbiol. Reviews, 1998; 22:151-175.

Dehghani J, et.al., "Stable transformation of Spirulina (Arthrospira) platensis: a promising microalga for production of edible vaccines", Applied Microbiology and Biotechnology, Nov. 2018, vol. 102 No. 21, pp. 9267-9278.

Devereux et al. "A comprehensive set of sequence analysis programs for the VAX" Nucleic Acids Research 12(1):387-395 (Jan. 11, 1984).

Dobrikova AG et al, "Effect of partial or complete elimination of light-harvesting complexes on the surface electric properties and the functions of cyanobacterial photosynthetic membranes", Physiologia Plantarum, 2013, 147(2):248-260 Epub Jun. 22, 2012.

Dong et al, "Four Different Methods Comparison for Extraction of Astaxanthin from Green Alga *Haematococcus dluvialis*", The Scientific World Journal, vol. 2014, Jan. 2014, Article ID 694305, 6 pgs.

Dorne et al., "Do thylakoids really contain phosphatidylcholine?" Proc. Natl. Acad. Sci. USA, vol. 87, Jan. 1990, pp. 71-74.

Ducat et al. "Engineering Cyanobacteria to Generate High Value Products", Review, Special Issue—Applied Microbiology, Trends in Biotechnology, Feb. 2011, vol. 29, No. 2, 9 pgs.

Duran et al., "The efficient functioning of photosynthesis and respiration in *Synechocystis* sp. PCC 6803 strictly requires the presence of either cytochrome c6 or plastocyanin," J. of Biol. Chem., 2004; 279:7229-7233.

Espinosa et al., "Cross-talk And Regulatory Interactions Between The Essential Response Regulator Rpab And Cyanobacterial Circadian Clock Output," Proceedings of the National Academy of Sciences, 12(7):2198-2203 (2015).

Extended European Search Report for European Application No. EP20834359 dated Jun. 30, 2023,7 pages.

Extended European Search Report issued by the European Patent Office for Application No. 19802590.0, dated Feb. 3, 2022, 6 pages.

Fang et al., "Rapid mutation of Spirulina platensis by a new mutagenesis system of atmospheric and room temperature plasmas (ARTP) and generation of a mutant library with diverse phenotypes," PLoS One 8, e77046, pp. 1-12 (Oct. 2013).

Fu et al., "Mass-Spectral Identification and Purffication of Phycoerythrobilin and Phycocyanobilin," J. Biochem. 179:1-6 (1979).

Fujisawa et al, "Genomic Structure of an Economically Important Cyanobacterium, Arthrospira (Spirulina) Platensis NIES-39", DNA Research 17, Advance Access Publication Mar. 2010, pp. 85-103.

Gao, et al., "A Novel Cyanophage with a Cyanobacterial Nonbleaching Protein A Gene in the Genome", Journal of Virology, Jan. 2012, vol. 86, No. 1, pp. 236-245.

GenBank, Accession No. BX569694.1, Feb. 2015, www.ncbi.nlm.nih.gov.

GenBank Accession No. CP000100. Synechococcus elongatus PCC 7942, complete genome (Dec. 2007), 3 pages.

Giallourou et al. A novel mouse model of Campylobacter jejuni enteropathy and diarrhea. PLoS Pathog. 14(3): e1007083, pp. 1-23 (2018).

Gibson, et al., "Enzymatic assembly of DNA molecules up to several hundred kilobases." Nature Methods (Apr. 12, 2009); 6(5): 343-345.

Gormley et al., "Pathogen cross-transmission via building sanitary plumbing systems in a full scale pilot test-rig," PLOS ONE Feb. 10, 2017, 13 pages.

Gribskov and Burgess, "Sigma factors from *E. coli*, B. subtilis, phage SP01, and phage T4 are homologous proteins", Nucleic Acids Res. Aug. 26, 1986; 14(16): 6745-63.

Gu et al., "COVID-19: Gastrointestinal Manifestations and Potential Fecal-Oral Transmission," Gastroenterology. May 2020;158(6):1518-1519. Epub Mar. 3, 2020.

Hallmann et al., "Gene replacement by homologous recombination in the multicellular green alga Volvox carteri," Proc. Natl. Acad. USA, 1997; 94:7469-7474.

Han et al., "Digestive Symptoms in COVID-19 Patients With Mild Disease Severity: Clinical Presentation, Stool Viral RNA Testing, and Outcomes," Am J Gastroenterol. Jun. 2020;115(6):916-923.

Han et al., "The Cellular Functions of the Yeast Lipin Homolog Pahlp are Dependent on Its Phosphatidate Phosphatase Activity" The Journal of Biological Chemistry 282(51): 37026-37035, Dec. 21, 2007.

Han et al., "The *Saccharomyces cerevisiae* Lipin Homolog Is a Mg2+-dependent Phosphatidate Phosphatase Enzyme" The Journal of Biological Chemistry 281(14): 9210-9218, Apr. 7, 2006.

Harker et al., "Biosynthesis of Ketocarotenoids in Transgenic Cyanobacteria Expressing the Algal Gene for B-C-4-Oxygenase, crtO", FEBS Letters 404, Jan. 1997, 6 pgs.

Harwood, "Recent advances in the biosynthesis of plant fatty acids", Biochimica et Biophysica Acta (BBA)—Lipids and Lipid Metabolism, vol. 1301, No. 1-2, May 1, 1996, pp. 7-56.

Hasunma et al. Biotechnology for Biofuels (2014) 7:493.

He et al., "The high light-inducible polypeptides in Synechocystis PCC6803. Expression and function in high light," J. Biol. Chem., 2001; 276:306-314.

Herranen et al., "Regulation of photosystem I reaction center genes in *Synechocystis* sp. strain PCC 6803 during Light acclimation," Plant Cell Physiol., 2005; 46:1484-1493.

Hickman et al, "Glycogen Synthesis is a Required Component of the Nitrogen Stress Response in Synechococcus Elongatus PCC 7942", Algal Research, Feb. 2013, pp. 98-106.

Hiroaki Kato et al: "Interactions Between Histidine Kinase NbIS and the Response Regulators RpaB and SrrA are Involved in the Bleaching Process of the Cyanobacterium Synechococcus elongatus PCC 7942", Plant and Cell Physiology 52(12):2115-2122 (2011).

Hobbs, et al., "Cloning of a cDNA encoding diacylglycerol acyltransferase from *Arabidopsis thaliana* and its functional expression." FEBS Lett (1999); 452 (3): 145-149.

(56) References Cited

OTHER PUBLICATIONS

Hofvander et al., "A prokaryotic acyl-CoA reductase performing reduction of fatty acyl-CoA to fatty alcohol", Elsevier B. B., FEBS Letters, Federation of European Biochemical Societies, 2011, 585, 6 pages.
Hu et al., "Microalgal triacylglycerols as feedstocks for biofuel production: perspectives and advances", The Plant Journal, vol. 54, 2008, pp. 621-639.
Imamura et al., "Growth Phase-dependent Activation of Nitrogen-relatedGenes by a Control Network of Group 1 and Group 2 Factors in a Cyanobacterium*," J. Biol. Chem., 281:2668-2675 (2006).
Imashimizu et al, "Thymine at-5 Is Crucial for cpc Promoter Activity of Synechocystis sp. Strain PCC 6714", Journal of Bacteriology, Nov. 2013, vol. 185, No. 21, 4 pgs.
International Search Report and Written Opinion issued by the International Searching Authority for Application No. PCT/US2020/040794, dated Oct. 19, 2020, 15 pages.
International Search Report and Written Opinion issued by the International Searching Authority for Application No. PCT/US2022/013529, mailed May 6, 2022, 9 pages.
Iwai et al., "Improved genetic transformation of the thermophilic cyanobacterium, Thermosynechococcus elongatus BP-1," Plant Cell Physiol., 2004; 45:171-175.
Jako, et al., "Seed-Specific Over-Expression of an *Arabidopsis* cDNA Encoding a Diacylglycerol Acyltransferase Enhances Seed Oil Content and Seed Weight." Plant Physiol (2001); 126 (2): 861-874.
Jakobiak et al., "The bacterial paromomycin resistance gene, aphH, as a dominant selectable marker in Volvox carteri," Protist, 2004 155:381-393.
Jantaro et al, "Suppression of the Lethality of High Light to a Quadruple HLI Mutant by the Inactivation of the Regulatory Protein PfsR in Synechocystis PCC 6803", Journal of Biological Chemistry, vol. 281, No. 41, Oct. 2006, 10 pgs.
Jeamton et al., Overcoming Intrinsic Restriction Enzyme Barriers Enhances Transformation Efficiency in Arthrospira platensis CI. Plant and Cell Physiology 58, 822-830 (2017).
Jiang et al., "Inhibition of Fatty Acid Synthesis in *Escherichia coli* in the Absence of Phospholipid Synthesis and Release of Inhibition by Thioesterase Action," Journal of Bacteriology 176(10):2814-2821, 1994.
Jin et al, "Crystal Structure of Potato Tuber ADP-Glucose Pyrophosphorylase", The EMBO Journal, Feb. 2005, vol. 24, No. 4, 11 pgs.
Joet et al., "Involvement of a plastid terminal oxidase in plastoquinone oxidation as evidenced by expression of the *Arabidopsis thaliana* enzyme in tobacco," J Biol Chem. (2002) 277:31623-31630.
Jung et al., "Candidate Genes for the Phycoerythrocyanin Subunit Lyase. Biochemical Analysis Of pecE and pecF Interposon Mutants," J. Biol. Chem., 270, 12877-12884 (1995).
Kaczmarzyk et al., "Fatty Acid Activation in Cyanobacteria Mediated by Acyl-Acyl Carrier Protein Synthetase Enables Fatty Acid Recycling," Plant Physiology, vol. 152, Mar. 2010, pp. 1598-1610.
Kahn et al., "rpbA controls transcription of the constitutive phycocyanin gene set in Fremyella diplosiphon," J. Bacterial. 179(24): 7695-7704 (1997).
Kaiser et al., "Fatty Aldehydes in Cyanobacteria Are a Metabolically Flexible Precursor for a Diversity of Biofuel Products", PLOS One, vol. 8, No. 3, Mar. 11, 2013, 11 pages.
Kalscheuer and Steinbchel, "A Novel Bifunctional Wax Ester Synthase/Acyl-CoA:Diacylglycerol Acyltransferase Mediates Wax Ester and Triacylglycerol Biosynthesis in Acinetobacter calcoaceticus ADP1." The Journal of Biological Chemistry (2002); 278 (10): 8075-8082.
Kalscheuer, et al., "Analysis of Storage Lipid Accumulation in Alcanivorax borkumensis: Evidence for Alternative Triacylglycerol Biosynthesis Routes in Bacteria", Journal of Bacteriology, vol. 189, No. 3, Feb. 2007, pp. 918-928.
Kalscheuer et al., "Microdiesel: *Escherichia coli* engineered for fuel production," Microbiology 152:2529-2536, 2006.
Kalscheuer et al., "Neutral Lipid Biosynthesis in Engineered *Escherichia coli*: Jojoba Oil-Like Wax Esters and Fatty Acid Butyl Esters," Applied and Environmental Microbiology 72(2):1373-1379, 2006.
Karradt, et. al., "NbIA, a Key Protein of Phycobilisome Degradation, Interacts with ClpC, a HSP100 Chaperone Partner Jf a Cyanobaceterial Clp Protease", The Journal of Biological Chemistry vol. 283, No. 47, Nov. 21, 2008, 18 pages.
Kawata et al., "Transformation of Spirulina platensis by chromosomal integration," Algal Biotechnology, Ceske Budejovice, Czech Republic Sep. 6-11, 1993 : Progress in Biotechnology of Photoautotrophic Microorganisms : 6th International Conference on Applied Algology : Book of Abstracts, Department of Autotrophic Microorganisms, Jan. 1, 1993 (Jan. 1, 1993), p. 72,,abstract 2 pages.
Khan Z, et.al., "Nutritional and therapeutic potential of Spirulina", Current Pharmaceutical Biotechnology, Oct. 2005, vol. 6 No. 5, pp. 373-379.
Khozin-Goldberg, et al., "Unraveling algal lipid metabolism: Recent advances in gene identification", Biochimie, Masson, Paris, FR, vol. 93, No. 1, Jan. 1, 2011, pp. 91-100.
Kim et al., "Infection and Rapid Transmission of SARS-CoV-2 in Ferrets," Kim et al., 2020, Cell Host & Microbe 27, 704-709. May 13, 2020.
Kindle et al., Stable nuclear transformation of Chlamydomonas using the Chlamydomonas gene for nitrate reductase, J. Cell Biol., 1989; 109:2589-2601, retrieved from jcb.rupress.org on Nov. 6, 2018.
Kirst et al., "Maximizing photosynthetic efficiency and culture productivity in cyanobacteria upon minimizing the phycobilisome light-harvesting antenna size," Biochim Biophys Acta 1837(10):1653-1654 (2014).
Klanchui et al., Systems Biology and Metabolic Engineering of Arthrospira Cell Factories. Computational and Structural Biotechnology Journal 3(4):e201210015-8, pp. 1-8 (Oct. 2012).
Koksharova et al., "Genetic tools for cyanobacteria," Appl. Micrbiol. Biotechnol. 58:123-137, 2002.
Kurreck, Antisense Technologies, Eur. J. Biochem 2003 270_1628-1644.
Kwon, et al., "Reduced light-harvesting antenna: Consequences on cyanobacterial metabolism and photosynthetic productivity", Algal Research, vol. 2, No. 3, May 24, 2013, pp. 188-195.
Larter, "The Navy is locking down staff at boot camp for up to 90 days," Navy Times, 4 pages, Mar. 25, 2020.
Lazar, E. et al., "Transforming Growth Factor α: Mutation of Aspartic Acid 47 and Leucine 48 Results in Different Biological Activities," Molecular and Cellular Biology, 8(3):1247-1252 (1988).
Lea-Smith, et al., "Phycobilisome-Deficient Strains of *Synechocystis* sp. PCC 6803 Have Reduced Size and Require Carbon-Limiting Conditions to Exhibit Enhanced Productivity," Plant Physiology, vol. 165(2), Jun. 2014, pp. 705-714.
Lenski, et al., "Evolutionary Response of *Escherichia coli* to Thermal Stress", The American Naturalist, vol. 142, Supplement: Evolutionary Responses to Environmental Stress, 1993, pp. S47-S64.
Leung et al., "Enteric involvement of severe acute respiratory syndrome-associated coronavirus infection," Gastroenterology. Oct. 2003;125(4):1011-1017.
Li et al., "Characterization of *Synechocystis* sp. Strain PCC 6803 and Deltanbl Mutants under Nitrogen-Deficient Conditions", Arch Microbial Jun. 29, 2002, vol. 178, No. 4, pp. 256-266.
Li et al., "Role of air distribution in SARS transmission during the largest nosocomial outbreak in Hong Kong," IIndoor Air. Apr. 2005;15(2):83-95. doi: 10.1111/j.1600-0668.2004.00317.x.
Li et al., "Substantial undocumented infection facilitates the rapid dissemination of novel coronavirus (SARS-CoV-2)," Science 2020, 6 pages.
Liang et al, "Carotenoid Biosynthesis in Cyanobacteria: Structural and Evolutionary Scenarios Based on Comparative Genomics", Intl Journal of Biological Sciences, Aug. 2006, 2(4), pp. 197-207.
Liu et al., "CO2-limitation-inducible Green Recovery of fatty acids from cyanobacterial biomass," PNAS Early Edition, www.pnas.org/cgi/doi/10.1073/pnas.1103016108, 2011. (4 pages). es.

(56) References Cited

OTHER PUBLICATIONS

Liu et al., "Fatty acid production in genetically modified cyanobacteria," PNAS Early Edition, www.pnas.org/cgi/doi/10.1073/pnas.1103014108, 2011. (6 pages).

Liu et al., "Production and secretion of fatty acids in genetically engineered cyanobacteria," Proc Natl Acad Sci U S A . Jul. 2, 2010, 6 pages.

Lu et al, "Molecular Cloning and Characterization of the pgm Gene Encoding Phosphoglucomutase of *Escherichia coli*", Journal of Bacteriology, Sep. 1994, vol. 176, No. 18, 6 pgs.

Ludwig et al., "Transformation and gene replacement in the facultatively chemoheterotrophic, unicellular cyanobacterium *Synechocystis* sp. PCC6714 by electroporation.," Appl. Microbiol. Biotechnol., 2008; 78:729-735.

Luque et al., "Convergence of two global transcriptional regulators o nitrogen induction of the stress acclimation gene nblA i the cyanobacterium *Synechococcus* sp. PCC 7942," (Molecular Microbiology (2001), 41(4), 937-947).

Lykidis et al., "Genomic prospecting for microbial biodiesel production," U.S. Department of Energy Office of Science, Biological and Environmental Research Program and The University of California, Lawrence Berkele National Laboratory, 2008. 39 pages.

Macete E., et al., "Safety and Immunogenicity of the RTS,S/AS02A Candidate Malaria Vaccine in Children Aged 1-4 in Mozambique, " Tropical Medicine and International Health 2007, vol. 12, No. 1, pp. 37-46.

MacIntyre, et al., "Photoacclimation of Photosynthesis Irradiance Response Curves and Photosynthetic Pigments in Microalgae and Cyanobacteria", Journal of Phycology, vol. 38, No. 1, Feb. 1, 2002, pp. 17-38.

Maddox et al, "Elevated Serum Levels in Human Pregnancy of a Molecule Immunochemically Similar to Eosinophil Granule Major Basic Protein", Journal Exp. Med, vol. 158, Oct. 1983, 16 pgs.

Maeda et al., "cis-acting sequences required for NtcB-dependent, nitrite-responsive positive regulation of the nitrate assimilation operon in the cyanobacterium *Synechococcus* sp. strain PCC 7942," J. Bacterial.; 180:4080-4088 (1998).

Makino et al, "Characterization of Cyanobacterial Carotenoid Ketolase CrtW anad Hydroxylase CrtR by Complementation Analysis in *Escherichia coli*", Pant Cell Physiology, Oct. 2008, vol. 49, No. 12, 12 pgs.

Mali, et al., "RNA-Guided Human Genome Engineering via Cas9", Science, Feb. 15, 2013, vol. 339(6121), pp. 823-826.

Marin et al., J. Bacteriol., "Salt-Dependent Expression of Glucosylglycerol-Phosphate Synthase, Involved in Osmolyte Synthesis in the *CyanobacteriumSynechocystis* sp. Strain PCC 6803," 2002; 184:2870-2877.

Marin et al., "Osmotic stress in *Synechocystis* sp. PCC 6803: low tolerance towards nonionic osmotic stress results from lacking activation of glucosylglycerol accumulation," Microbiology, 152, p. 2023-2030, Mar. 13, 2006.

Marin et al., Plant Physiol., "Gene Expression Profiling Reflects PhysiologicalProcesses in Salt Acclimation of *Synechocystis*sp. Strain PCC 6803," 2004; 136:3290-3300.

Mary et al., "Effects of high light on transcripts of stress-associated genes for the cyanobacteria *Synechocystis* sp. PCC 6803 and *Prochlorococcus* MED4 and MIT9313," Microbiol., 2004; 150:1271-1281.

Matsui et al., "Microbial Interactions Affecting the Natural Transformation of Bacillus Subtilis in a Model Aquatic Ecosystem," FEMS Microbiology Ecology 45(3):211-218 (2003).

Mcdonald et al., "Flexibility In Photosynthetic Electron Transport: The Physiological Role of Plastoquinol Terminal Oxidase (PTOX)," Biochimica et Biophysica Acta (BBA)—Bioenergetics 1807(8): pp. 954-967 (2011).

Mell et al., Natural Competence and the Evolution of DNA Uptake Specificity. Journal of Bacteriology 196:1471-1483 (2014).

Mendez-Alvarez et al., "Transformation of Chlorobium limicola by a plasmid that confers the ability to utilize thiosufate," J. Bacterial., 176:7395-7397 (1994).

Mermet-Bouvier et al., "A Conditional Expression Vector for the Cyanobacteria *Synechocystis* sp. Strains PCC6803 and PCC6714 or *Synechococcus* sp. Strains PCC7942 and PCC6301" Current Microbiology 28: 145-148, 1994.

Mermet-Bouvier et al., "Transfer and Replication ofRSFI0IO-Derived Plasmids in Several Cyanobacteria of the Genera *Synechocystis* and *Synechococcus*," Current Microbiology 27:323-327, 1993.

Miao, et al., "Changes in Photosynthesis and Pigmentation in an agp Deletion Mutant of the Cyanobacterium *Synechocystis* sp.", Biotechnology Letters, Mar. 2003, vol. 25, No. 5, pp. 391-396.

Mongold et al., "Evolutionary Adaptation to Temperature. IV. Adaptation of *Escherichia coli* at a Niche Boundary," Evolution, vol. 50, No. 1, 1996, pp. 35-43.

Morgan-Kiss et al., "The *Escherichia coli*fadK (ydiD) Gene Encodes an Anerobically Regulated Short Chain Acyl-CoA Synthetase," The Journal of Biological Chemistry 279(36):37324-37333, 2004.

Moronta-Barrios, et al., "In vivo features of signal transduction by the essential response regulator RpaB from Synechococcus elongatus PCC 7942", Microbiology, vol. 158, No. 5, 2012, pp. 1229-1237.

Muramatsu et al., "Characterization of high-light-responsive promoters of the psaAB genes in *Synechocystis* sp. PCC 6803," Plant Cell Physiol., 47:878-890 (2006).

Nakajima et al., "Improvement of microalgal photosynthetic productivity by reducing the content of light harvesting pigment", Journal of Applied Phycology, Kluwer Academic Publishers, Apr. 1, 1999, pp. 195-201.

Nakajima, et al., "Improvement of photosynthesis in dense microalgal suspension by reduction of light harvesting pigments", Journal of Applied Phycology, vol. 9, Dec. 1, 1997, pp. 503-510.

Nakajima, et al., "Reduced photoinhibition of a phycocyanin-deficient mutant of Synechocystis PCC 6714", Journal of Applied Phycology, vol. 10, No. 5, Jan. 1, 1998, pp. 447-452.

Nakamura et al., "Plastidic Phosphatidic Acid Phosphatases Identified in a Distinct Subfamily of Lipid Phosphate Phosphatases with Prokaryotic Origin," The Journal of Biological Chemistry 282(39):29013-29021, 2007.

NCBI Gene ID 951909 "glgc glucose-1-phosphate adenylyltransferase [*Synechocystis* sp. PCC 6803]" Aug. 2003 downloaded from http://www.ncbi.nlm.nih.gov/gene on Jun. 2, 2011, 2 pages.

NCBI Reference Sequence NC_016640.1, dated Jun. 11, 2013, 1 page.

NCBI taxonomy, 2 pages; https://www.ncbi.nlm.nih.gov/Taxonomy/Browser/wwwtax.cgi?mode=Info&id=118562&1vl=3&1in=f&keep=1 &srchmode=1 accessed Jul. 19, 2023 (Year: 2023).

Nedbal et al., "A photobioreactor system for precision cultivation of photoautotrophic microorganisms and for high-content analysis of suspension dynamics," Biotechnol. Bioeng., 2008; 100:902-910.

Niederholtmeyer, et al., "Engineering cyanobacteria to synthesize and export hydrophilic products," (2010) Applied and Environmental Microbiology 76: 3462-3466.

Nishizuka, "Intracellular Signaling by Hydrolysis of Phospholipids and Activation of Protein Kinase C" Science 258: 607-614, Oct. 23, 1992.

Ohnuma et al., "Polyethylene Glycol (PEG)-Mediated Transient Gene Expression in a Red Alga, *Cyanidioschyzon merolae* 10D," Plant Cell Physiol., 49:117-120 (2008).

Page, et al., "Reduction of Photoautotrophic Productivity in the Cyanobacterium *Synechocystis* sp. Strain PCC 6803 bl Phycobilisome Antenna Truncation", Applied and Environmental Microbiology, vol. 78, No. 17, Sep. 1, 2012, pp. 5349-6351.

Perrineau, et al., "Evolution of Salt Tolerance in a Laboratory Reared Population of Chlamydomonas Reinhardtii", Environmental Microbiology, vol. 16, No. 6, 2014, pp. 1755-1766.

Perrone et al., "The Chlamydomonas IDA7 Locus Encodes a 140-kDaDynein Intermediate Chain Required to Assemble the I1 Inner Arm Complex," Molecular Biology of the Cell vol. 9, 3351-3365 (1998).

Qi et al., "Application of the Synechococcus nirA Promoter to Establlish an Inducible Expression System for Engineering the Synechocystis Tocopherol Pathway", Applied and Environmental Microbiology, Oct. 2005, vol. 71, No. 10, 7 pgs.

(56) References Cited

OTHER PUBLICATIONS

Qiu et al., "Metabolic engineering of Aeromonas hydrophila for the enhanced production of poly(3-hydroxybutyrate-co-3-hydroxyhexanoate)," Appl. Mircobiol. Biotechnol. 69:537-542, 2006.

Quintana, et al., "Renewable energy from Cyanobacteria: energy production optimization by metabolic pathway engineering," Appl Microbiol Biotechnol 91:471-490 (2011).

Radakovits et al., "Genetic Engineering of Algae for Enhanced Biofuel Production", Eukaryotic Cel, vol. 9, No. 4, Apr. 2010, pp. 486-501.

Ramey et al., Genome Engineering in Cyanobacteria: Where We Are and Where We Need To Go, ACS Synthetic Biol. 4:1186-96 (2015).

Riazi et al. Pentavalent Single-Domain Antibodies Reduce Campylobacter jejuni Motility and Colonization in Chickens. PLoS One 8(12):e83928, pp. 1-12 (2013).

Ronen-Tarazi et al, "The Genomic Region of rbcLS in *Synechococcus* sp. PCC 7942 Contains Genes Involved in the Ability to Grow Under Low CO2 Concentration and in Chlorophyll Biosynthesis", Plant Physiol., vol. 108, Aug. 1995, 9 pgs.

Rosales-Mendoza S., "Algae-based biopharmaceuticals", Cham: Springer, 2016, 172 pages.

Rothan and Byrareddy "The epidemiology and pathogenesis of coronavirus disease (COVID-19) outbreak," J Autoimmun. May 2020;109:102433 5 pages. Epub Feb. 26, 2020.

Ruffing, "Engineered cyanobacteria Teaching an old bug new tricks", Bioengineered Bugs, vol. 2, No. 3, May 1, 2011, Sandia National Laboratories, pp. 136-149.

Ruffing, et al., "Physiological Effects of Free Fatty Acid Production in Genetically Engineered Synechococcus elongatus PCC 7942", Biotechnology and Bioengineering, vol. 109, No. 9, Sep. 9, 2012, pp. 2190-2199.

Saerens et al., "Identification of a Universal VHH Framework to Graft Non-canonical Antigen-binding Loops of Camel Single-domain Antibodies", J. Mol. Biol. (2005) 352, 597-607.

Saha et al., "Cytosolic Triacylglycerol Biosynthetic Pathway in Oilseeds. Molecular Cloning and Expression of Peanut Cytosolic Diacylglycerol Acyltransferase" Plant Physiology 141: 1533-1543, Aug. 2006.

Samartzidou et al., "Transcriptional and posttranscriptional control of mRNA from IrtA, a light-repressed transcript in *Synechococcus* sp. PCC 7002," Plant Physiol., 1998; 117:225-234.

Sato, et. al., "sll1961 is a novel regulator of phycobilisome degradation during nitrogen starvation in the yanobacterium *Synechocystis* sp PCC 6803", FEBS Letters 582, 2008, 4 pages.

Schirmer et al., "Microbial Biosynthesis of Alkanes," Science, vol. 329, Jul. 30, 2010, pp. 559-562.

Sendersky, et. al., "NbIC, a novel component required for pigment degradation during starvation in Synechococcus DCC 7942", Molecular Microbiology 58(3), Sep. 22, 2005, 11 pages.

SEQ ID: WP_178888959.1, dated Jun. 7, 2022, 1 page.

Sharp and Li, "The codon Adaptation Index—a measure of directional synonymous codon usage bias, and its potential applications." Nucleic Acids Res (1987); 15(3): 1281-1295.

Singh et al., "Bioactive Compounds from Cyanobacteria and Microalgae: An Overview," Critical Reviews in Biotechnology 25:73-95, 2005.

Skruglewicz, et al., Edible Algae System—(Growing Spirulina in space). Steps to Growing Spirulina Algae. Blog post (online). Element 14. Oct. 17, 2020 [retrieved on Apr. 1, 2022]. Retrieved from the Internet: https://community.element14.com/challenges-projects/design-challenges/1-meter-of-pi/b/blog/posts/blog-1-eas---steps-to-growing-spirulina-algae], 11 pages.

Smith, T.F. and Waterman, M.S., "Comparison of Biosequences," Advances in Applied Mathematics 2(4), Dec. 1981, pp. 482-489.

Song, et al., "Exploitation of Oil-bearing Microalgae for Biodiesel," Chinese Journal of Biotechnology, vol. 24, No. 1, Mar. 1, 2008, pp. 341-348, retrieved on Mar. 1, 2008.

Soni, R.A., et al., "Spirulina—From growth to nutritional product: A review," Trends in Food Science & Technology, vol. 69, Part A, Nov. 2017, pp. 157-171.

Sorger et al., "Triacylglycerol biosynthesis in yeast," Appl Microbiol Biotechnol, vol. 61, 2003, pp. 289-299.

Specht, E.A., et al., "Algae-based oral recombinant vaccines," Front Microbial, Published on Feb. 17, 2014, vol. 5—2014, URL: https://doi.org/10.3389/fmicb.2014.00060, 7 pages.

Steinbrenner et al., "Transformation of the Green Alga *Haematococcus pluvialis* with a Phytoene Desaturase for Accelerated Astaxanthin Biosynthesis," Appl Environ. Microbiol., 2006; 72:7477-7484.

Stoveken, et al., "Bacterial Acyltransferases as an Alternative for Lipase-Catalyzed Acylation for the Production of Oleochemicals and Fuels," Angew. Chem Int. Ed. 47: 3688-3694 (2008).

Stoveken, et al., "The Wax Ester Synthase/Acyl Coenzyme A:Diacylglycerol Acyltransferase from *Acinetobacter* sp. Strain ADP1: Characterization of a Novel Type of Acyltransferase." J Bacteriol (2005); 187 (4): 1369-1376.

Sun et al., "Functional complementation of a nitrate reductase defective mutant of a green alga *Dunaliella viridis* by introducing the nitrate reductase gene," (2006) Gene, 377: 140-149 (2006).

Suzuki, et al., "Carbohydrate Metabolism in Mutants of the Cyanobacterium Synechococcus elongatus PCC 7942 Defective in Glycogen Synthesis", Applied and Environmental Microbiology, vol. 76, No. 10, May 15, 2010, pp. 3153-3159.

Swanson, et al., "Characterization of Phycocyanin Produced by cpcE and cpcF Mutants and Identification of an Identification of an Intergenic Suppressor of the Defect in Bilin Attachment", The Journal of Biological Chemistry, vol. 267, No. 23, The American Society for Biochemistry and Molecular Biology, Inc., 1992, pp. 16146-16154.

Tan et al., "Establishment of a Micro-Particle Bombardment Transformation Systemfor Dunaliella salina," J. Microbiol., 2005; 43:361-365.

Taton et al. The circadian clock and darkness control natural competence incyanobacteria. Nature Communications 11(1688) pp. 1-11 (Apr. 2020).

Tilzer et al., "Light-Dependence of Photosynthesis and Growth in Cyanobacteria: Implications for their Dominance in Eutropic Lakes," N. England J. Marine and Freshwater Research. 1987. 21: 401-412).

Toyomizu et al., "Effective transformation of the cyanobacterium Spirulina platensis using electroporation," J Applied Phycology. 13, 209-214 (2001).

UniProt Accession No. A0A0D2CT51 (A0A0D2CT51_9EURO), Apr. 29, 2015 [online]. [Retrieved on Apr. 6, 2022], 8 pages, Retrieved from the InternetURL:https://!www.uniprot.org/uniprot/AOAOD2CT51 ,.

UniProt Accession No. A0A510UPM1 (A0A510UPM1_9CELL), Oct. 16, 2019 [online]. 8 pages, [Retrieved on Apr. 6, 2022]. Retrieved from the Internet URL:https://www.uniprot.org/uniprot/AOA510UPM1.

Uniprot, Accession No. Q7U4P2, 2015, www.uniprot.org., 1 page.

Van Heeke et al, "Expression of Human Asparagine Synthetase in *Escherichia coli*", The Journal of Biological Chemistry, vol. 264, No. 10, Apr. 1989, 7 pgs.

Van Heeke et al., "The N-terminal Cysteine of Human Asparagine Synthetase is Essential for Glutamine-dependent Activity" The Journal of Biological Chemistry 264(33): 19475-19477, Nov. 25, 1989.

Voelker et al., "Alteration of the Specificity and Regulation of Fatty Acid Synthesis of *Escherichia coli* by Expression of a Plant Medium-Chain Acyl-Acyl Carrier Protein Thioesterase," Journal of Bacteriology 176(23):7320-7327, 1994.

Wada et al., "Temperature-Induced Changes in the Fatty Acid Composition of the Cyanobacterium, Synechocystis PCC6803", Plant Physiology, American Society of Plant Physiologists, Rockville, MD, US, vol. 92, Jan. 1, 1990, pp. 1062-1069.

Waditee et al., "Overexpression of a Na+/H+ antiporter confers salt tolerance on a freshwater cyanobacterium, making it capable of growth in sea water," PNAS 99 (6):4109-4114 (2002).

Waltermann et al., "Key enzymes for biosynthesis of neutral lipid storage comounds in prokaryotes: Propoerties, function and occurrence of wax ester synthases/acyl-CoA:diacylglycerol acyltransferases", Biochimie 89, 2007, pp. 230-242.

(56) References Cited

OTHER PUBLICATIONS

Waltermann et al., "Mechanism of lipid-body formation in prokaryotes: how bacteria fatten up," Molecular Microbiology 55(3):750-763, 2005.

Waltermann et al., "Neutral Lipid Bodies in Prokaryotes: Recent Insights into Structure, Formation, and Relationship to Eukaryotic Lipid Depots," Journal of Bacteriology 187(11):3607-3619, 2005.

Wang, "Conditional Investigation on the Electroporation to Transformation for Spirulina platensis" (Chinese Language), High-tech Communication, Issue 10, 13 pages including English translation (2002).

Wang, et al., "Using a novel lysin to help control Clostridium difficile infections." Antimicrobial Agents and Chemotherapy 59.12 (2015): 7447-7457. (Year: 2015).

Welch et al., "Design Parameters to Control Synthetic Gene Expression in Escherichia coli," PLoS One, Sep. 2009, vol. 4, Issue 9, e7002, 10 pages.

Welch et al., "You're one in a googol: optimizing genes for protein expression," J. of the Royal Society, Interface 6 (Suppl 4):S467-S476 (2009).

WHO, WHO issues consensus document on the epidemiology of SARS, Wkly Epidemiol Rec (WER) 78 (43), 2003: 373-375.

Wirth et al., "Transformation of various species of gram-negative bacteria belonging to 11 different genera bv electroporation," Mal. Gen. Genet. 216:175-177, 1989.

Wrapp et al., "Cryo-EM Structure of the 2019-nCOV Spike in the Prefusion Conformation," bioRxiv, 30 pages. Feb. 15, 2020.

Wu, et al., "Modification of carbon partitioning to enhance PHB production in Synechocystis sp. PCC6803", Enzyme Microb. Technol., 2002, vol. 30, pp. 710-715.

Xiao et al., "Evidence for Gastrointestinal Infection of SARS-CoV-2," Gastroenterol May 2020;158(6):1831-1833, and Supplementary Material pp. E1-E3. Epub Mar. 3, 2020.

Xiaohuan Zheng, "Expression of Human Epidermal Growth Factor hEGF in Spirulina" (Chinese Language), Chinese Master's Theses Full-text Database—Basic Sciences, vol. 12, 9 pages including English translation (2009).

Xu et al., ."Characteristics of pediatric SARS-CoV-2 infection and potential evidence for persistent fecal viral shedding," Nat Med, Mar. 13, 2020.

Xue et al., "A New Strategy for Lipid Production by Mix Cultivation of Spirulina Platensis and Rhodotorula Glutinis," Applied Biochemistry and Biotechnology 160(2):498-500 (2010).

Yan et al., "The Potential for Microalgae as Bioreactors to Produce Pharmaceuticals," International Journal of Molecular Sciences 17(6), pp. 1-24 (2016).

Yen et al., "DGAT enzymes and triacylglycerol biosynthesis," Journal of Lipid Research, 49: 2283-2301 (2008).

Yeo et al., "Enteric involvement of coronaviruses: is faecal-oral transmission of SARS-CoV-2 possible?," Lancet Gastroenterol Hepatol. Apr. 2020;5(4):335-337.

Yoskikawa, et al., "Single-Laboratory Validation of a Method for the Determination of C-Phycocyanin and Allophycocyanin in Spirulina (Arthrospira) Supplements and Raw Materials by Spectrophotometry", J_ AOAC Int., 2008 vol. 91 (3), pp. 524-529.

Yu et al., "Production of Eicosapentaenoic Acid by a Recombinant Marine Cyanobacterium, Synechococcus sp." Lipids 35(10): 1061-1064, 2000.

Zhang et al., "Crystal Structure of the Carboxyltransferase Domain of Acetyl-Coenzyme a Carboxylase" Science 299: 2064-2067, Mar. 28, 2003.

Zhang et al., "Molecular and serological investigation of 2019-nCoV infected patients: implication of multiple shedding routes," Emerg Microbes Infect. Feb. 17, 2020;9(1):386-389.

Zhang et al., "Molecular effect of FadD on the regulation and metabolism of fatty acid in Escherichia coli," FEMS Microbiol. Lett. 259:249-253, 2006.

Zhang et al., "Optimum Conditions for Transformation of Synechocystis sp. PCC 6803," J. Microbiol., 2007; 45(5):241-245.

Zhang et al., "Preliminary Studies on the Genetic Transformation of Spirulina Platensis," College of Marine Life Sciences. Ocean University of Qingdao, Qingdao, F. Chen and Y. Jiang (eds.), Algae and their Biotechnological Potential, 263-269 (2001), Jul. 3-6, 2000 in Hong Kong.

Zhao et al., "Novel activity of a phycobiliprotein lyase: both the attachment ofphycocyanobilin and the isomerization to phycoviolobilin are catalyzedby the proteins PecE and PecF encoded by the phycoerythrocyaninoperon," FEBS Lett., 469:9-13 (2000).

Zhou et al., "The cpcE and cpcF Genes of Synechococcus sp. PCC 7002," J. Biol. Chem., 267:16138-16145 (1992).

Durdakova et al., Microalgae/cyanobacteria: the potential green future of vitamin B12 production. Critical Reviews in Food Science and Nutrition, 13 pages.https://doi.org/10.1080/10408398.2022.2130156 (Oct. 12, 2022).

Georgianna and Mayfield, "Exploiting diversity and synthetic biology for the production of algal biofuels," Nature 488(7411):329-35 (Aug. 16, 2012).

Kawata et al., "Transformation of Spirulina platensis strain Cl (Arthrospira sp. PCC9438) with Tn5 transposase-transposon DNA-cation liposome complex," Marine Biotechnology. 6, 355-363 (2004).

Lawson et al., "Proposal to restrict the genus Clostridium prazmowski to Clostridium butyricum and related species," International Journal of Systematic and Evolutionary Microbiology 66:1009-1016 (2016).

Murakawa et al., "Improvement of transformation efficiency by bioactive-beads-mediated gene transfer using DNA-lipofectin complex as entrapped genetic material," J. Biosci. Bioeng., 105(1): 77-80 (2008).

Office Action issued by the Chinese Patent Office for Application No. 201580048316, dated Sep. 28, 2020, 24 pages including English translation.

Page et al., "Phycobilisome antenna truncation reduces photoautotrophic productivity in Synechocystis sp. PCC 6803, a cyanobacterium," Appln. Environ. Microbiol. American Society for Microbiology, Jun. 15, 2012, 14 pages.

Wang, Fen, "Construction and Transformation of Spirulina platensis Expression Vector" (Chinese Language), Chinese Master's Theses Full-text Database—Basic Sciences, Issue 9, 56 pages including English translation (Published Sep. 15, 2009).

Wikipedia, Spirulina (dietary supplement), dated Feb. 28, 2024, pp. 1-2.

Xu, "Guidelines for Experiments on Marine Organisms" (Chinese), Ocean Press, Jun. 2004, 5 pages (Non-English).

Zhu, Yiwei, "Construction of luxAB Expression Vector of Spirulina platensis and Electroporation Transformation" (Chinese Language), Chinese Master's Theses Full-text Database—Basic Sciences, Issue S2, 28 pages including English translation (2011).

Zhang et al., "Study on the Expression of Transthymosin Gene Spirulina and Its Immune-Enhancing Activity" (Chinese), Fujian Journal of Agriculture, vol. 20, Issue 4, pp. 228-232, published on Dec. 31, 2005).

Zhenlian Ke, "Establishment of Transformation and Expression System of Spirulina platensis" (Chinese Language), Chinese Doctor's and Master's Theses Full-text Database (Master's)—Basic Sciences, Issue 1, 41 pages including English translation (2002).

* cited by examiner

FIG. 1A

(SEQ ID NO: 35)
(SEQ ID NO: 36)

FIG. 1B

(SEQ ID NO: 37)
(SEQ ID NO: 38)

FIG. 2

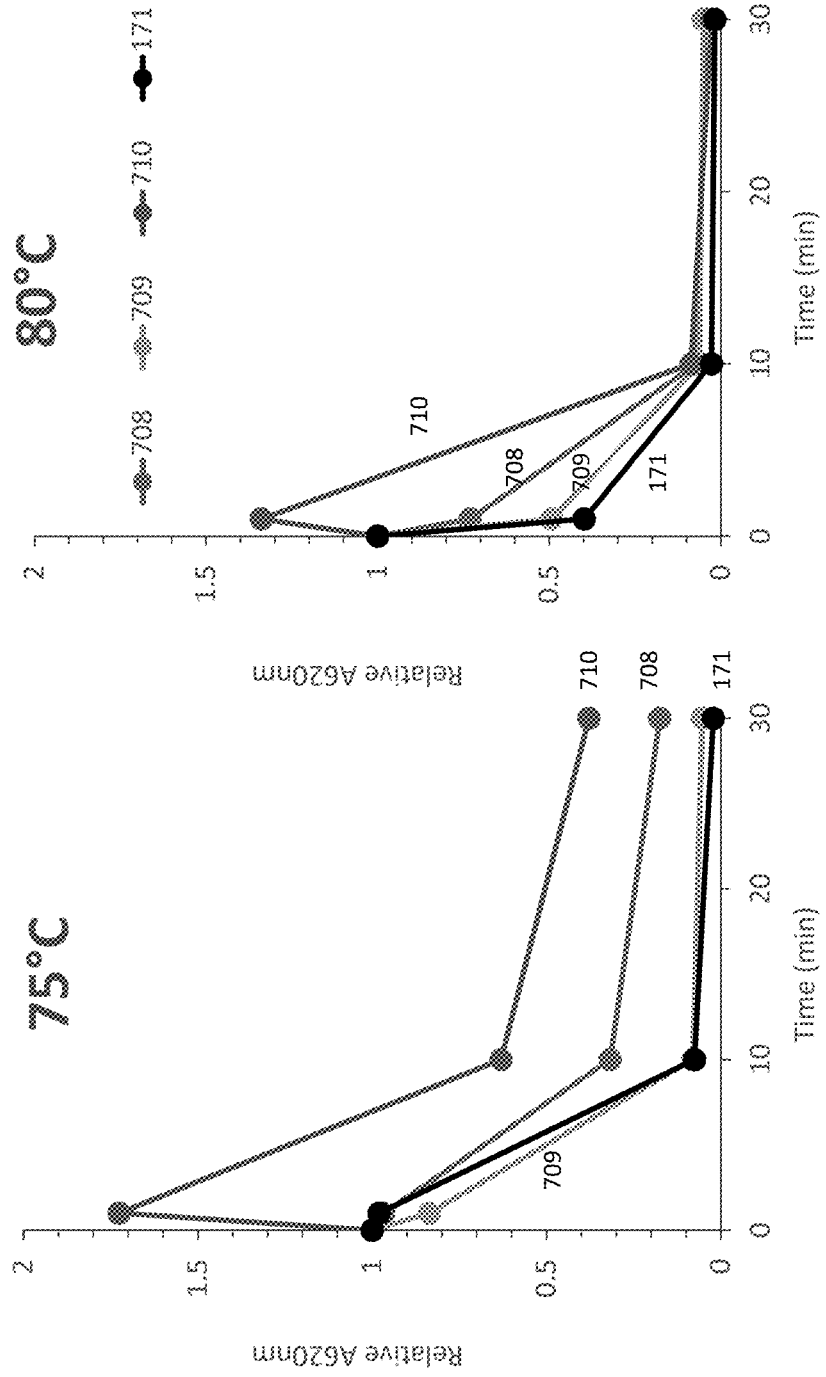

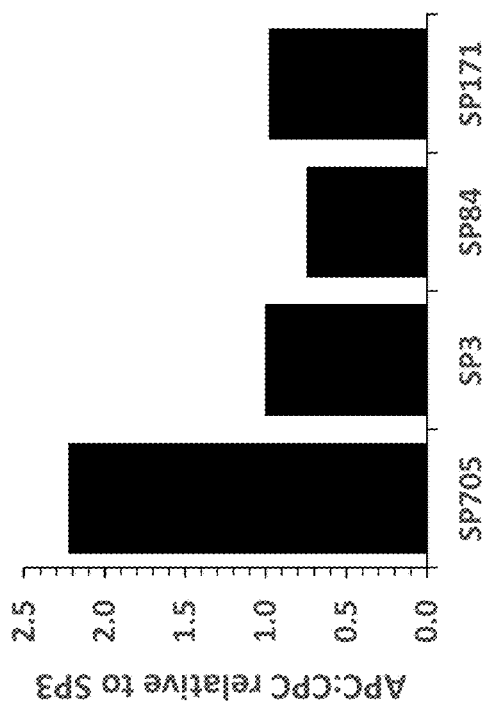
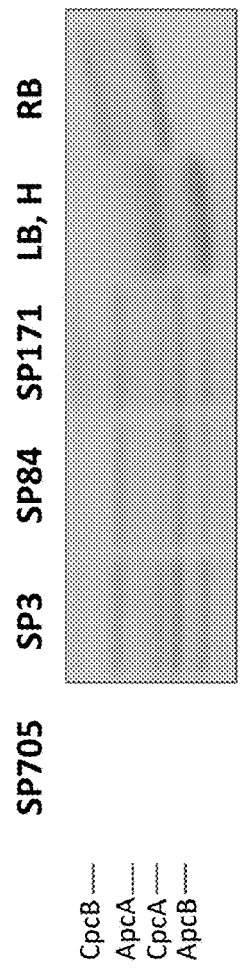
FIGURE 14A
FIG. 14B

THERMOSTABLE PHYCOBILIPROTEINS PRODUCED FROM RECOMBINANT ARTHROSPIRA

CROSS REFERENCE TO RELATED APPLICATIONS

This Application is a U.S. National Phase of PCT/US2019/042072, filed Jul. 16, 2019, which claims the benefit of priority to U.S. Provisional Application No. 62/698,712, filed on Jul. 16, 2018, the contents of each of which are hereby incorporated by reference in their entirety

INCORPORATION BY REFERENCE OF THE SEQUENCE LISTING

The contents of the text file submitted electronically herewith are incorporated herein by reference in their entirety: A computer readable format copy of the Sequence Listing (filename: LUBI_025_01US_SubSeqList_ST25.txt, date created Jun. 22, 2023, file size –117,493 bytes).

FIELD OF THE INVENTION

The disclosure is directed to thermostable phycobiliproteins such as phycocyanin and allophycocyanin. In particular, the disclosure provides modified thermostable phycobiliproteins produced in recombinant *Spirulina*. These thermostable phycobiliproteins possess increased resistance to temperature and acids.

BACKGROUND

Phycobiliproteins are water-soluble proteins present in cyanobacteria and certain algae (rhodophytes, cryptomonads, glaucocystophytes) which capture light energy, which is then passed on to chlorophylls during photosynthesis. These proteins provide color to the organism, and are a source of natural dye. However, manufacturing and production processes use high temperatures at which the phyocobiliproteins denature, thus losing their color. This temperature sensitivity limits the use of phycobiliproteins in dye manufacturing. A new source of thermostable phycobiliproteins is thus desired.

SUMMARY OF THE INVENTION

Provided herein are thermostable phycobiliproteins, recombinant *Spirulina* cells expressing these proteins, and methods of making the same. The thermostability and acid stability of the phycobiliprotein can be increased by forming disulfide bonds within the protein. In some embodiments, these bonds are formed by replacing one or more residues such as alanine, isoleucine, or aspartic acid with cysteine. These replacements may create disulfide bonds between subunits (e.g. between cpcA and cpcB) or within a subunit (e.g. within cpcA).

In some aspects, the present disclosure provides a thermostable phycobiliprotein modified for greater stability by the formation of covalent disulfide bonds. In some embodiments, the thermostable phycobiliprotein is more thermostable than a corresponding wild type or codon-optimized phycobiliprotein. In some embodiments, the covalent disulfide bonds are formed between peptide chains. In some embodiments, the covalent disulfide bonds are formed within a peptide chain. In some embodiments, the disulfide bonds are formed by replacing one or more residues to cysteine in the polypeptide. In some embodiments, one or more alanine or serine residues are replaced with one or more cysteine residues.

In some embodiments, the phycobiliprotein is obtained from an organism that can live at temperatures above 55° C. In some embodiments, the phycobiliprotein is obtained from *T. vulcanus*. In some embodiments, the phycobiliprotein is a modified phycocyanin. In some embodiments, the phycobiliprotein is stabilized by the formation of at least one disulfide bond in the CpcA subunit. In some embodiments, the phycobiliprotein is stabilized by the formation of at least one disulfide bond between alpha helices of CpcA. In some embodiments, the phycobiliprotein is stabilized by the formation of at least one disulfide bond between alpha-helices $\alpha 2$ and $\alpha 7$ or corresponding residues of CpcA. In some embodiments, the phycobiliprotein is stabilized by the formation of at least one disulfide bond between the CpcA and CpcB subunits. In some embodiments, the phycobiliprotein is stabilized by the formation of at least one disulfide bond between an alpha-helix of CpcA and the N-terminal region of CpcB. In some embodiments, the phycobiliprotein is stabilized by the formation of at least one disulfide bond between alpha-helix $\alpha 1$ of CpcA and the N-terminal region of cpcB upstream of alpha-helix $\alpha 1$ or corresponding residues. In some embodiments, the phycobiliprotein is a *T. vulcanus* CpcA where the one or more residues at positions 40 or 146 are replaced by cysteines. In some embodiments, the phycobiliprotein is a *T. vulcanus* CpcA where the residues at positions 40 and 146 are replaced by cysteines. In some embodiments any residue is replaced with cysteine. In some embodiments, one or more alanine residues are replaced with cysteine.

In some embodiments, the phycobiliprotein exhibits greater stability at elevated temperatures than the corresponding wild type phycobiliprotein. In some embodiments, the phycobiliprotein exhibits more than a two-fold increase in stability at elevated temperatures. In some embodiments, the phycobiliprotein exhibits more than a ten-fold increase in stability at elevated temperatures. In some embodiments, the phycobiliprotein exhibits more than a fifty-fold increase in stability at elevated temperatures. In some embodiments, the phycobiliprotein is stable at temperatures over 60° C. In some embodiments, the phycobiliprotein is stable at temperatures over 65° C. In some embodiments, the phycobiliprotein is stable at temperatures over 70° C. In some embodiments, the phycobiliprotein is stable at temperatures over 75° C. In some embodiments, the phycobiliprotein is thermostable for at least 10 seconds. In some embodiments, the phycobiliprotein is thermostable for about 1 minute. In some embodiments, the phycobiliprotein is thermostable for about 10 minutes. In some embodiments, the phycobiliprotein is thermostable for about thirty minutes.

In some embodiments, the disclosure provides modified *Spirulina* cells expressing a non-native thermostable phycobiliprotein of the disclosure. In some embodiments, the *Spirulina* cell retains one or more endogenous phycobiliproteins. In some embodiments, one or more endogenous phycobiliproteins are inactivated, deleted, or replaced. In some embodiments, a thermostable phycobiliprotein is integrated into the *Spirulina* genome. In some embodiments, a thermostable phycobiliprotein is maintained on an extrachromosomal plasmid. In some embodiments, the thermostable phycobiliprotein is overexpressed. In some embodiments, the thermostable phycobiliprotein is expressed at endogenous levels. In some embodiments, the thermostable phycobiliprotein is under the control of an inducible promoter.

In some embodiments, the lysate of the *Spirulina* contains a greater amount of the thermostable phycobiliprotein than the amount of one of more endogenous phycobiliproteins. In some embodiments, the ratio of thermostable phycobiliprotein::endogenous phycobiliprotein is greater than 1:1. In some embodiments, the ratio of thermostable phycobiliprotein::endogenous phycobiliprotein is greater than 1.4:1. In some embodiments, the ratio of thermostable phycobiliprotein::endogenous phycobiliprotein is greater than 2:1.

In some embodiments, the thermostable phycobiliprotein is phycocyanin. In some embodiments, the thermostable phycobiliprotein is allophycocyanin.

In some embodiments, the *Spirulina* is selected from the group consisting of: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri Stizenberger, A. jennerif. purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata f. acutissima, A. neapolitana, A. nordstedtii, A. oceanica, A. okensis, A. pellucida, A. platensis, A. platensis* var. *non-constricta, A. platensis* f. *granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor*. In some embodiments, the *Spirulina* is *A. platensis*.

In some aspects, the present disclosure provides methods of making a thermostable phycobiliprotein comprising: a) culturing the *Spirulina* composition of the present disclosure under conditions that allow expression of the phycobiliprotein; b) lysing the *Spirulina* cells in the composition; and c) recovering the thermostable phycobiliprotein.

BRIEF DESCRIPTION OF THE DRAWINGS

FIG. 1A-B shows the labeling of phycocyanin (C-PC) secondary structure features as shown in Su (2017) et al. the sequence alignments for the subunits of Ps-C-PC1 (PDB ID: 5TOU) and Ar-C-PC (PDB ID: 1GHO). Panel A shows the alpha subunit. Panel B shows the beta-subunit. Residues at the outer surface are indicated with "$". Residues at the presumable interfaces of different hexamers are indicated with "#". Chains A and B of the coordinate file Ps-C-PC (PDB ID: 5TOU) were used to calculate the secondary structure.

Figure 2:
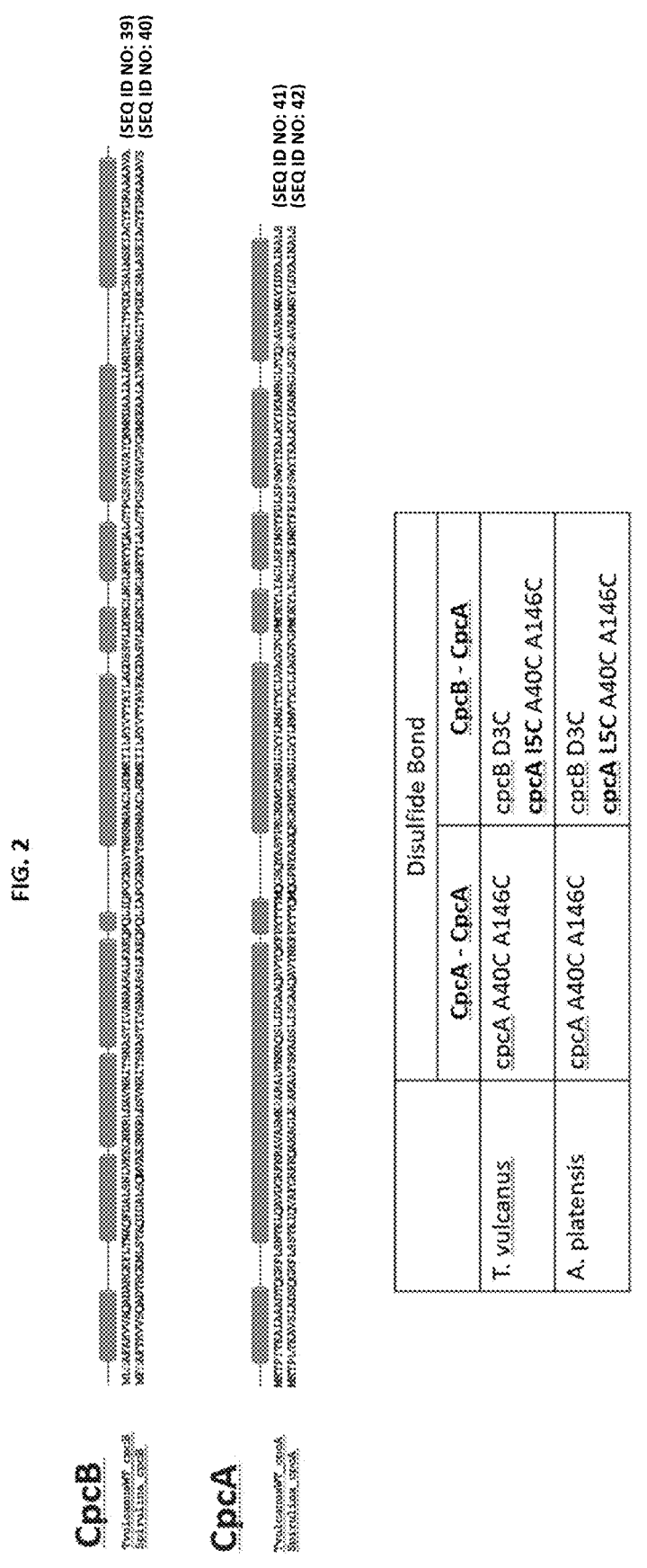

FIG. 2 shows a sequence comparison between *T. vulcanus* and *Spirulina* strain NIES39 cpcBA FIG. 3A-B. Location of phycocyanin residues mutated to cysteines. Phycocyanin is shown as a hexamer with different CpcA subunits shown in varying shades of blue and different CpcB subunits are shown in varying shades of green. A cpcB D3C and cpcA I5C mutation should result in an intermolecular disulfide bond forming when the protein is released from the cytoplasm and exposed to an oxidative environment (Panel A). An A40C mutation in conjunction with a A146C mutation facilitates disulfide bond formation within CpcA (Panel B).

FIG. 10A-D. SP710 heat-purified protein lysate is more stable than SP708, 709, and 171 at all temperatures tested. *Arthrospira platensis* CpcBA was preferentially removed from the samples by heat treatment, 65° C., 30 min, and centrifugation. The remaining soluble protein was concentrated to 1 mg/mL and assayed for thermostability at 65 (A), 70 (B), 75 (C), and 80° C. (D) and the A620 nm retained at each temperature and time-point is reported.

Figure 12:
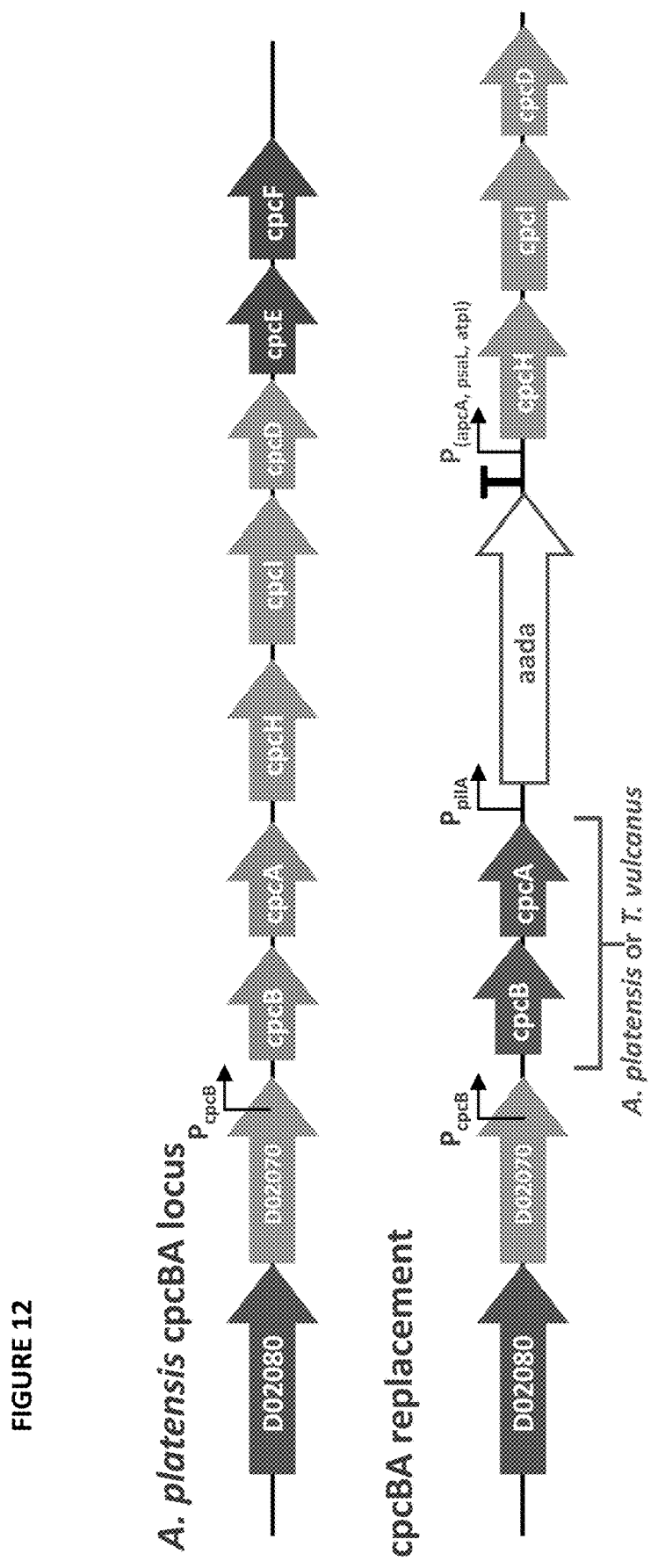

FIG. 12. Diagram of the replacement of the genomic copy of *A. platensis* cpcBA with *T. vulcanus* cpcBA. Three different promoters were used to promote expression of the remaining cpc operon independent of the cpcB promoter. As a control, the cpcBA replacement construct was also built with *A. platensis* cpcBA to ensure that integration construct was not detrimental to the cell. Fully segregated *T. vulcanus* cpcBA replacement strains were acquired when the PpsaL promoter was used to facilitate expression of the cpc operon whereas the control *A. platensis* cpcBA replacement strains could be developed with all three promoters that were tested ($P_{apcA}$, $P_{psaL}$, and $P_{atpI}$).

Figure 13:
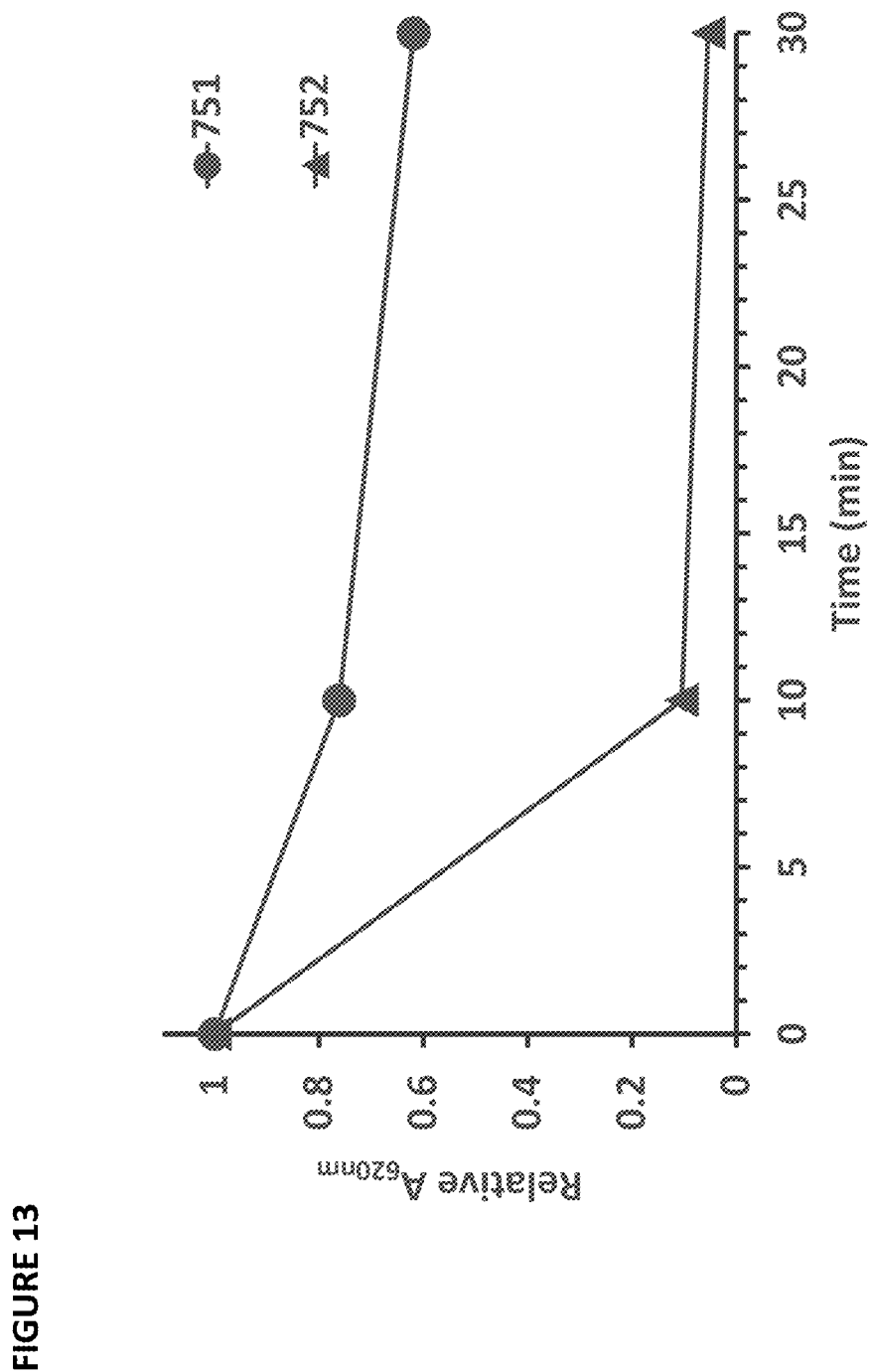

FIG. 13. Protein lysate from cells that exclusively express cpcBA from *T. vulcanus*, SP751, is substantially more stable than an analogous strain expressing *A. platensis* cpcBA (SP752). Protein lysates were treated at 65° C. for the indicated time-points, the insoluble material is removed by centrifugation, and the remaining A620 nm was measured. SP751 protein lysate retains the more color after treatment at 65° C. than the other strains. The average of three replicates is reported.

FIG. 14A-B. SP705 accumulates over two-fold more ApcAB relative to CpcBA than WT *A. platensis*, SP3. Cells were grown at 35° C., 0.2% $CO_2$, 150 μE, shaking at 125 rpm and harvested when the cultures reached $OD_{750}$ ~3. A) The soluble fraction from the harvested cells was analyzed by PAGE (1.5 μg of CPC loaded per lane) and the proteins were visualized by Coomassie stain. The APC migration standard was prepared by heat treating LinaBlue to remove CpcBA from the sample (LB, H; 65° C., 30 min). RioBlue (RB) was used as a CpcBA migration standard. B) The abundance of ApcAB and CpcBA was measured by densitometry analysis and the ratio of the sum of the intensity of ApcA and ApcB bands was compared to the sum of the CpcB and CpcA bands. The ratios are reported relative to the ratio of APC:CPC measured in SP3.

Figure 15:
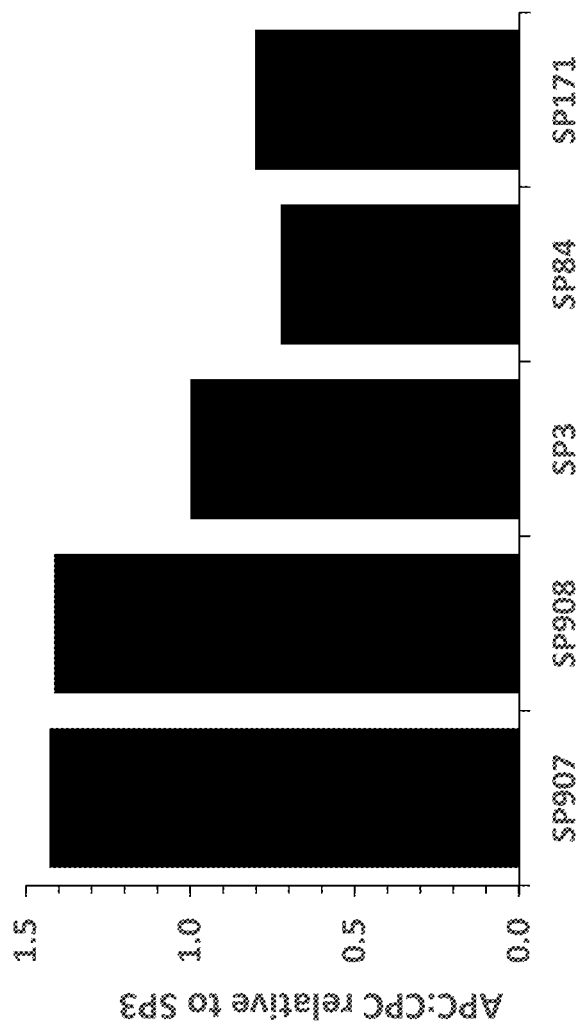

FIG. 15. *T. vulcanus* allophycocyanin overexpression strains, SP907 and SP908, accumulate 1.4-fold more APC relative to CPC than WT cells. Cells were grown at 35° C., 0.2% $CO_2$, 150 μE, shaking at 125 rpm and harvested when the cultures reached OD750 ~3. The soluble protein fraction from the harvested cells was analyzed by PAGE and the proteins were visualized by Coomassie stain. The prevalence of ApcAB and CpcBA was measured by densitometry analysis and the ratio of the sum of the intensity of ApcA and ApcB bands was compared to the sum of the CpcB and CpcA bands. The ratios are reported relative to the ratio of APC:CPC measured in SP3.

Figure 16B:
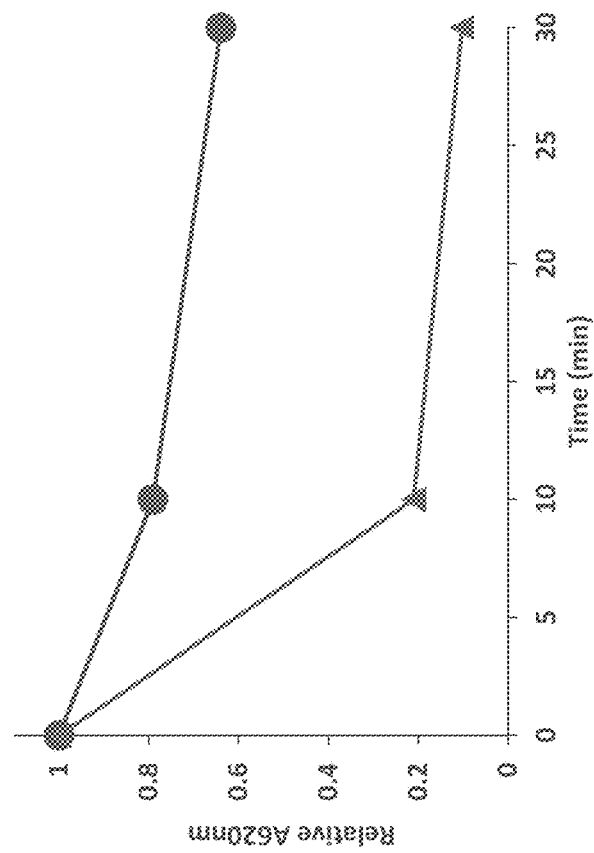
Figure 16A:
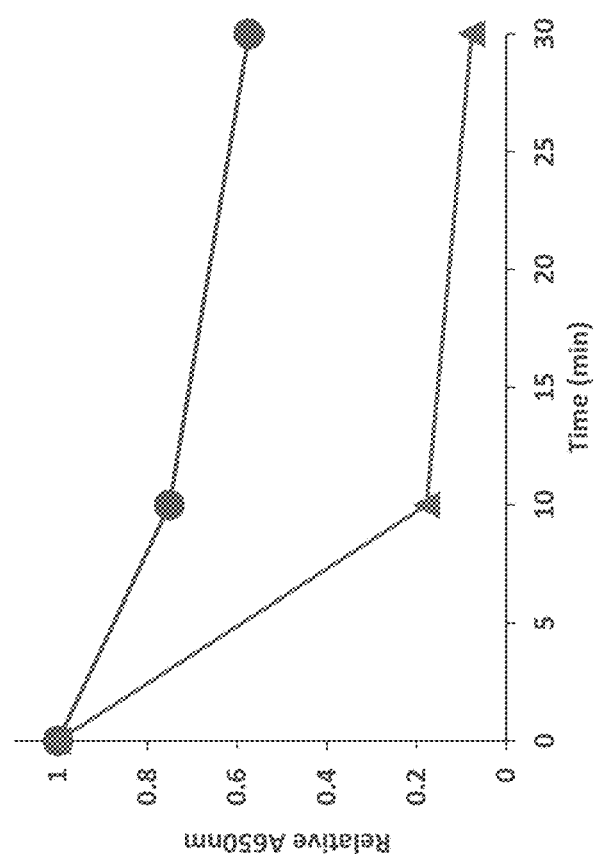

FIG. 16A-B. *T. vulcanus* allophycocyanin from heat-purified SP705 (●) protein lysate is more stable at 70° C. than *A. platensis* ApcAB purified from LinaBlue (▲). *Arthrospira platensis* CpcBA was preferentially removed from both samples by heat treatment, 65° C., 30 min, and centrifugation. The resulting soluble protein was concentrated to 1 mg/mL and assayed for thermostability. Allophycocyanin enriched samples were tested at 70° C. for the indicated times, the color remaining in the soluble fraction was measured by A620 nm (A) and A650 nm (B), and *T. vulcanus* APC, SP705, was observed to be 6.1 (A) and 7.4-fold (B) more stable than *A. platensis* ApcAB after 30 min.

DETAILED DESCRIPTION

Before describing certain embodiments in detail, it is to be understood that this disclosure is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this disclosure and in the specific context where each term is used. Certain terms are discussed below or elsewhere in the specification, to provide additional guidance to the practitioner in describing the compositions and methods of the disclosure and how to make and use them. The scope and meaning of any use of a term will be apparent from the specific context in which the term is used. As such, the definitions set forth herein are intended to provide illustrative guidance in ascertaining particular embodiments of the disclosure, without limitation to particular compositions or biological systems.

Following long-standing patent law convention, the terms "a", "an", and "the" refer to "one or more" when used in this application, including the claims, unless clearly indicated otherwise. By way of example, "a thermostable phycobiliprotein" means one thermostable phycocyanin or more than one thermostable phycobiliprotein.

The term "subject" as used herein refers to a vertebrate or an invertebrate, and includes mammals, birds, fish, reptiles, and amphibians. Subjects include humans and other primates, including non-human primates such as chimpanzees and other apes and monkey species. Subjects include farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like; and aquatic animals such as fish, shrimp, and crustaceans.

The term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Thermostable Phycobiliproteins

The present disclosure provides for the development, production, and synthesis of thermostable phycobiliproteins. Phycobiliproteins (e.g. phycocyanin, allophycocyanin, and phycoerythrin) have many industrial and pharmaceutical uses, some of which benefit from the availability of phycobiliproteins that can withstand temperatures greater than 45° C. Such phycobiliproteins have been identified in thermophilic organisms, but the present disclosure provides novel modified phycobiliproteins that improve protein thermostabilty.

In some embodiments, the thermostable phycocyanin is based on or derived from any appropriate thermophilic organism. In some embodiments, the thermophilic organism is a photosynthetic organism. In some embodiments, the thermophilic organism lives and grows at temperatures over 45° C. In some embodiments, the thermophilic organism lives and grows at temperatures over 55° C. In some embodiments, the thermophilic organism is a plant, fungus, algae, blue-green algae, archaebacteria, or bacteria. In some embodiments, the thermophilic organism is a Cyanobacteria. In some embodiments, the thermophilic organism is selected from the group including, but not limited to, *T. vulcanus, Synechococcus* A/B clade, *Cyanidium caldarium, Synechococcus lividus*, and *Cyanidioschyzon*.

In some embodiments, present disclosure provides a modified thermostable phycobiliprotein. In some embodiments, the modified thermostable phycobiliprotein is between about 99% to about 70% identical to a corresponding wild type or codon-optimized phycobiliprotein. In some embodiments, the modified thermostable phycobiliprotein is about 99%, about 98%, about 97%, about 96%, about 95%, about 94%, about 93%, about 92%, about 91%, about 90%, about 85%, about 80%, about 75%, or about 70% identical to a corresponding wild type or codon-optimized phycobiliprotein. The determination of sequence identity between two sequences (e.g., between a native sequence and a functional analog) can be accomplished using any alignment tool, including for example, that disclosed in Tatusova et al., *Blast 2 sequences—a new tool for comparing protein and nucleotide sequences, FEMS Microbiol Lett.* 174:247-250 (1999). In some embodiments, the corresponding wild type phycobiliprotein or codon-optimized is a phycocyanin or a subunit or a fragment thereof. In some embodiments, the corresponding wild type or codon-optimized phycobiliprotein is an allophycocyanin or a subunit or fragment thereof. In some embodiments, the corresponding wild type or codon-optimized phycobiliprotein is a phycoerythrin or a subunit or fragment thereof. In some embodiments, the modified thermostable phycobiliprotein is functional. Such activity can be measured using any appropriate assay, including those described herein.

In some embodiments, the modified thermostable phycobiliprotein comprises amino acid insertions, deletions, and/or substitutions with respect to a corresponding wild type or codon-optimized phycobiliprotein. In some embodiments, the modified thermostable phycobiliprotein contains about 1 to 10 amino acid insertions, deletions, and/or substitutions with respect to a corresponding wild type or codon-optimized phycobiliprotein. In some embodiments, the modified thermostable phycobiliprotein contains about 1, about 2, about 3, about 4, about 5, about 6, about 7, about 8, about 9, or about 10 amino acid insertions, deletions, and/or substitutions with respect to a corresponding wild type or codon-optimized phycobiliprotein.

In some embodiments, the thermostable phycobiliprotein is in a fusion protein. In some embodiments, the fusion protein comprises multiple copies of the same phycobiliprotein. In some embodiments, the fusion protein comprises different phycobiliproteins. In some embodiments, the fusion protein comprises multiple copies of the same and different phycobiliproteins.

In some embodiments, the thermostable phycobiliproteins comprises modifications that stabilize or create disulfide bonds in the polypeptide. In some embodiments, the disulfide bonds occur between different subunits of the polypeptide. In some embodiments, the disulfide bonds occur within a subunit. In some embodiments, the disulfide bonds occur between different subunits of the polypeptide and within a subunit.

Figures 1A, 1B:
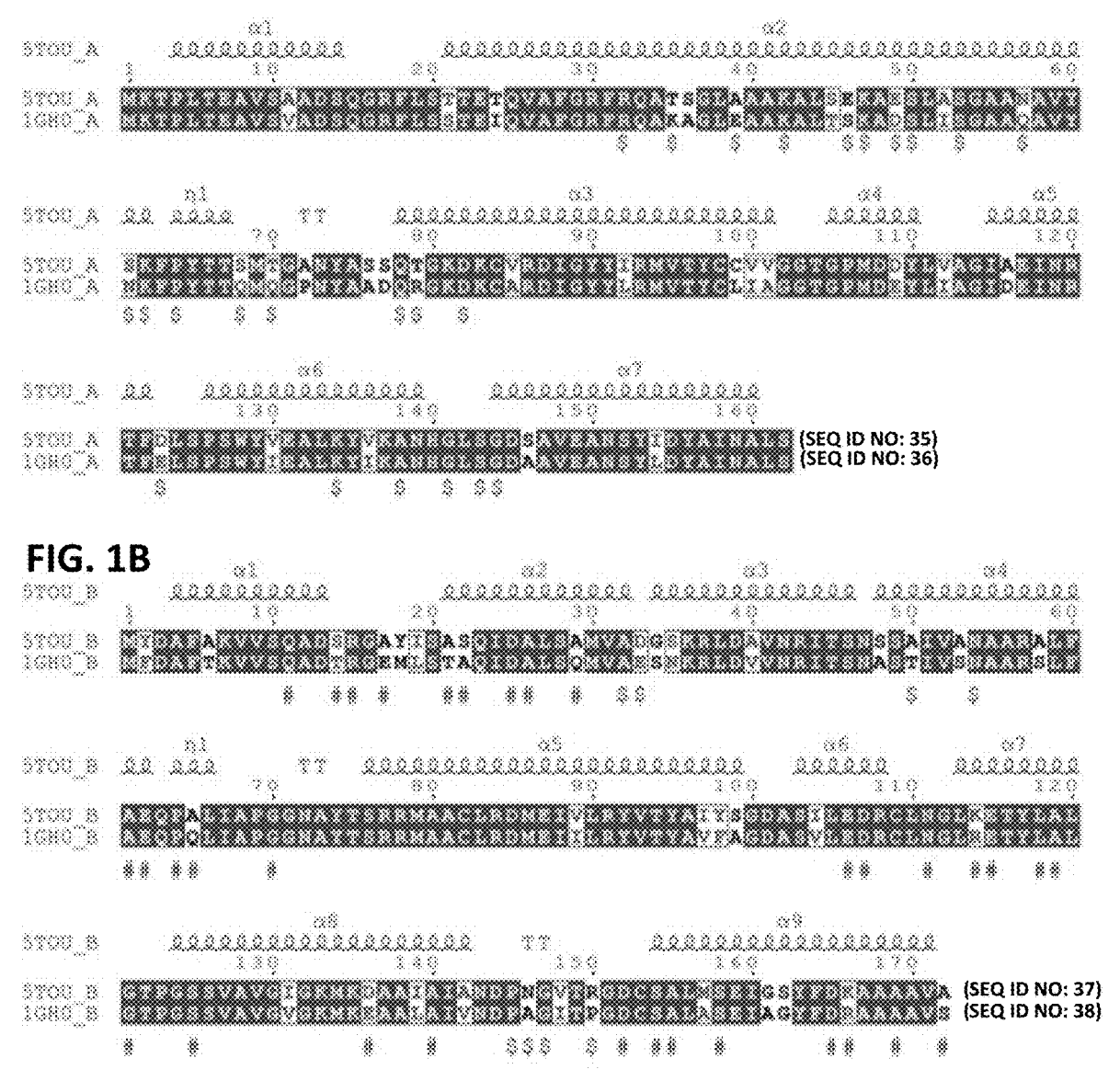

In some embodiments, one or more residues in the amino acid sequence of the phycobiliprotein are replaced with a cysteine residue. In some embodiments, any amino acid in the phycobiliprotein is replaced with a cysteine. In some embodiments, the one or more amino acid residues replaced with a cysteine residue are alanine, serine, isoleucine, or aspartic acid residues. In some embodiments, the replacement of one or more amino acid residues with cysteine forms a disulfide bond between subunits of a phycobiliprotein. In some embodiments, replacement of one or more amino acid residues with cysteine forms a disulfide bond within one subunit (i.e. intramolecular) of a phycobiliprotein. In some embodiments, the phycobiliprotein is stabilized by the formation of at least one disulfide bond between alpha helices. In some embodiments, the phycobiliprotein is stabilized by the formation of at least one disulfide bond between alpha helices in the CpcA subunit. In some embodiments, the phycobiliprotein is a phycocyanin that is stabilized by the formation of at least one disulfide bond between alpha helices in the CpcA subunit. In some embodiments, the phycobiliprotein is a phycocyanin that is stabilized by the formation of at least one disulfide bond between alpha-helices α2 and α7 as described in Su et al (2017) (FIG. 1).

In some embodiments, replacement of one or more amino acid residues with cysteine forms a disulfide bond between two subunits (i.e. intermolecular) of a phycobiliprotein. In some embodiments, the phycobiliprotein is stabilized by the formation of at least one disulfide bond between CpcA and CpcB. In some embodiments, the phycobiliprotein is stabilized by the formation of at least one disulfide bond between an alpha helix on one subunit and a terminus of the other. In some embodiments, the phycobiliprotein is stabilized by the formation of at least one disulfide bond between an alpha helix on CpcA and the N-terminal region of CpcB. In some embodiments, the phycobiliprotein is stabilized by the formation of at least one disulfide bond between alpha-helix α1 of CpcA and the N-terminal region of cpcB upstream of alpha-helix α1 as described in Su et al (2017) (FIG. 1).

In some embodiments, replacement of one or more amino acid residues with cysteine forms a disulfide bond both between subunits of a phycobiliprotein and also within one or more subunits.

In some embodiments, the thermostable phycobiliprotein is a phycocyanin. In some embodiments, the thermostable phycocyanin is obtained from a thermophilic organism. In some embodiments, the thermophilic organism is *T. vulcanus*. In some embodiments, the phycocyanin is a codon optimized phycocyanin. In some embodiments, the phycocyanin is codon optimized for expression in *Spirulina*. In some embodiments, the phycocyanin is codon optimized for expression in *A. platensis*. In some embodiments, the phycocyanin is further modified to replace one or more amino acid residues with cysteine. Any appropriate amino acid position may be replaced, and the skilled artisan would understand that the residue positions recited herein are exemplary, and may differ based upon differences in the original phycobiliprotein sequences. Thus, while specific positions are recited herein, corresponding positions that create the same structure in a different phycobiliprotein may be replaced with similar effect.

In some embodiments, the phycocyanin contains a codon-optimized cpcA subunit containing one or more of the following replacements to the recited positions or corresponding positions: L5C/I5C, A40C, and/or A146C or a combination thereof. In some embodiments, the phycocyanin contains a codon-optimized cpcB subunit containing a D3C or corresponding position replacement.

In some embodiments, the polynucleotide sequence encoding the codon-optimized phycocyanin is SEQ ID NO: 1, SEQ ID NO: 3, SEQ ID NO: 6, SEQ ID NO: 8, SEQ ID NO: 14, SEQ ID NO: 16, SEQ ID NO: 19, or a combination thereof. In some embodiments, the polynucleotide sequence encoding the codon-optimized phycocyanin is expressed from the plasmid of SEQ ID NO: 5, SEQ ID NO: 10, SEQ ID NO: 13, SEQ ID NO: 18, or SEQ ID NO: 21. In some embodiments, the thermostable phycocyanin comprises the amino acid sequence of SEQ ID NO: 2, SEQ ID NO: 4, SEQ ID NO: 7, SEQ ID NO: 9, SEQ ID NO: 12, SEQ ID NO: 15, SEQ ID NO: 15, SEQ ID NO: 17, SEQ ID NO: 20, or a combination thereof. In some embodiments, the polynucleotide sequence encoding the codon-optimized phycocyanin is at least about 80% identical to SEQ ID NO: 1, SEQ ID NO: 3, SEQ ID NO: 6, SEQ ID NO: 8, SEQ ID NO: 14, SEQ ID NO: 16, SEQ ID NO: 19, or a combination thereof. In some embodiments, the polynucleotide sequence encoding the codon-optimized phycocyanin is expressed from a plasmid at least 80% identical to SEQ ID NO: 5, SEQ ID NO: 10, SEQ ID NO: 13, SEQ ID NO: 18, or SEQ ID NO: 21. In some embodiments, the thermostable phycocyanin comprises an amino acid sequence at least 80% identical to SEQ ID NO: 2, SEQ ID NO: 4, SEQ ID NO: 7, SEQ ID NO: 9, SEQ ID NO: 12, SEQ ID NO: 15, SEQ ID NO: 15, SEQ ID NO: 17, SEQ ID NO: 20, or a combination thereof.

In some embodiments, the thermostable phycobiliprotein is allophycocyanin. In some embodiments, the allophycocyanin is obtained from a thermophilic organism. In some embodiments, the thermophilic organism is *T. vulcanus*. In some embodiments, the allophycocyanin is a codon optimized allophycocyanin. In some embodiments, the allophycocyanin is codon optimized for expression in *Spirulina*. In some embodiments, the allophycocyanin is codon optimized for expression in *A. platensis*. In some embodiments, the allophycocyanin is further modified to replace one or more amino acid residues with cysteine. In some embodiments, polynucleotide expressing the allophycocyanin is SEQ ID NO: 22, SEQ ID NO: 24, SEQ ID NO: 27, SEQ ID NO: 29, or a combination thereof. In some embodiments, the allophycocyanin comprises the amino acid sequence of SEQ ID NO: 23, SEQ ID NO: 25, SEQ ID NO: 28, SEQ ID NO: 30, or a combination thereof. In some embodiments, the allophycocyanin is expressed from the plasmid of SEQ ID NO: 18. In some embodiments, polynucleotide expressing the allophycocyanin is at least 80% identical to SEQ ID NO: 22, SEQ ID NO: 24, SEQ ID NO: 27, SEQ ID NO: 29, or a combination thereof. In some embodiments, the allophycocyanin comprises an amino acid sequence at least 80% identical to SEQ ID NO: 23, SEQ ID NO: 25, SEQ ID NO: 28, SEQ ID NO: 30, or a combination thereof. In some embodiments, the allophycocyanin is expressed from a plasmid at least 80% identical to SEQ ID NO: 18.

In some embodiments, the modified thermostable phycobiliprotein is encoded by a nucleotide sequence between about 99% to about 70% identical to the nucleic acid sequence of a corresponding wild type or codon optimized phycobiliprotein. In some embodiments, the modified thermostable phycobiliprotein is about 99%, about 98%, about 97%, about 96%, about 95%, about 94%, about 93%, about 92%, about 91%, about 90%, about 85%, about 80%, about 75%, or about 70% identical to the nucleotide sequence of a corresponding wild type or codon optimized phycobiliprotein. The determination of sequence identity between two sequences (e.g., between a native sequence and a functional analog) can be accomplished using any alignment tool, including for example, that disclosed in Tatusova et al., *Blast 2 sequences—a new tool for comparing protein and nucleotide sequences, FEMS Microbiol Lett.* 174:247-250 (1999).

In some embodiments, the corresponding wild type or codon optimized phycobiliprotein nucleic acid sequence encodes a phycocyanin or a subunit or a fragment thereof. In some embodiments, the corresponding wild type or codon optimized phycobiliprotein nucleic acid sequence encodes an allophycocyanin or a subunit or fragment thereof. In some embodiments, the corresponding wild type or codon optimized phycobiliprotein nucleic acid sequence encodes a phycoerythrin or a subunit or fragment thereof. In some embodiments, the modified thermostable phycobiliprotein is functional. Such activity can be measured using any appropriate assay, including those described herein.

In some embodiments, the nucleic acid sequence encoding a phycobiliprotein of the present disclosure is inserted into an expression vector. A vector used in the methods can be a plasmid, bacteriophage, or a viral vector into which a nucleic acid sequence encoding the phycobiliprotein can be inserted or cloned. A vector may comprise one or more specific sequences that allow the vector to be maintained extrachromosomally. A vector may comprise one or more specific sequences that allow overexpression of the phycobiliprotein. A vector may comprise one or more specific sequences that allow recombination into a particular, desired site of the *Spirulina*'s chromosome. These specific sequences may be homologous to sequences present in the wild-type *Spirulina*. A vector system can comprise a single vector or plasmid, two or more vectors or plasmids, some of which increase the efficiency of targeted mutagenesis, or a transposition. The choice of the vector will typically depend on the compatibility of the vector with the *Spirulina* cell into which the vector is to be introduced. The vector can include a reporter gene, such as a green fluorescent protein (GFP), which can be either fused in frame to one or more of the encoded phycobiliproteins, or expressed separately. The vector can also include a positive selection marker such as an antibiotic resistance gene that can be used for selection of suitable transformants. The vector can also include a negative selection marker such as the type II thioesterase (tesA) gene or the *Bacillus subtilis* structural gene (sacB). Use of a reporter or marker allows for identification of those cells that have been successfully transformed with the vector.

In some embodiments, the vector contains a nucleic acid sequence encoding a codon-optimized phycocyanin. In some embodiments, vector contains a nucleic acid sequence encoding the codon-optimized phycocyanin is SEQ ID NO: 1, SEQ ID NO: 3, SEQ ID NO: 6, SEQ ID NO: 8, SEQ ID NO: 14, SEQ ID NO: 16, SEQ ID NO: 19, or a combination thereof. In some embodiments, the vector contains a nucleic acid sequence encoding the amino acid sequence of SEQ ID NO: 2, SEQ ID NO: 4, SEQ ID NO: 7, SEQ ID NO: 9, SEQ ID NO: 12, SEQ ID NO: 15, SEQ ID NO: 15, SEQ ID NO: 17, SEQ ID NO: 20, or a combination thereof. In some embodiments, the vector contains a nucleic acid sequence at least about 80% identical to SEQ ID NO: 1, SEQ ID NO: 3, SEQ ID NO: 6, SEQ ID NO: 8, SEQ ID NO: 14, SEQ ID NO: 16, SEQ ID NO: 19, or a combination thereof. In some embodiments, the vector contains a nucleic acid sequence encoding an amino acid sequence at least 80% identical to SEQ ID NO: 2, SEQ ID NO: 4, SEQ ID NO: 7, SEQ ID NO: 9, SEQ ID NO: 12, SEQ ID NO: 15, SEQ ID NO: 15, SEQ ID NO: 17, SEQ ID NO: 20, or a combination thereof. In some embodiments, the vector comprises the sequence of SEQ ID NO: 5, SEQ ID NO: 10, SEQ ID NO: 13, SEQ ID NO: 18, or SEQ ID NO: 21. In some embodiments, the vector comprises a nucleic acid sequence that is at least 80% identical to SEQ ID NO: 5, SEQ ID NO: 10, SEQ ID NO: 13, SEQ ID NO: 18, or SEQ ID NO: 21.

In some embodiments, the vector contains a nucleic acid encoding an allophycocyanin. In some embodiments, the vector contains a nucleic acid sequence encoding a codon optimized allophycocyanin. In some embodiments, the allophycocyanin is further modified to replace one or more amino acid residues with cysteine. In some embodiments, the vector contains a nucleic acid sequence contains a nucleic acid sequence comprising SEQ ID NO: 22, SEQ ID NO: 24, SEQ ID NO: 27, SEQ ID NO: 29, or a combination thereof. In some embodiments, the vector contains a nucleic acid sequence encoding the amino acid sequence of SEQ ID NO: 23, SEQ ID NO: 25, SEQ ID NO: 28, SEQ ID NO: 30, or a combination thereof. In some embodiments, the vector comprises SEQ ID NO: 18. In some embodiments, the vector contains a nucleic acid sequence comprising a sequence at least 80% identical to SEQ ID NO: 22, SEQ ID NO: 24, SEQ ID NO: 27, SEQ ID NO: 29, or a combination thereof. In some embodiments, the vector contains a nucleic acid sequence encoding an amino acid sequence at least 80% identical to SEQ ID NO: 23, SEQ ID NO: 25, SEQ ID NO: 28, SEQ ID NO: 30, or a combination thereof. In some embodiments, the vector comprises a nucleic acid sequence at least 80% identical to SEQ ID NO: 18.

Methods of Making Recombinant *Spirulina* Cells

Any appropriate means for transforming *Spirulina* may be used in the present disclosure. Exemplary methods for transforming *Spirulina* to express a heterologous protein are described in U.S. Pat. No. 10,131,870, which is incorporated by reference herein in its entirety.

In some embodiments, methods of making a thermostable phycobiliprotein comprise introducing an expression vector having a nucleic acid sequence encoding the thermostable phycobiliprotein into a *Spirulina* cell. In some embodiments, the vector is not integrated into the *Spirulina* genome. In some embodiments, the vector is a high copy or a high expression vector. In some embodiments the nucleic acid sequence encoding the thermostable phycobiliprotein is under the control of a strong promoter. In some embodiments the nucleic acid sequence encoding the thermostable phycobiliprotein is under the control of a constitutive promoter. In some embodiments the nucleic acid sequence encoding the thermostable phycobiliprotein is under the control of an inducible promoter. In some embodiments, the promoter includes, but is not limited to, a phycocyanin promoter, an allophycocyanin promoter, a phycoerythrin promoter, the $P_{apcA}$, the $P_{psaL}$, or the $P_{atpI}$ promoter.

In some embodiments, methods of making a thermostable phycobiliprotein comprise introducing a vector having homology arms and a nucleic acid sequence encoding thermostable phycobiliprotein into a *Spirulina* cell. Upon homologous recombination, the nucleic acid sequence encoding the thermostable phycobiliprotein is integrated into the *Spirulina* genome.

In some embodiments, the vector having a polynucleotide encoding the thermostable phycobiliprotein does not contain homology arms to integrate into the *Spirulina* genome, but instead remains extrachromosomal.

In some embodiments, a vector having a nucleic acid sequence encoding the thermostable phycobiliprotein can be introduced via natural competence into the *Spirulina* cells. In some embodiments, a vector having a nucleic acid sequence encoding the thermostable phycobiliprotein can be introduced into *Spirulina* using electroporation. The electroporation is preferably carried out in the presence of an appropriate osmotic stabilizer.

Prior to introduction of the vector into *Spirulina*, *Spirulina* may be cultured in any suitable media for growth of cyanobacteria such as SOT medium. SOT medium includes $NaHCO_3$ 1.68 g, $K_2HPO_4$ 50 mg, $NaNO_3$ 250 mg, $K_2SO_4$ 100 mg, NaCl 100 mg, $MgSO_4.7H_2O$, 20 mg, $CaCl_2.2H_2O$ 4 mg, $FeSO_4.7H_2O$ 1 mg, $Na_2EDTA.2H_2O$ 8 mg, A5 solution 0.1 mL, and distilled water 99.9 mL. A5 solution includes $H_3BO_3$ 286 mg, $MnSO_4.5H_2O$) 217 mg, $ZnSO_4$. $7H_2O$ 22.2 mg, $CuSO_4.5H_2O$ 7.9 mg, $Na_2MoO_4.2H_2O$ 2.1 mg, and distilled water 100 mL. Cultivation may occur with shaking (e.g., 100-300 rpm) at a temperature higher than room temperature (e.g. 25-37° C.) and under continuous illumination (e.g. 20-2,000, 50-500, or 100-200 µmol photon $m^{-2}$ $s^{-1}$). The growing cells may be harvested when the optical density at 750 nm reaches a predetermined threshold (e.g., $OD_{750}$ of 0.3-2.0, 0.5-1.0, or 0.6-0.8). A volume of the harvested cells may be concentrated by centrifugation then resuspended in a solution of pH balancer and salt. The pH balancer may be any suitable buffer that maintains viability of *Spirulina* while keeping pH of the media between 6 and 9 pH, between 6.5 and 8.5 pH, or between 7 and 8 pH. Suitable pH balancers include HEPES, HEPES-NaOH, sodium or potassium phosphate buffer, and TES. The salt solution may be NaCl at a concentration of between 50 mM and 500 mM, between 100 mM and 400 mM, or between 200 mM and 300 mM. In an embodiment between 1-50 mL of 1-100 mM pH balance may be used to neutralize the pH.

Cells collected by centrifugation may be washed with an osmotic stabilizer and optionally a salt solution (e.g. 1-50 mL of 0.1-100 mM NaCl). Any amount of the culture may be concentrated by centrifugation. In an embodiment between 5-500 mL of the culture may be centrifuged. The osmotic stabilizer may be any type of osmotic balancer that stabilizes cell integrity of *Spirulina* during electroporation. In an embodiment, the osmotic stabilizer may be a sugar (e.g. w/v 0.1-25%) such as glucose or sucrose. In an embodiment the osmotic stabilizer may be a simple polyol (e.g. v/v 1-25%) including glycerine, glycerin, or glycerol. In an embodiment the osmotic stabilizer may be a polyether including (e.g. w/v 0.1-20%) polyethylene glycol (PEG), poly(oxyethylene), or poly(ethylene oxide) (PEO). The PEG or PEO may have any molecular weight from 200 to 10,000, from 1000 to 6000, or from 2000 to 4000. In an embodiment the pH balancer or buffer may be used instead of or in addition to the osmotic stabilizer.

A vector having a nucleic acid sequence encoding thermostable phycobiliprotein can be introduced into *Spirulina* cells that are cultured and washed with an osmotic stabilizer as described above.

Electroporation can be used to introduce the vector. Electroporation may be performed in a 0.1-, 0.2- or 0.4-cm electroporation cuvette at between 0.6 and 10 kV/cm, between 2.5 and 6.5 kV/cm, or between 4.0 and 5.0 kV/cm; between 1 and 100 µF, between 30 and 70 µF, or between 45 and 55 µF; and between 10 and 500 mΩ, between 50 and 250 mΩ, or between 90 and 110 mΩ. In some embodiments, electroporation may be performed at 4.5 kV/cm, 50 µf, and 100 mΩ.

Following electroporation the cells may be grown in the presence of one or more antibiotics selected based on resistance conferred through successful transformation with the plasmid. Post-electroporation culturing may be performed at reduced illumination levels (e.g. 5-500, 10-100, or 30-60 mol photon $m^{-2} s^{-1}$). The culturing may also be performed with shaking (e.g. 100-300 rpm). The level of antibiotics in the media may be between 5 and 100 µg/mL. Post-electroporation culturing may be continued for 1-5 days or longer. Successful transformants identified by antibiotic resistance may be selected over a time course of 1 week to 1 month on plates or in 5-100 mL of SOT medium supplemented with 0.1-2.0 µg of appropriate antibiotics.

A vector used in the methods can be a plasmid, bacteriophage, or a viral vector into which a nucleic acid sequence encoding the thermostable phycobiliprotein can be inserted or cloned. In some embodiments, the vector comprises a nucleic acid sequence encoding one or more subunits of a phycobiliprotein as disclosed herein.

A vector may comprise promoters that drive expression and/or any other sequences required for efficient expression of the thermostable phycobiliprotein. A vector may comprise one or more specific sequences that allow recombination into a particular, desired site of the *Spirulina*'s chromosome. These specific sequences may be homologous to sequences present in the wild-type *Spirulina*. A vector system can comprise a single vector or plasmid, two or more vectors or plasmids, some of which increase the efficiency of targeted mutagenesis, or a transposition. The choice of the vector will typically depend on the compatibility of the vector with the *Spirulina* cell into which the vector is to be introduced. The vector can include a reporter gene, such as a green fluorescent protein (GFP), which can be either fused in frame to one or more of the phycobiliproteins, or expressed separately. The vector can also include a positive selection marker such as an antibiotic resistance gene that can be used for selection of suitable transformants. The vector can also include a negative selection marker such as the type II thioesterase (tesA) gene or the *Bacillus subtilis* structural gene (sacB). Use of a reporter or marker allows for identification of those cells that have been successfully transformed with the vector.

In some embodiments, the vector includes one or two homology arms that are homologous to DNA sequences of the *Spirulina* genome that are adjacent to the targeted locus. The sequence of the homology arms can be partially or fully complementary to the regions of *Spirulina* genome adjacent to the targeted locus.

The homology arms can be of any length that allows for site-specific homologous recombination. A homology arm may be any length between about 2000 bp and 500 bp. For example, a homology arm may be about 2000 bp, about 1500 bp, about 1000 bp, or about 500 bp. In some embodiments having two homology arms, the homology arms may be the same or different length. Thus, each of the two homology arms may be any length between about 2000 bp and 500 bp. For example, each of the two homology arms may be about 2000 bp, about 1500 bp, about 1000 bp, or about 500 bp.

A portion of the vector adjacent to one homology arm or flanked by two homology arms modifies the targeted locus in the *Spirulina* genome by homologous recombination. The modification may change a length of the targeted locus including a deletion of nucleotides or addition of nucleotides. The addition or deletion may be of any length. The modification may also change a sequence of the nucleotides in the targeted locus without changing the length. The targeted locus may be any portion of the *Spirulina* genome including coding regions, non-coding regions, and regulatory sequences.

Recombinant *Spirulina* Cells

The present disclosure provides recombinant *Spirulina* cells containing or expressing the thermostable phycobiliproteins described herein. In some embodiments, recombinant *Spirulina* cell contains a thermostable phycobiliprotein. In some embodiments, the thermostable phycobiliprotein is a phycocyanin. In some embodiments, the thermostable phycocyanin is obtained from a thermophilic organism. In some embodiments, the thermophilic organism is *T. vulcanus*. In some embodiments, the phycocyanin is a codon optimized phycocyanin. In some embodiments, the phycocyanin is codon optimized for expression in *Spirulina*. In some embodiments, the phycocyanin is codon optimized for expression in *A. platensis*. In some embodiments, the phycocyanin is further modified to replace one or more amino acid residues with cysteine. In some embodiments, the phycocyanin contains a codon-optimized cpcA subunit containing one or more of the following replacements: L5C/I5C, A40C, and/or A146C or a combination thereof. In some embodiments, the phycocyanin contains a codon-optimized cpcB subunit containing a D3C replacement.

In some embodiments, the nucleic acid sequence encoding the codon-optimized phycocyanin is SEQ ID NO: 1, SEQ ID NO: 3, SEQ ID NO: 6, SEQ ID NO: 8, SEQ ID NO: 14, SEQ ID NO: 16, SEQ ID NO: 19, or a combination thereof. In some embodiments, the polynucleotide sequence encoding the codon-optimized phycocyanin is expressed from the plasmid of SEQ ID NO: 5, SEQ ID NO: 10, SEQ ID NO: 13, SEQ ID NO: 18, or SEQ ID NO: 21. In some embodiments, the thermostable phycocyanin comprises the amino acid sequence of SEQ ID NO: 2, SEQ ID NO: 4, SEQ ID NO: 7, SEQ ID NO: 9, SEQ ID NO: 12, SEQ ID NO: 15, SEQ ID NO: 15, SEQ ID NO: 17, SEQ ID NO: 20, or a combination thereof. In some embodiments, the nucleic acid sequence encoding the codon-optimized phycocyanin is at least about 80% identical to SEQ ID NO: 1, SEQ ID NO: 3, SEQ ID NO: 6, SEQ ID NO: 8, SEQ ID NO: 14, SEQ ID NO: 16, SEQ ID NO: 19, or a combination thereof. In some embodiments, the polynucleotide sequence encoding the codon-optimized phycocyanin is expressed from a plasmid at least 80% identical to SEQ ID NO: 5, SEQ ID NO: 10, SEQ ID NO: 13, SEQ ID NO: 18, or SEQ ID NO: 21. In some embodiments, the thermostable phycocyanin comprises an amino acid sequence at least 80% identical to SEQ ID NO: 2, SEQ ID NO: 4, SEQ ID NO: 7, SEQ ID NO: 9, SEQ ID NO: 12, SEQ ID NO: 15, SEQ ID NO: 15, SEQ ID NO: 17, SEQ ID NO: 20, or a combination thereof.

In some embodiments, the thermostable phycobiliprotein is an allophycocyanin. In some embodiments, the allophycocyanin is obtained from a thermophilic organism. In some embodiments, the thermophilic organism is *T. vulcanus*. In some embodiments, the allophycocyanin is a codon optimized allophycocyanin. In some embodiments, the allophycocyanin is codon optimized for expression in *Spirulina*. In some embodiments, the allophycocyanin is codon optimized for expression in *A. platensis*. In some embodiments, the allophycocyanin is further modified to replace one or more amino acid residues with cysteine. In some embodiments, nucleic acid sequence expressing the allophycocyanin is SEQ ID NO: 22, SEQ ID NO: 24, SEQ ID NO: 27, SEQ ID NO: 29, or a combination thereof. In some embodiments, the allophycocyanin comprises the amino acid sequence of SEQ ID NO: 23, SEQ ID NO: 25, SEQ ID NO: 28, SEQ ID NO: 30, or a combination thereof. In some embodiments, the allophycocyanin is expressed from the plasmid of SEQ ID NO: 18. In some embodiments, nucleic acid sequence expressing the allophycocyanin is at least 80% identical to SEQ ID NO: 22, SEQ ID NO: 24, SEQ ID NO: 27, SEQ ID NO: 29, or a combination thereof. In some embodiments, the allophycocyanin comprises an amino acid sequence at least 80% identical to SEQ ID NO: 23, SEQ ID NO: 25, SEQ ID NO: 28, SEQ ID NO: 30, or a combination thereof. In some embodiments, the allophycocyanin is expressed from a plasmid at least 80% identical to SEQ ID NO: 18.

In some embodiments, the *Spirulina* cell contains a plasmid, vector, or sequence encoding a thermostable phycobiliprotein. In some embodiments, the *Spirulina* cell contains the nucleic acid sequence of SEQ ID NO: 1, SEQ ID NO: 3, SEQ ID NO: 6, SEQ ID NO: 8, SEQ ID NO: 14, SEQ ID NO: 16, SEQ ID NO: 19, SEQ ID NO: 22, SEQ ID NO: 24, SEQ ID NO: 27, SEQ ID NO: 29, or a combination thereof. In some embodiments, the *Spirulina* cell contains a nucleic acid sequence encoding one or more phycobiliproteins having the amino acid sequence of SEQ ID NO: 2, SEQ ID NO: 4, SEQ ID NO: 7, SEQ ID NO: 9, SEQ ID NO: 12, SEQ ID NO: 15, SEQ ID NO: 17, SEQ ID NO: 20, SEQ ID NO: 23, SEQ ID NO: 25, SEQ ID NO: 28, SEQ ID NO: 30, or a combination thereof. In some embodiments, the *Spirulina* cell contains a plasmid or fragment thereof of the plasmid of SEQ ID NO: 5, SEQ ID NO: 10, SEQ ID NO: 13, SEQ ID NO: 18, or SEQ ID NO: 21.

In some embodiments, the recombinant *Spirulina* cell is disclosed in Table 1.

TABLE 1

Strains

| Strain | Phycocyanin variant | Description | Plasmid SEQ ID NO: |
|---|---|---|---|
| SP3 | *A. platensis* cpcBA | Wild-type *A. platensis* strain UTEX LB1926. | |
| SP84 | *A. platensis* cpcBA | Strain that overexpresses *A. platensis* cpcBA. | |
| SP171 | *T. vulcanus* cpcBA | Strain that overexpresses *T. vulcanus* cpcBA | |
| SP708 | *T. vulcanus* cpcB D3C cpcA I5C A40C A146C | *T. vulcanus* phycocyanin that forms an intermolecular disulfide bond between CpcB and CpcA in addition to an intramolecular disulfide bond within CpcA was introduced at a second locus; native cpcBA is still expressed in the cell | 13 |
| SP709 | *T. vulcanus* cpcB D3C cpcA I5C | *T. vulcanus* phycocyanin that forms an intermolecular disulfide bond between CpcB and CpcA was introduced at a second locus; native cpcBA is still expressed in the cell | 10 |
| SP710 | *T. vulcanus* cpcBA A40C A146C | *T. vulcanus* phycocyanin that forms an intramolecular disulfide bond in CpcA was introduced at a second locus; native cpcBA is still expressed in the cell | 5 |
| SP713 | *A. platensis* cpcB D3C cpcA L5C A40C A146C | *A. platensis* phycocyanin that forms an intermolecular disulfide bond between CpcB and CpcA in addition to an intramolecular disulfide bond within CpcA was introduced at a second locus; native cpcBA is still expressed in the cell | |
| SP714 | *A. platensis* cpcB D3C cpcA L5C | *A. platensis* phycocyanin that forms an intermolecular disulfide bond between CpcB and CpcA was introduced at a second locus; native cpcBA is still expressed in the cell | |
| SP715 | *A. platensis* cpcBA A40C A146C | *A. platensis* phycocyanin that forms an intramolecular disulfide bond in CpcA was introduced in at a second locus; native cpcBA is still expressed in the cell | 18 |
| SP751 | *T. vulcanus* cpcBA | Genome replacement of native cpcBA with *T. vulcanus* cpcBA. Aada is inserted in between cpcA and cpcH and a the promoter from psaL is used to drive expression of genes downstream of cpcH. | 21 |
| SP752 | *A. platensis* cpcBA | Genome replacement of native cpcBA locus. Aada is inserted in between cpcA and cpcH and a the promoter from psaL is used to drive expression of genes downstream of cpcH. | |
| SP705 | *T. vulcanus* apcAB | Overexpression of *T. vulcanus* apcAB using a DNA sequence that was codon optimized for expression in *A. platensis*, an intergenic region from *A. platensis* strain NIES-39, and using the Pcpc600 promoter to drive expression. Expression constructs were integrated; native apcAB is still expressed in the cell. | 26 |
| SP907 | *T. vulcanus* apcAB | Overexpression of *T. vulcanus* apcAB using the intergenic region from *A. platensis* strain NIES-39 and using the Pcpc290 promoter to drive expression. Expression constructs were integrated; native apcAB is still expressed in the cell. | 31 |
| SP908 | *T. vulcanus* apcAB | Overexpression of *T. vulcanus* apcAB using a DNA sequence that was codon optimized for expression in *A. platensis*, an intergenic region from *A. platensis* strain NIES-39, and using the Pcpc290 promoter to drive expression. Expression constructs were integrated; native apcAB is still expressed in the cell. | 34 |

In some embodiments, the recombinant *Spirulina* cell contains one or more integrated phycobiliproteins of the disclosure. In some embodiments, the recombinant *Spirulina* cell contains one or more phycobiliproteins of the disclosure on at least one extrachromomal plasmid. In some embodiments, the recombinant *Spirulina* cell contains both one or more integrated phycobiliproteins of the disclosure and at least one extrachromosomal plasmid comprising one or more phycobiliproteins of the disclosure.

In some embodiments, the recombinant *Spirulina* cell retains all of its endogenous genes encoding one or more phycobiliproteins. In some embodiments, the recombinant *Spirulina* cell retains some of its endogenous genes encoding one or more phycobiliproteins. In some embodiments, the recombinant *Spirulina* cell retains none of its endogenous genes encoding a phycobiliprotein.

In some embodiments, the recombinant *Spirulina* cell is selected from the list including, but not limited to, *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri Stizenberger, A. jennerif. purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. *non-constricta, A. platensis* f. *granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima,* and *A. versicolor.*

Production and Analysis of Thermostable Phycobiliprotein

The thermostable phycobiliproteins of the present disclosure may be produced and expressed using any appropriate method. In some embodiments, the recombinant *Spirulina* cells of the disclosure are cultured and grown under conditions that will allow expression of the introduced phycobiliprotein. Once the cells have reached the proper growth/concentration, they can be lysed and collected (e.g. through centrifugation).

For example, the recombinant *Spirulina* cells may be lysed by harvesting the cells using a buffer, and pelleting and resuspending in the buffer. In some embodiments, the buffer is sodium phosphate at a concentration between 10 and 100 µM at a physiological pH. In some embodiments, the pH is about 6. The recombinant *Spirulina* cells may be incubated in the dark with shaking at about 35° C. for at least four hours. The cells can then be centrifuged at 4° C. to remove insoluble material. The supernatant is centrifuged to remove soluble material.

The recombinantly-produced phycobiliprotein may be analyzed individually, or as part of the cell lysate (e.g. using a thermostability assay). Any appropriate thermostability assay may be used. For example, after bringing the cell lysates to a protein concentration of 1 mg/mL in 100 mM sodium phosphate, pH 6, heat is applied to the lysate for the desired time. After removal from heat, the lysate samples are placed in an ice water bath to halt treatment. The insoluble material is removed by centrifugation at 4° C., and the absorbance of the soluble fraction at 620 nm and 650 nm is measured.

In some embodiments, the thermostable phycobiliprotein of the present disclosure is more temperature and acid resistant than its corresponding wild type or codon-optimized phycobiliprotein. In some embodiments, the thermostability of the phycobiliprotein is assayed as described above. In some embodiments, the thermostable phycobiliprotein is stable at temperatures greater than about 45° C. In some embodiments, the thermostable phycobiliprotein is stable at temperatures between about 45° and about 100° C. In some embodiments, the thermostable phycobiliprotein is stable at a temperature of about 45° C., about 50° C., about 55° C., about 60° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., or about 80° C.

In some embodiments, the thermostable phycobiliprotein or lysate of the present disclosure is stable at temperatures greater than about 45° C. for at least 5 seconds. In some embodiments, the thermostable phycobiliprotein or lysate is stable at temperatures between about 45° and about 100° C. for about 5 seconds to about 24 hours. In some embodiments, the thermostable phycobiliprotein or lysate is stable at a temperature of about 45° C., about 50° C., about 55° C., about 60° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., or about 80° C. for about 5 seconds, about 10 seconds, about 15 seconds, about 20 seconds, about 30 seconds, about 40 seconds, about 50 seconds, about 1 minute, about 5 minutes, about 10 minutes, about 15 minutes, about 20 minutes, about 30 minutes, about 40 minutes, about 45 minutes, about 50 minutes, about 60 minutes, about 2 hours, about 4 hours, about 6 hours, about 8 hours, about 10 hours, about 12 hours, about 14 hours, about 16 hours, about 18 hours, about 20 hours, about 22 hours, or about 24 hours. In some embodiments, the thermostable phycobiliprotein or lysate is stable at 65° C. for about 30 minutes. In some embodiments, the thermostable phycobiliprotein or lysate is stable at 65° C. for about 10 minutes. In some embodiments, the thermostable phycobiliprotein or lysate is stable at 65° C. for about 30 minutes. In some embodiments, the thermostable phycobiliprotein or lysate is stable at 70° C. for about 10 minutes. In some embodiments, the thermostable phycobiliprotein or lysate is stable at 70° C. for about 30 minutes. In some embodiments, the thermostable phycobiliprotein or lysate is stable at 75° C. for about 10 minutes. In some embodiments, the thermostable phycobiliprotein or lysate is stable at 75° C. for about 30 minutes.

In some embodiments, the thermostable phycobiliprotein or lysate of the present disclosure is about 1-fold to about 100-fold more temperature stable than the corresponding wild type or codon-optimized phycobiliprotein. In some embodiments, the thermostable phycobiliprotein or lysate is about 2-fold, about 3-fold, about 4-fold, about 5-fold, about 10-fold, about 20-fold, about 30-fold, about 40-fold, about 50-fold, about 50-fold, about 60-fold, about 70-fold, about 80-fold, about 90-fold, or about 100-fold greater than the corresponding wild type or codon-optimized phycobiliprotein. In some embodiments, the thermostable phycobiliprotein or lysate is about 78 fold more temperature sensitive than the corresponding wild type or codon optimized phycobiliprotein.

In some embodiments, the thermostable phycobiliprotein or lysate of the present disclosure is about 1-fold to about 100-fold more temperature stable than the corresponding wild type or codon optimized phycobiliprotein for more than 30 minutes. In some embodiments, the thermostable phycobiliprotein or lysate is about 2-fold, about 3-fold, about 4-fold, about 5-fold, about 10-fold, about 20-fold, about 30-fold, about 40-fold, about 50-fold, about 50-fold, about 60-fold, about 70-fold, about 80-fold, about 90-fold, or about 100-fold more temperature stable than the corresponding wild type or codon-optimized phycobiliprotein for about 5 seconds, about 10 seconds, about 15 seconds, about 20 seconds, about 30 seconds, about 40 seconds, about 50 seconds, about 1 minute, about 5 minutes, about 10 minutes, about 15 minutes, about 20 minutes, about 30 minutes, about 40 minutes, about 45 minutes, about 50 minutes, about 60 minutes, about 2 hours, about 4 hours, about 6 hours, about 8 hours, about 10 hours, about 12 hours, about 14 hours, about 16 hours, about 18 hours, about 20 hours, about 22 hours, or about 24 hours. In some embodiments, the thermostable phycobiliprotein or lysate is about 78-fold more temperature sensitive than the corresponding wild type or codon-optimized phycobiliprotein for about 30 minutes. In some embodiments this phycobiliprotein is thermostable phycocyanin. In some embodiments, this thermostable phycocyanin comprises the A40C and A146C mutations disclosed herein.

In some embodiments, the cell lysate from a recombinant *Spirulina* cell of the present disclosure contains more thermostable phycobiliprotein than a corresponding unmodified *Spirulina* cell (e.g. a cell not transformed with the same thermostable phycobiliprotein or a cell not containing any thermostable phycobiliprotein). In some embodiments, the cell lysate from a recombinant *Spirulina* cell contains a ratio greater than about 1.1:1 thermostable phycobiliprotein to endogenous phycobiliprotein. In some embodiments, the cell lysate from a recombinant *Spirulina* cell contains a ratio of about 1.1:1 to about 1:0 thermostable phycobiliprotein to endogenous phycobiliprotein. In some embodiments, the cell lysate from a recombinant *Spirulina* cell contains a ratio of about 1.1:1, about 1.2:1, about 1:3, about 1.4:1, about 1.5:1, about 1.6:1, about 1.7:1, about 1.8:1, about 1.9:1, about 2:1, about 2.5:1, about 3:1, about 3.5:1, about 4:1, about 4.5:1, about 5:1, about 6:1, about 7:1, about 8:1, about 9:1, or about 10:1. In some embodiments, the phycobiliprotein is overexpressed in the cell.

EXAMPLES

Materials and Methods
Cell Lysis

Cells were harvested and washed into 100 mM sodium phosphate, pH 6, by centrifugation and the cell pellets were frozen at −80° C. The cell pellet is resuspended to 2-10 g/L in 10-100 mM sodium phosphate, pH 6-8 and incubated in the dark, shaking at 150 rpm, at 35° C. for at least 4 hours. The insoluble material was removed by centrifugation at 4° C., 8,000 rpm for 20 min. The collected soluble material was concentrated using Amicon Ultra centrifugal filter units with up to a 10 kDa MWCO to a concentration desired for the downstream assay.

PAGE Analysis

Samples were prepared in Novex Tris-glycine SDS or Novex LDS sample buffer with or without reducing agent. Invitrogen 4-20% Tris-glycine gels run in Novex Tris-glycine SDS running buffer (200 V, 4° C.) was used to resolve the CPC and APC subunits. Bilin-containing proteins were visualized by staining the gels with 20 mM zinc acetate and excitation at 312 nm to fluorescently indicate the presence of bilin-linked proteins. Total protein was visualized by Coomassie stain and image analysis was performed using Fiji.

Thermostability Assay

Protein lysates was brought to a starting concentration of 1 mg/mL in 100 mM sodium phosphate, pH 6. Each protein solution was aliquoted into a PCR tube, 200 µL, for each time-point to be assayed. Heat was applied using a thermalcycler with the heated lid set to a temperature no greater than the temperature applied to the tubes. After samples are treated for the desired time, they are removed from thermalcycler and placed in an ice water bath for at least 15 min to halt the treatment. The insoluble material was removed by centrifugation at 13,000 rpm for 20 min at 4° C. The absorbance of the soluble fraction at 620 and 650 nm was measured and compared to the values observed for the untreated samples.

Example 1: Generation of Thermostable Phycocyanin

Figure 3:
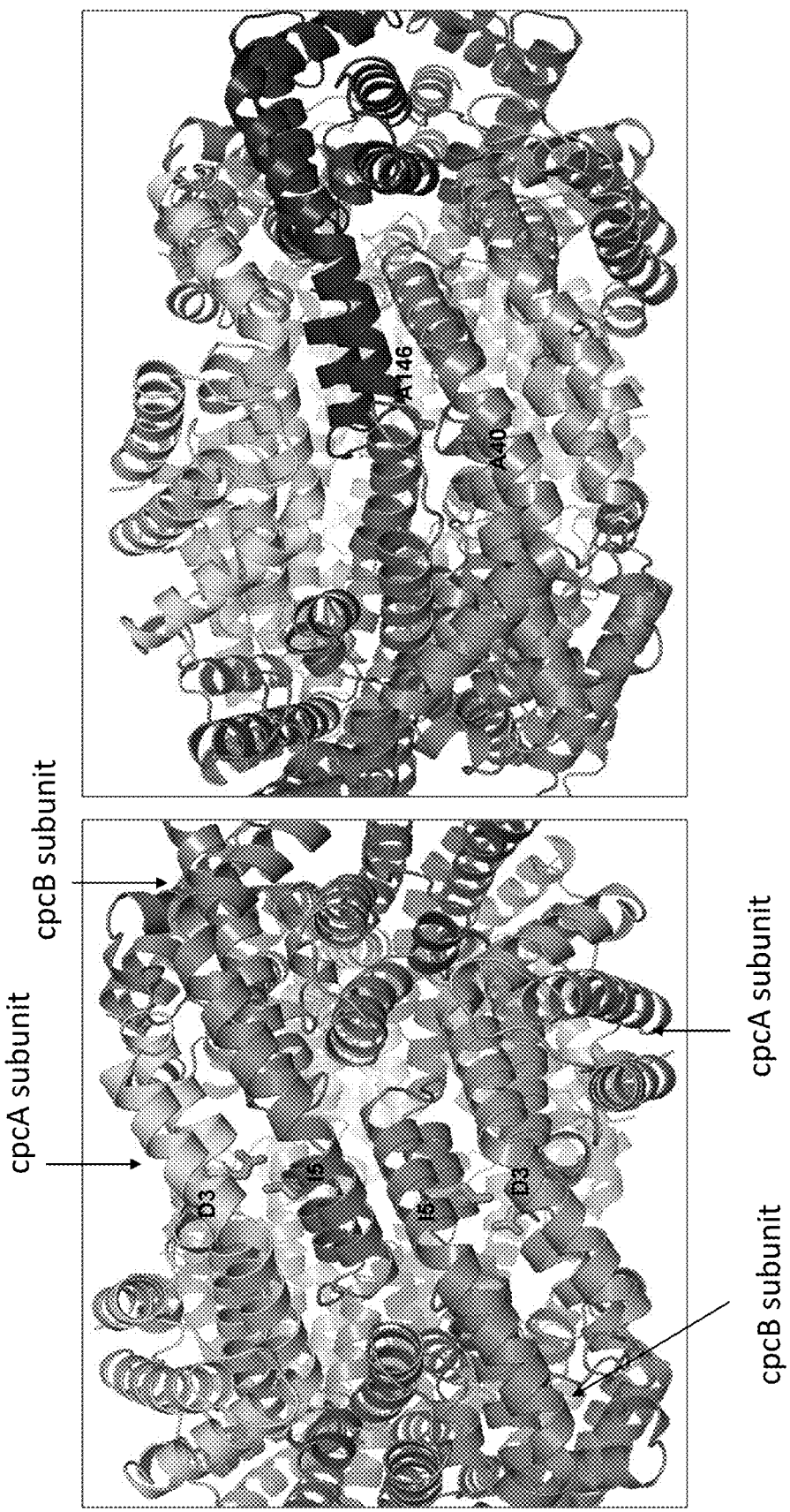

To generate a more thermostable variant of phycocyanin, cysteine residues were introduced into the cpcA and/or cpcB subunit to facilitate formation of stabilizing covalent disulfide bonds within and between the polypeptide chains upon exposure to an oxidative environment (FIG. 3). Amino acid residues were chosen for cysteine replacement based on their angle and distance between each other are similar to the distance and angle of a disulfide bond. Two pairs of cysteine mutations, CpcA A40C A146C to facilitate formation of an intramolecular CpcA disulfide bond and CpcB D3C CpcA I5C to promote formation of an intermolecular disulfide bond, were placed into the *A. platensis* cpcBA and *T. vulcanus* cpcBA sequence either individually or in combination with one another (Table 1, FIG. 3).

Figure 4:
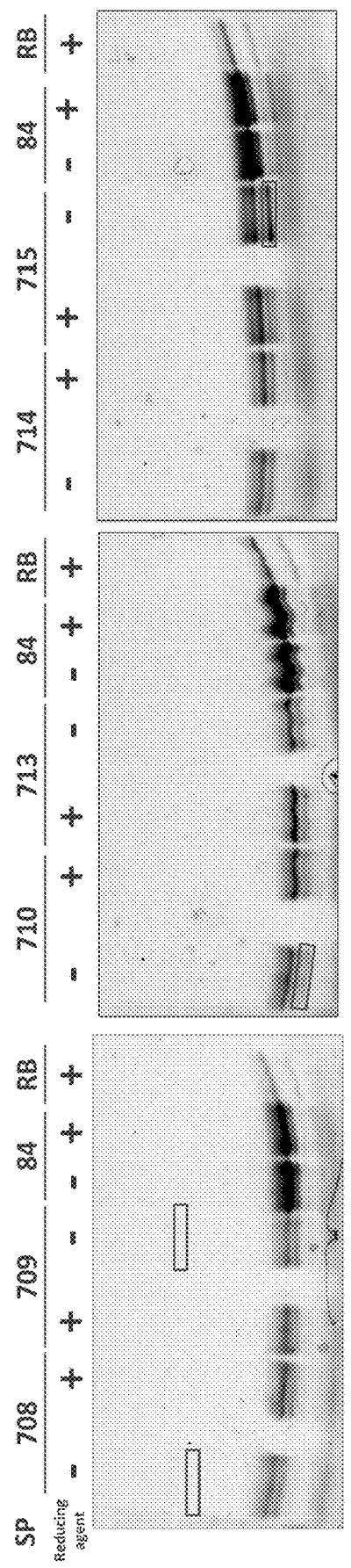
FIG. 4. A sub-population of phycocyanin in SP708, 709, 710, and 715 lysate forms disulfide bonds. The gels show disulfide bond formation assessed for lysates from the indicated *A. platensis* strains. Samples were prepared with and without reducing agent, 50 mM dithiothreitol (DTT), and analyzed by PAGE. Phycocyanin was visualized by staining of the gel with zinc acetate to label the bilin-containing proteins. Disulfide bond containing proteins migrate differently relative to when the bonds are reduced. Bands that appear in the non-reduced samples are indicated by a box.

The presence of disulfide bond reductases in the *Spirulina* cytoplasm result in cysteines remaining in their thiolate state when the proteins are synthesized. The disulfide bond forms upon cell lysis, and the proximity of the introduced cysteines in the folded protein decreases the likelihood that aberrant bonds will form. In order to assess the ability of phycocyanin expressed in strains SP708-715 to form disulfide bonds, protein was extracted from the *A. platensis* strains and analyzed by polyacrylamide gel electrophoresis (PAGE) (FIG. 4). Samples were analyzed after treatment with or without reducing agent with the expectation that polypeptides that form a disulfide bond would migrate differently under these two conditions. The phycocyanin proteins expressed in strains SP708, 709, 710, and 715 are capable of forming disulfide bonds (FIG. 4).

Figure 5A:
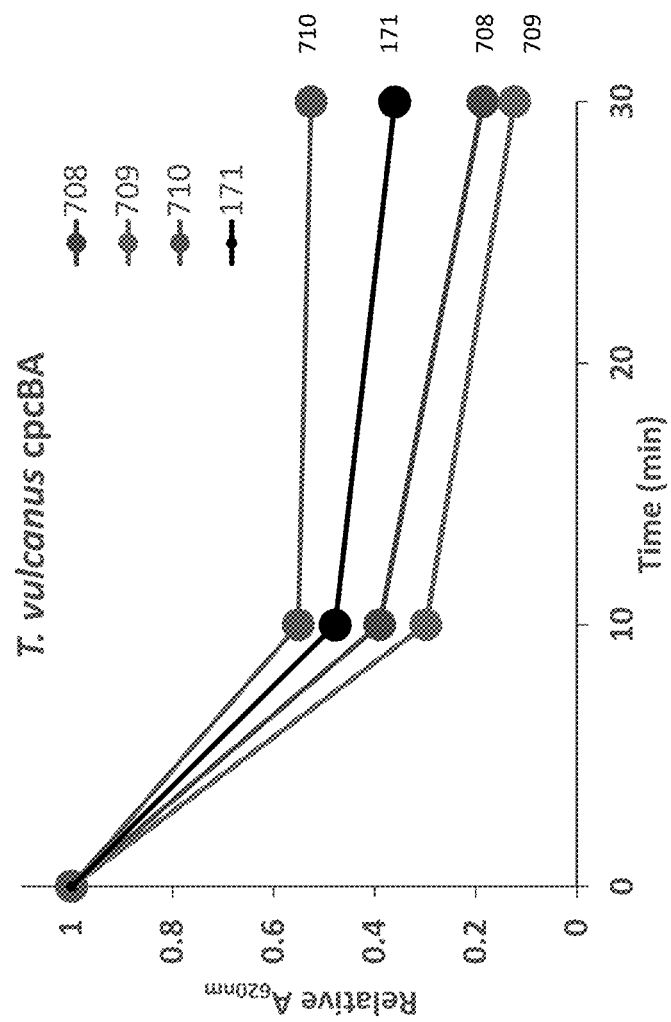
FIG. 5A-B. An intramolecular disulfide bond in CpcA increases the thermostability of phycocyanin. Panel A shows protein lysates of *T. vulcanus* cpcBA; Panel B shows protein lysates of *A. platensis* cpcBA. Protein lysates were extracted and treated at 65° C. for the indicated time-points and the A620 nm of the soluble fraction is reported. SP710 and SP715 were engineered to form a disulfide bond within CpcA of *T. vulcanus* or *A. platensis*, respectively; these strains also contain WT CpcBA expressed from the native locus. SP171 and SP84 are strains that overexpress *T. vulcanus* cpcBA and *A. platensis* cpcBA, respectively.
Figure 5B:
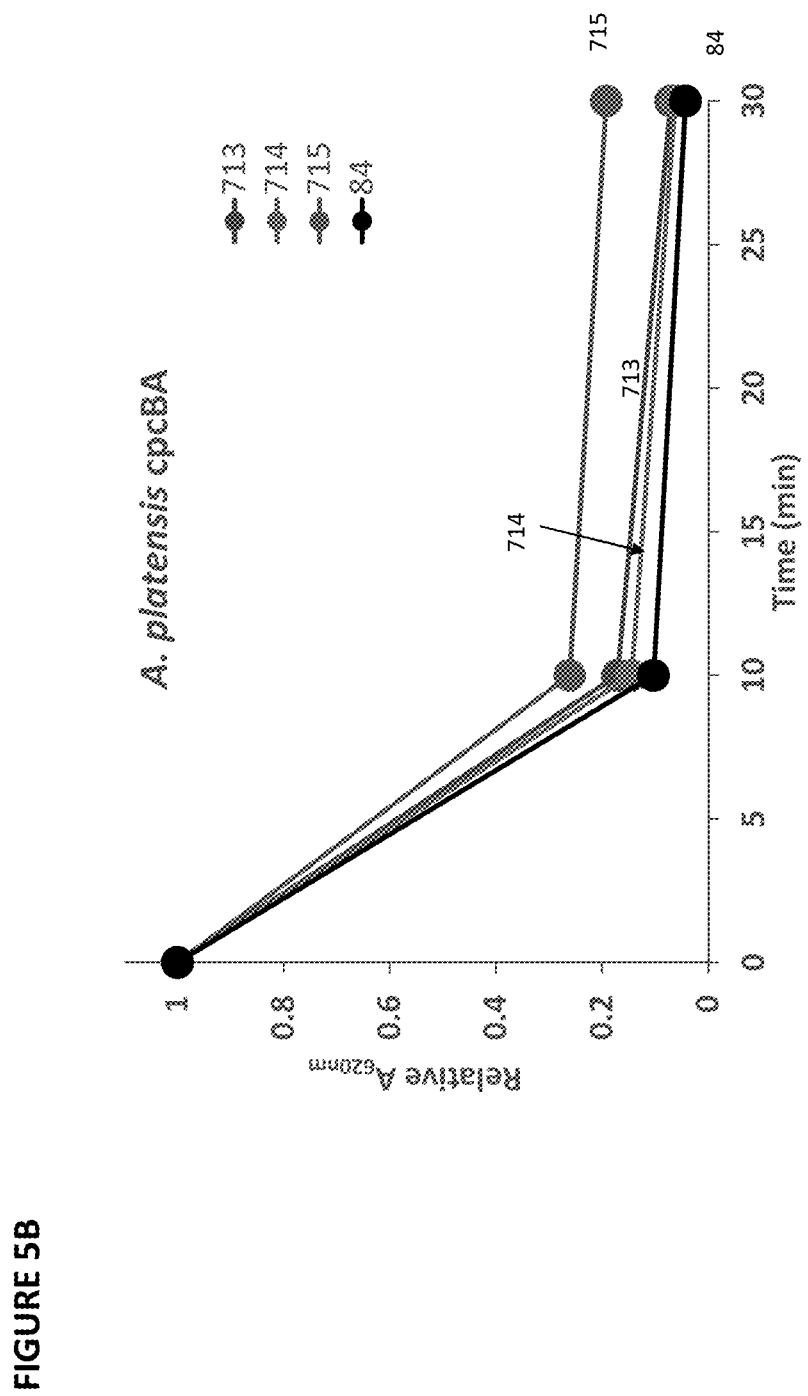
Figure 6:
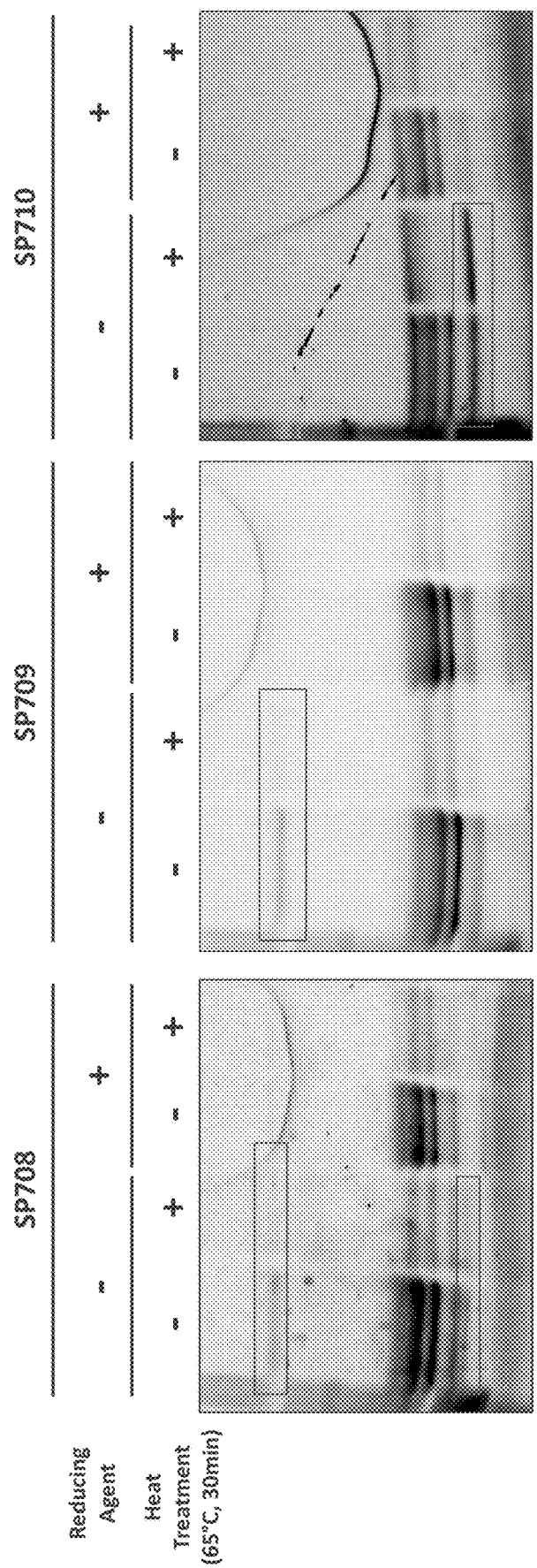
FIG. 6. Disulfide bond containing proteins are enriched in SP710 heat-treated lysate. The soluble fraction of protein lysate from untreated and treated (65° C., 30 min) SP708, 709, and 710 were analyzed by PAGE in the presence or absence of a reducing agent, 50 mM DTT. The disulfide bond containing protein is most enriched in the SP710 lysate. 1.5 µg of CPC in the heat-treated fraction per lane was loaded; an equal volume was used in loading the untreated sample. Phycocyanin is visualized by zinc acetate staining. The boxes indicate the where the disulfide bond containing proteins should migrate.
Figure 7:
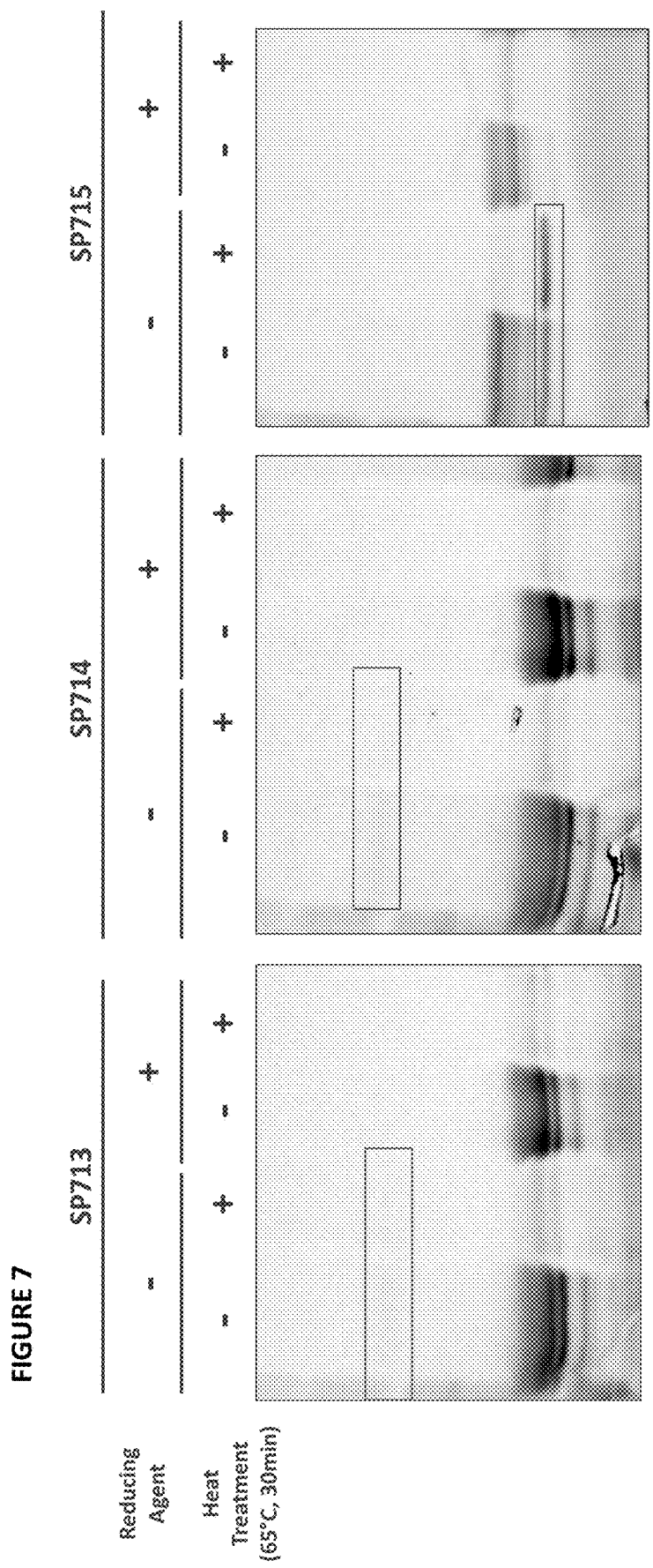
FIG. 7. Disulfide bond containing proteins are enriched in heat-treated SP715 lysate. The soluble fraction of protein lysate from untreated and treated (65° C., 30 min) SP713, 714, and 715 were analyzed by PAGE in the presence or absence of a reducing agent, 50 mM DTT. The disulfide bond containing protein is most enriched in the SP715 lysate. 1.5 µg of CPC in the heat-treated fraction per lane was loaded; an equal volume was used in loading the untreated sample. Phycocyanin is visualized by zinc acetate staining. The boxes indicate the where the disulfide bond containing proteins should migrate.
Figure 8:
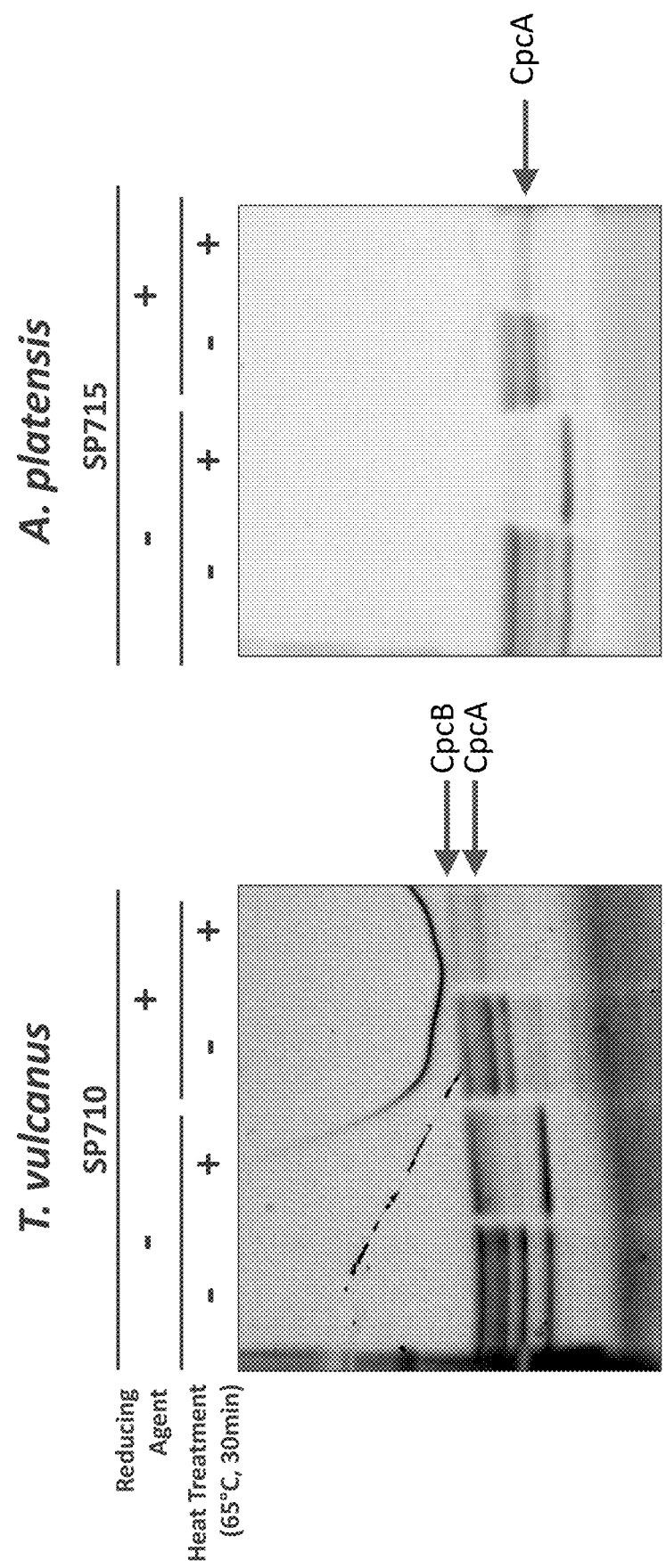
FIG. 8. Heat-stable fraction of SP715 lysate contains only the disulfide bond forming CpcA subunit of phycocyanin, *A. platensis* CpcA A40C A146C. The soluble fraction of protein lysates from untreated and treated (65° C., 30 min) SP710 and 715 were analyzed by PAGE in the presence or absence of a reducing agent, 50 mM DTT. After treatment, SP710 appears to retain equimolar amounts of CpcB and an intramolecular disulfide bond forming CpcA whereas SP715 appears to only retain a disulfide bond forming CpcA. 1.5 µg of CPC in the heat-treated fraction per lane was loaded; an equal volume was used in loading the untreated sample. Phycocyanin was visualized by staining of the gel with zinc acetate.
Figure 9A:
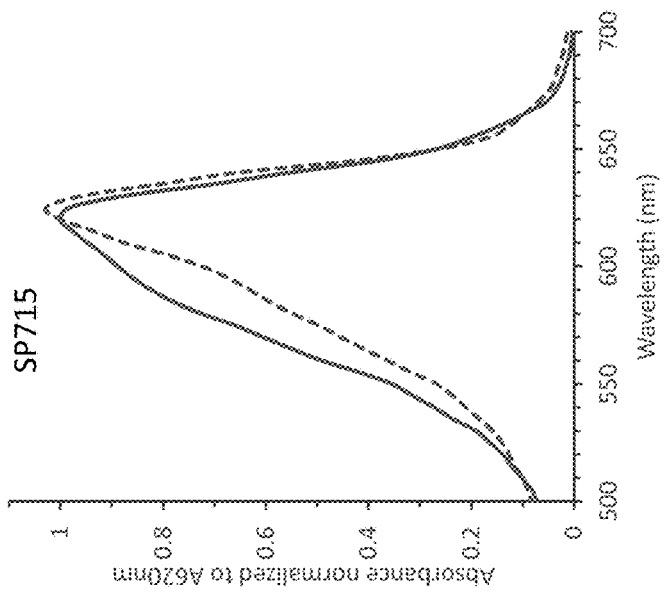
FIG. 9A-C. Absorbance maxima of heat-treated SP715 shifts 5 nm to 625 nm. The absorbance spectra of the soluble fraction of untreated (solid lines) and heat-treated (dashed lines, 65° C., 30 min) protein lysate; the values were normalized to the absorbance at 620 nm. A) SP171 B) SP710 C) SP715.
Figure 9B:
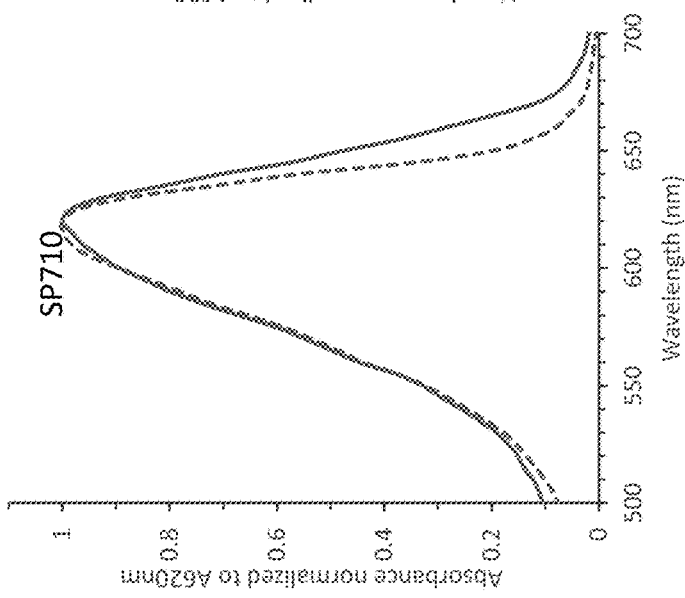
Figure 9C:
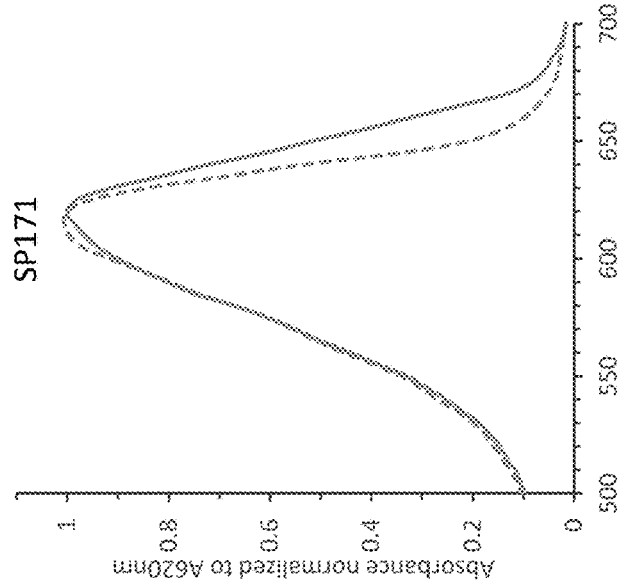

The protein lysate from strains with phycocyanin variants that can form an intramolecular CpcA disulfide bond, SP710 and SP715, exhibits greater thermostability when treated at 65° C. than strains that express the unmodified *T. vulcanus* and *A. platensis* CPC (strains SP171 and SP84 respectively) (FIG. 5)). Strains expressing phycocyanin variants with the CpcA A40C A146C mutations are enriched in the heat stable fraction (FIGS. 6 and 7). In SP715 cell lysate, *A. platensis* CpcA A40C A146C is the only phycocyanin subunit that is heat stable (FIG. 8). The absence CpcB results in a shift of the absorbance spectra of this lysate 5 nm to 625 nm (FIG. 9).

Figures 10A, 10B:
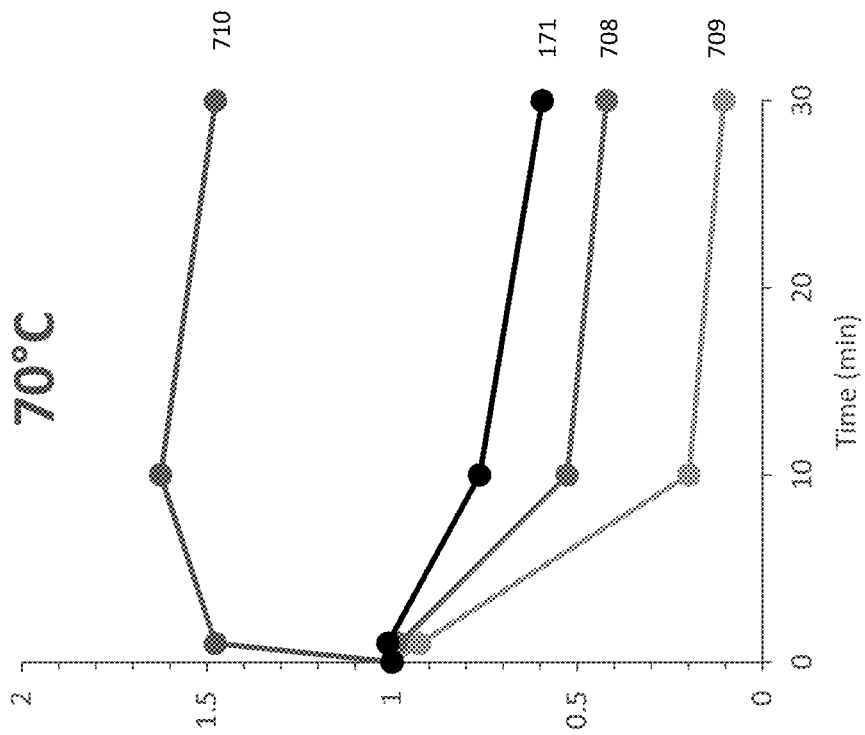
Figure 11:
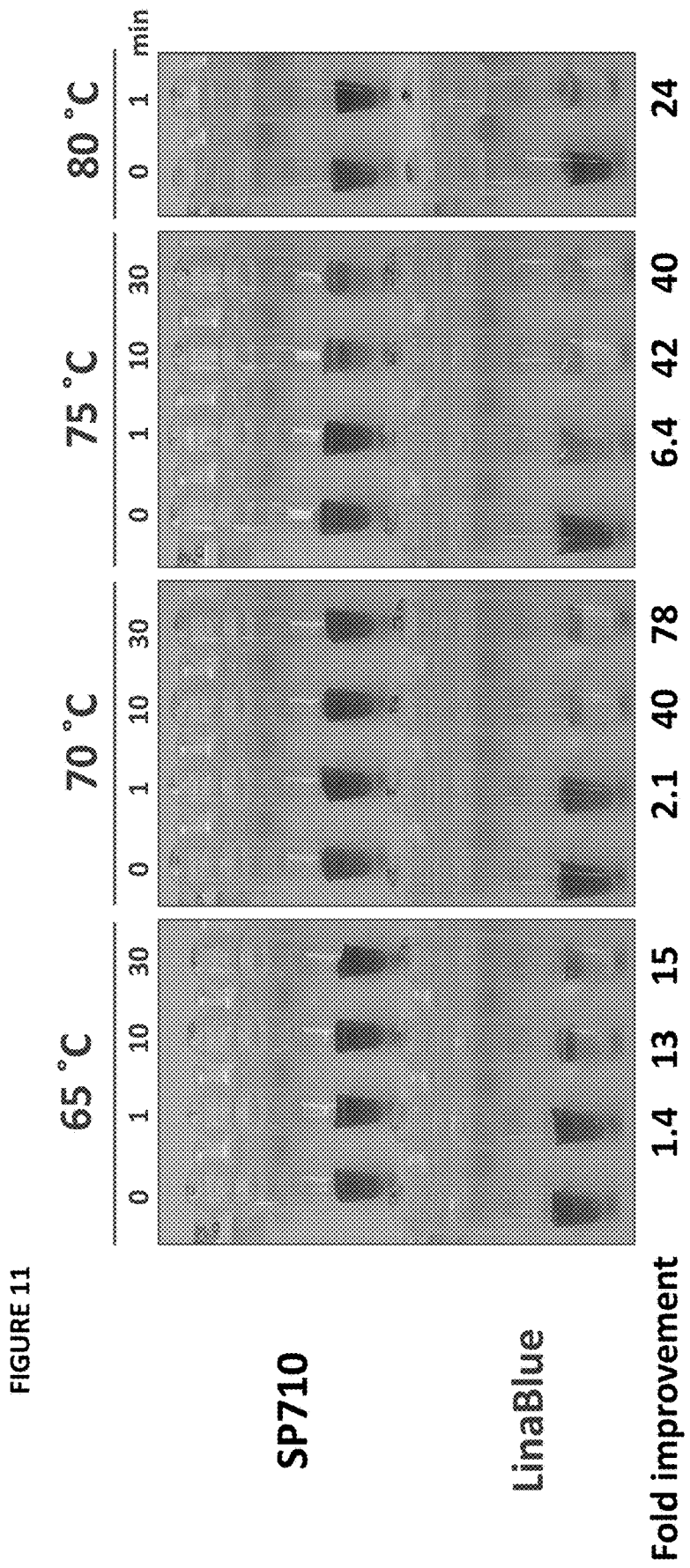
FIG. 11. SP710 heat-purified protein lysate is more stable than LinaBlue at all temperatures tested. *Arthrospira plat-* ensis CpcBA was preferentially removed from SP710 by heat treatment, 65° C., 30 min, and centrifugation to remove the insoluble material. The remaining soluble protein was concentrated to 1 mg/mL and re-assayed for thermostability at 65, 70, 75, and 80° C. and the remaining A620 nm was compared to color retained by LinaBlue treated in the same manner.

Samples were heat-treated at 65° C. for 30 minutes to remove *A. platensis* CPC before the lysates were retested at temperatures from 65 to 80° C. (FIG. 10). The presence of an intramolecular disulfide bond in CpcA drastically enhances thermostability (SP710). Whereas the intermolecular disulfide bond appears to destabilize the CPC as evidenced by the observations that SP708 lysate is less stable than that of the SP171 when tested at 65 and 70° C. (FIG. 10). The most thermostable strain, SP710, was tested against a leading competitor, LinaBlue, and found to outperform it by up to 78-fold (FIG. 11). Future efforts focus on replacing the native CPC with *T. vulcanus* cpcB and cpcA A40C A146C found in SP710 and increasing the amount of expressed protein.

Example 2: Genome Replacement

The presence of *A. platensis* cpcBA expressed at the native genomic locus decreases the yield of the phycocyanin variants that we are trying to express and the thermostability of the protein lysate. *Arthrospira platensis* cpcBA was replaced by disrupting the native locus with the desired cpcBA variant, in this case a codon optimized *T. vulcanus* cpcBA. Integration of the construct was selected by the expression of the streptomycin resistance gene aada. Since introduction of aada likely disrupts expression of genes downstream of cpcBA, cpcHIDEF, we facilitated expression of these genes by placing a recombinant *A. platensis* promoter upstream of cpcH (FIG. 12). Three different recombinant *A. platensis* promoters, $P_{apcA}$, $P_{psaL}$, and $P_{atpI}$, were used to drive cpcHIDEF expression, but only one was able to support strain development, $P_{psaL}$ (data not shown). The three additional strains that were constructed to reintroduce *A. platensis* cpcBA into the locus using this configuration revealed that strain construction could be successful using any of the three promoters tested (data not shown). A replacement of the native cpcBA genes with *T. vulcanus* cpcBA results in a protein lysate that is the most thermostable, at 65° C., that we have tested to date (FIG. 13).

Example 3: Thermostable Allophycocyanin

In addition to phycocyanin, *A. platensis* also expresses an additional blue pigmented protein that is a constituent of the phycobilisome, allophycocyanin (APC). APC is comprised of a dimer of ApcA and ApcB that can associate into trimers that assemble higher order structures to form rod-like structures to which phycocyanin is anchored. The absorbance spectra of APC is dependent on its oligomeric state, monomers exhibit a maxima of 615 nm and trimers have a maxima at 650 nm (MacColl 2004). A solution of the APC is typically a teal blue color. We observed that *A. platensis* APC appears more thermostable than *A. platensis* CPC and sought to express a variant of APC that has enhanced attributes to the native protein (data not shown). We expressed *T. vulcanus* apcAB in *A. platensis* cells (SP705, 907, 908); native ApcAB is still expressed in these cells. ApcAB accumulates over 2-fold and 1.4-fold APC:CPC in the soluble fraction when the $P_{cpc600}$ or $P_{cpc290}$ promoters are used to drive expression, respectively (FIGS. 14 and 15). Protein lysate from SP705 was heat-treated to remove *A. platensis* CPC from the sample and the remaining soluble protein, comprised primarily of APC, was tested for stability at 70° C. (FIG. 16). LinaBlue was used as a source for *A. platensis* APC and was found to be substantially less stable than lysate prepared from cells expressing *T. vulcanus* apcAB (FIG. 16).

EMBODIMENTS

Exemplary, non-limiting embodiments of the disclosure are provided below:
1. A thermostable phycobiliprotein modified for greater stability by the formation of covalent disulfide bonds.

2. The thermostable phycobiliprotein of embodiment 1 that is more thermostable than a corresponding wild type or codon-optimized phycobiliprotein.

3. The thermostable phycobiliprotein of any of embodiments 1 to 2, wherein the covalent disulfide bonds are formed between peptide chains.

4. The thermostable phycobiliprotein of any of embodiments 1 to 2, wherein the covalent disulfide bonds are formed within a peptide chain.

5. The thermostable phycobiliprotein of any of embodiments 1 to 4, wherein the disulfide bonds are formed by replacing one or more residues to cysteine in the polypeptide.

6. The thermostable phycobiliprotein of embodiment 5, wherein one or more alanine or serine residues are replaced with one or more cysteine residues.

7. The thermostable phycobiliprotein of any of embodiments 1 to 6, wherein the phycobiliprotein is obtained from an organism that can live at temperatures above 55° C.

8. The thermostable phycobiliprotein of embodiment 7, wherein the phycobiliprotein is obtained from *T. vulcanus*.

9. The thermostable phycobiliprotein of any of embodiments 1 to 8 that is a modified phycocyanin.

10. The thermostable phycobiliprotein of any of embodiments 1-9, wherein the phycobiliprotein is stabilized by the formation of at least one disulfide bond in the CpcA subunit.

11. The thermostable phycobiliprotein of embodiment 10, wherein the phycobiliprotein is stabilized by the formation of at least one disulfide bond between alpha helices of CpcA.

12. The thermostable phycobiliprotein of embodiment 10, wherein the phycobiliprotein is stabilized by the formation of at least one disulfide bond between alpha-helices α2 and α7 or corresponding residues of CpcA.

13. The thermostable phycobiliprotein of embodiment 11 or 12, wherein the phycobiliprotein is stabilized by the formation of at least one disulfide bond between the CpcA and CpcB subunits.

14. The thermostable phycobiliprotein of embodiment 13, wherein the phycobiliprotein is stabilized by the formation of at least one disulfide bond between an alpha-helix of CpcA and the N-terminal region of CpcB.

15. The thermostable phycobiliprotein of embodiment 14, wherein the phycobiliprotein is stabilized by the formation of at least one disulfide bond between alpha-helix α1 of CpcA and the N-terminal region of cpcB upstream of alpha-helix α1 or corresponding residues.

16. The thermostable phycobiliprotein of any of embodiments 1 to 15, wherein the phycobiliprotein is a *T. vulcanus* CpcA where the one or more residues at positions 40 or 146 are replaced by cysteines.

17. The thermostable phycobiliprotein of any of embodiments 1 to 15, wherein the phycobiliprotein is a *T. vulcanus* CpcA where the residues at positions 40 and 146 are replaced by cysteines.

18. The thermostable phycobiliprotein of any of embodiments 1 to 15, wherein any residue is replaced with cysteine.

19. The thermostable phycobiliprotein of embodiment 18, wherein one or more alanine residues are replaced with cysteine.

20. The thermostable phycobiliprotein of any of embodiments 1 to 19, wherein the phycobiliprotein exhibits greater stability at elevated temperatures than the corresponding wild type phycobiliprotein.

21. The thermostable phycobiliprotein of embodiment 20, wherein the phycobiliprotein exhibits more than a two-fold increase in stability at elevated temperatures.

22. The thermostable phycobiliprotein of embodiment 21, wherein the phycobiliprotein exhibits more than a ten-fold increase in stability at elevated temperatures.

23. The thermostable phycobiliprotein of embodiment 22, wherein the phycobiliprotein exhibits more than a fifty-fold increase in stability at elevated temperatures.

24. The thermostable phycobiliprotein of any of embodiments 1 to 23, wherein the phycobiliprotein is stable at temperatures over 60° C.

25. The thermostable phycobiliprotein of embodiment 24, wherein the phycobiliprotein is stable at temperatures over 65° C.

26. The thermostable phycobiliprotein of embodiment 25, wherein the phycobiliprotein is stable at temperatures over 70° C.

27. The thermostable phycobiliprotein of embodiment 26, wherein the phycobiliprotein is stable at temperatures over 75° C.

28. The thermostable phycobiliprotein of any of embodiments 1 to 27 that is thermostable for at least 10 seconds.

29. The thermostable phycobiliprotein of embodiment 28, that is thermostable for about 1 minute.

30. The thermostable phycobiliprotein of embodiment 29, that is thermostable for about 10 minutes.

31. The thermostable phycobiliprotein of embodiment 30, that is thermostable for about thirty minutes.

32. A composition comprising modified *Spirulina* cells expressing a non-native thermostable phycobiliprotein.

33. The composition of embodiment 32, wherein the modified *Spirulina* comprises a thermostable phycobiliprotein of any of embodiments 1-32.

34. The composition of embodiment 32 or 33, wherein the *Spirulina* cell retains one or more endogenous phycobiliproteins.

35. The composition of embodiment 32 or 33, wherein one or more endogenous phycobiliproteins are inactivated, deleted, or replaced.

36. The composition of any of embodiments 32 to 35, wherein the thermostable phycobiliprotein is integrated into the *Spirulina* genome.

37. The composition of any of embodiments 33 to 35, wherein the thermostable phycobiliprotein is maintained on an extrachromosomal plasmid.

38. The composition of any of embodiments 32 to 37, wherein the thermostable phycobiliprotein is overexpressed.

39. The composition of any of embodiments 32 to 37, wherein the thermostable phycobiliprotein is expressed at endogenous levels.

40. The composition of any of embodiments 32 to 37, wherein the thermostable phycobiliprotein is under the control of an inducible promoter.

41. The composition of any of embodiments 32 to 40, wherein the lysate of the *Spirulina* contains a greater amount of the thermostable phycobiliprotein than the amount of one of more endogenous phycobiliproteins.

42. The composition of embodiment 41, wherein the ratio of thermostable phycobiliprotein::endogenous phycobiliprotein is greater than 1:1.

43. The composition of embodiment 42, wherein the ratio of thermostable phycobiliprotein::endogenous phycobiliprotein is greater than 1.4:1.

44. The composition of embodiment 43, wherein the ratio of thermostable phycobiliprotein::endogenous phycobiliprotein is greater than 2:1.

45. The composition of any of embodiments 32 to 44, wherein the thermostable phycobiliprotein is phycocyanin.

46. The composition of any of embodiments 32 to 44, wherein the thermostable phycobiliprotein is allophycocyanin.

47. The composition of any of embodiments 32 to 46, wherein the *Spirulina* is selected from the group consisting of: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri Stizenberger, A. jennerif. purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. *non-constricta, A. platensis* f. *granulate, A. platensis* f. *minor, A. platensis* var. *tenuis, A. santannae, A. setchellii, A. skujae, A. spirulinoides f. tenuis, A. spirulinoides, A. subsalsa, A. subtilissima, A. tenuis, A. tenuissima,* and *A. versicolor.*

48. The composition of embodiment 47, wherein the *Spirulina* is *A. platensis*.

49. A method of making a thermostable phycobiliprotein comprising:
    a) culturing the *Spirulina* composition of any of embodiments 321 to 47 under conditions that allow expression of the phycobiliprotein;
    b) lysing the *Spirulina* cells in the composition; and
    c) recovering the thermostable phycobiliprotein.

All publications, patents, and patent publications cited are incorporated by reference herein in their entirety for all purposes.

This application incorporates by reference the following publications in their entireties for all purposes: U.S. Pat. No. 10,131,870.

REFERENCES

MacColl. Allophycocyanin and energy transfer. Biochima et Biophys Acta. 1657 (2004) 73-81.

Su et al. Structural insights into the cold adaptation of the photosynthetic pigment-protein C-phycocyanin from an Arctic cyanobacterium. Biochimica et Biophysica Acta 1858 (2017) 325-335.

What is claimed is:

1. A thermostable phycobiliprotein modified for greater thermostability by the formation of covalent disulfide bonds, wherein the covalent disulfide bonds are formed by replacing one or more alanine, aspartic acid, or serine residues with one or more cysteine residues in the modified phycobiliprotein, wherein the covalent disulfide bonds are between residues that are within: alpha-helices α2 and α7, of an phycocyanin alpha subunit; or an alpha-helix α1 of the phycocyanin alpha subunit and an N-terminal region of a phycocyanin beta subunit upstream of the alpha-helix α1 the helices determined by alignment with a sequence selected from: SEQ ID NO: 35-36 or 41-42 of the phycocyanin alpha subunit or a sequence selected from SEQ ID NO: 37-40 of the phycocyanin beta subunit.

2. The thermostable phycobiliprotein of claim 1, wherein the phycobiliprotein is obtained from an organism that can live at temperatures above 55° C.

3. The thermostable phycobiliprotein of claim 2, wherein the phycobiliprotein is obtained from *Thermosynechococcus vulcanus*.

4. The thermostable phycobiliprotein of claim 1, wherein the phycobiliprotein is stabilized by the formation of at least one disulfide bond between phycocyanin alpha and beta subunits.

5. The thermostable phycobiliprotein of claim 1, wherein the phycobiliprotein is a *Thermosynechococcus vulcanus* phycocyanin alpha subunit, and wherein the one or more residues at positions 40 or 146 of SEQ ID NO: 41 are replaced by cysteines.

6. The thermostable phycobiliprotein of claim 1, wherein the phycobiliprotein is a *Thermosynechococcus vulcanus* phycocyanin alpha subunit where the residues at positions 40 and 146 of SEQ ID NO: 41 are replaced by cysteines.

7. The thermostable phycobiliprotein of claim 1, wherein the phycobiliprotein exhibits more than a two-fold increase in stability at temperatures from 60° C.-80° C. relative to an unmodified phycobiliprotein.

8. The thermostable phycobiliprotein of claim 1, wherein the phycobiliprotein is more stable at temperatures from 60° C.-80° C. relative to an unmodified phycobiliprotein.

9. The thermostable phycobiliprotein of claim 1, wherein residues at positions 40 and/or 146 of SEQ ID NO 35 or SEQ ID NO: 36 are replaced by cysteines.

10. The thermostable phycobiliprotein of claim 9, wherein the residue at position 40 comprises a A40C modification.

11. The thermostable phycobiliprotein of claim 9, wherein the residues at positions 40 and 146 comprise A40C and A146C modifications.

12. The thermostable phycobiliprotein of claim 1, wherein one or more residues at positions 1 to 3 of SEQ ID NO: 37 or SEQ ID NO: 38 are replaced by cysteines.

13. The thermostable phycobiliprotein of claim 12, wherein the residue at position 3 comprises a D3C modification.

14. The thermostable phycobiliprotein of claim 1, wherein alpha-helix α2 in the alpha subunit is between residues 21-60 of SEQ ID NOs: 35-36; or between residues 21-62 of SEQ ID NOs: 41-42.

15. The thermostable phycobiliprotein of claim 1, wherein alpha-helix α7 in the alpha subunit is between residues 144-160 of SEQ ID NOs: 35-36 or 41-42.

16. The thermostable phycobiliprotein of claim 1, wherein alpha-helix α1 in the alpha subunit is between residues 4-14 of SEQ ID NOs: 35-36.

17. The thermostable phycobiliprotein of claim 1, wherein the N-terminal region of the phycocyanin beta subunit upstream of the alpha-helix α1 is between residues 1-3 of SEQ ID NOs: 37-38 or 39-40.

18. A composition comprising modified *Spirulina* cells expressing a thermostable phycobiliprotein of claim 1.

* * * * *

SEQUENCE LISTING

```
<160> NUMBER OF SEQ ID NOS: 42

<210> SEQ ID NO 1
<211> LENGTH: 519
<212> TYPE: DNA
<213> ORGANISM: Artificial Sequence
<220> FEATURE:
<223> OTHER INFORMATION: Thermosynechococcus vulcanus cpcB codon
``` optimized DNA sequence

<400> SEQUENCE: 1

| | | | | | |
|---|---|---|---|---|---|
| atgttagatg | cctttgccaa | ggtggttgct | caagctgatg | ctcgcggcga | attcctgact | 60 |
| aatgctcaat | ttgatgcact | gtcgaactta | gtgaaagagg | gaaataaaag | actagatgct | 120 |
| gtcaatagga | ttacatccaa | tgcgagcaca | atcgtagcga | atgccgctcg | cgccctcttt | 180 |
| gccgaacaac | cacaattaat | tcagcctggc | ggaaatgcgt | ataccaatcg | acggatggcc | 240 |
| gcctgtttac | gcgatatgga | aattattttg | agatacgtta | cttatgcaat | tctcgccggt | 300 |
| gattcgagtg | ttttagatga | taggtgctta | aacggtttgc | gcgaaaccta | tcaagccctc | 360 |
| ggaaccccg | ggagttcagt | agctgtcgcc | atccagaaaa | tgaaggatgc | cgctatcgcc | 420 |
| attgctaatg | atccaaacgg | tattactcca | ggagattgtt | ctgcgctaat | gtccgagatc | 480 |
| gccggatact | ttgatagagc | agctgctgct | gttgcgtaa | | | 519 |

<210> SEQ ID NO 2
<211> LENGTH: 172
<212> TYPE: PRT
<213> ORGANISM: Thermosynechococcus vulcanus

<400> SEQUENCE: 2

Met Leu Asp Ala Phe Ala Lys Val Val Ala Gln Ala Asp Ala Arg Gly
1               5                   10                  15

Glu Phe Leu Thr Asn Ala Gln Phe Asp Ala Leu Ser Asn Leu Val Lys
            20                  25                  30

Glu Gly Asn Lys Arg Leu Asp Ala Val Asn Arg Ile Thr Ser Asn Ala
        35                  40                  45

Ser Thr Ile Val Ala Asn Ala Ala Arg Ala Leu Phe Ala Glu Gln Pro
    50                  55                  60

Gln Leu Ile Gln Pro Gly Gly Asn Ala Tyr Thr Asn Arg Arg Met Ala
65                  70                  75                  80

Ala Cys Leu Arg Asp Met Glu Ile Ile Leu Arg Tyr Val Thr Tyr Ala
                85                  90                  95

Ile Leu Ala Gly Asp Ser Ser Val Leu Asp Asp Arg Cys Leu Asn Gly
            100                 105                 110

Leu Arg Glu Thr Tyr Gln Ala Leu Gly Thr Pro Gly Ser Ser Val Ala
        115                 120                 125

Val Ala Ile Gln Lys Met Lys Asp Ala Ala Ile Ala Ile Ala Asn Asp
    130                 135                 140

Pro Asn Gly Ile Thr Pro Gly Asp Cys Ser Ala Leu Met Ser Glu Ile
145                 150                 155                 160

Ala Gly Tyr Phe Asp Arg Ala Ala Ala Ala Val Ala
                165                 170

<210> SEQ ID NO 3
<211> LENGTH: 489
<212> TYPE: DNA
<213> ORGANISM: Artificial Sequence
<220> FEATURE:
<223> OTHER INFORMATION: Thermosynechococcus vulcanus cpcA A40C A146C
      codon optimized DNA sequence

<400> SEQUENCE: 3

| | | | | | |
|---|---|---|---|---|---|
| atgaaaaccc | ccataaccga | agcaatcgcg | gctgctgaca | cacaaggaag | atttctatct | 60 |
| aacactgaat | tacaggccgt | tgatggaagg | tttaaagag | cggtggctag | catggaatgc | 120 |
| gcccgggctt | tgacaaacaa | cgcacagtct | ttaatagatg | gagcagccca | ggcggtctat | 180 |

```
caaaaatttc cctatacaac gacaatgcaa gggagtcaat atgcttctac gcctgaaggt    240
aaagccaaat gtgcacgcga tattggctat tatctccgga tgattactta ctgtttagta    300
gcgggtggta caggccctat ggatgaatat ctcattgccg gtttaagtga aatcaattcc    360
actttcgatc tatcaccctc ctggtacatc gaagctctca agtatattaa agctaatcat    420
gggctcactg gacaatgtgc cgttgaagca aatgcgtaca tagattacgc tattaatgct    480
ttaagctaa                                                            489
```

<210> SEQ ID NO 4
<211> LENGTH: 162
<212> TYPE: PRT
<213> ORGANISM: Thermosynechococcus vulcanus
<220> FEATURE:
<221> NAME/KEY: SITE
<222> LOCATION: (1)..(162)
<223> OTHER INFORMATION: Thermosynechococcus vulcanus cpcA A40C A146C
      protein sequence

<400> SEQUENCE: 4

```
Met Lys Thr Pro Ile Thr Glu Ala Ile Ala Ala Ala Asp Thr Gln Gly
1               5                   10                  15

Arg Phe Leu Ser Asn Thr Glu Leu Gln Ala Val Asp Gly Arg Phe Lys
            20                  25                  30

Arg Ala Val Ala Ser Met Glu Cys Ala Arg Ala Leu Thr Asn Asn Ala
        35                  40                  45

Gln Ser Leu Ile Asp Gly Ala Ala Gln Ala Val Tyr Gln Lys Phe Pro
    50                  55                  60

Tyr Thr Thr Thr Met Gln Gly Ser Gln Tyr Ala Ser Thr Pro Glu Gly
65                  70                  75                  80

Lys Ala Lys Cys Ala Arg Asp Ile Gly Tyr Tyr Leu Arg Met Ile Thr
                85                  90                  95

Tyr Cys Leu Val Ala Gly Gly Thr Gly Pro Met Asp Glu Tyr Leu Ile
            100                 105                 110

Ala Gly Leu Ser Glu Ile Asn Ser Thr Phe Asp Leu Ser Pro Ser Trp
        115                 120                 125

Tyr Ile Glu Ala Leu Lys Tyr Ile Lys Ala Asn His Gly Leu Thr Gly
    130                 135                 140

Gln Cys Ala Val Glu Ala Asn Ala Tyr Ile Asp Tyr Ala Ile Asn Ala
145                 150                 155                 160

Leu Ser
```

<210> SEQ ID NO 5
<211> LENGTH: 7030
<212> TYPE: DNA
<213> ORGANISM: Artificial Sequence
<220> FEATURE:
<223> OTHER INFORMATION: Plasmid pLM660 complete sequence

<400> SEQUENCE: 5

```
ggaatcatga atcatcccac aactaagcat caaaaaatta catcctgtta ctggggaatt     60
tctgaactac ctgggttaga tacaggtaat attaaactcc tgaatcaatg tggtattgaa    120
aacacccagc aactgctcac gcgcgggagt aataatgcta ataaaatcgc cttatctaac    180
caactaggta tcaacatcag agatatcagt aaatgggtcg caatgtccga cttagccagg    240
gttcccagta ttggctatca atattgtggt gtccttttgc atagtggcgt aagttcagtt    300
aaccaactat ctcagatgtc tattcaacaa ctgcataaac agatttttacg gctctatgta    360
```

```
ggaaccttgc aatctcgcca actctgtcca tctgttgatg tcatccaaac ctggattaaa      420
caagctaaaa ttttgcataa aattaattaa taattactag atgaaatcat gaattttttcc     480 gaagatttgc gacaaaatgc accagccacc gaaagaaacc gcgaacctat tttagaggtc      540
ttaaaaaggg tgttgcccgc cacgggaacc gttttagaag tagccagcgg cacaggacaa      600
cacgcggttt tttttgctcc ccgtctctcc cctaggcggt ggctaccttc cgacccgcaa      660
cctttgttac aacagagtat aaagcatgg caaattcatt caccttcaga taatctttac       720
cctcccctac agttaaatgt agaagctaat ccttggccag tggaagggaa tgatttaccc      780
tgggaattat cggaatttcc catcactgct attgtagcaa ttaacctgat tcatatttcg      840
ccttggtcgg cttgtgaagg gttaatggcg ggaagcgatc gcattttgaa accgggggga      900
attttatatc tctatggacc ctataaaata gctggaaaac acaccgcacc tagtaacgct      960
tcctttgatg aatatttgcg aacttctaac cctaagtggg gtgtcagaaa ccttgatgat     1020
tcacatacgc ggccgcctgg gccttgagct cgaatttcct gcattaatga atcggccaac     1080
gcgcggggag aggcggtttg cgtattgggc gctcttccgc ttcctcgctc actgactcgc     1140
tgcgctcggt cgttcggctg cggcgagcgg tatcagctca ctcaaaggcg gtaatacggt     1200
tatccacaga atcaggggat aacgcaggaa agaacatgtg agcaaaaggc cagcaaaagg     1260
ccaggaaccg taaaaatagc ggagtgtata ctggcttact atgttggcac tgatgagggt     1320
gtcagtgaag tgcttcatgt ggcaggagaa aaaaggctgc accggtgcgt cagcagaata     1380
tgtgatacag gatatattcc gcttcctcgc tcactgactc gctacgctcg gtcgttcgac     1440
tgcggcgagc ggaaatggct tacgaacggg gcggagattt cctggaagat gccaggaaga     1500
tacttaacag ggaagtgaga gggccgcggc aaagccgttt ttccataggc tccgcccccc     1560
tgacaagcat cacgaaatct gacgctcaaa tcagtggtgg cgaaacccga caggactata     1620
aagataccag gcgttttccccc ctggcggctc cctcgtgcgc tctcctgttc ctgcctttcg     1680
gtttaccggt gtcattccgc tgttatggcc gcgtttgtct cattccacgc ctgacactca     1740
gttccgggta ggcagttcgc tccaagctgg actgtatgca cgaaccccccc attcagtccg     1800 accgctgcgc cttatccggt aactatcgtc ttgagtccaa cccggaaaga catgcaaaag     1860
caccactggc agcagccact ggtaattgat ttagaggagt tagtcttgaa gtcatgcgcc     1920
ggttaaggct aaactgaaag gacaagtttt ggtgactgcg ctcctccaag ccagttacct     1980
cggttcaaag agttggtagc tcagagaacc ttcgaaaaac cgccctgcaa ggcggttttt     2040
tcgttttcag agcaagagat tacgcgcaga ccaaaacgat ctcaagaaga tcatcttatt     2100
aagattatca aaaggatctt tcacctagat cctttaaat taaaaatgaa gttttaaatc       2160
aatctaaagt atatatgagt aaacttggtc tgacagttac caatgcttaa tcagtgaggc     2220
acctatctca gcgatctgtc tatttcgttc atccatagtt gcctgactcc ccgtcgtgta     2280
gataactacg atacgggagg gcttaccatc tggccccagt gctgcaatga taccgcggga     2340
cccacgctca ccggctccag atttatcagc aataaaccag ccagccggaa gggccgagcg     2400
cagaagtggt cctgcaactt tatccgcctc catccagtct attaattgtt gccgggaagc     2460
tagagtaagt agttcgccag ttaatagttt gcgcaacgtt gttgccattg ctacaggcat     2520
cgtggtgtca cgctcgtcgt ttggtatggc ttcattcagc tccggttccc aacgatcaag     2580
gcgagttaca tgatccccca tgttgtgcaa aaaagcggtt agctccttcg gtcctccgat     2640
cgttgtcaga agtaagttgg ccgcagtgtt atcactcatg gttatggcag cactgcataa     2700
```

```
ttctcttact gtcatgccat ccgtaagatg cttttctgtg actggtgagt actcaaccaa    2760
gtcattctga gaatagtgta tgcggcgacc gagttgctct tgcccggcgt caatacggga    2820
taataccgcg ccacatagca gaactttaaa agtgctcatc attggaaaac gttcttcggg    2880
gcgaaaactc tcaaggatct taccgctgtt gagatccagt tcgatgtaac ccactcgtgc    2940
acccaactga tcttcagcat cttttacttt caccagcgtt tctgggtgag caaaaacagg    3000
aaggcaaaat gccgcaaaaa agggaataag ggcgacacgg aaatgttgaa tactcatact    3060
cttcctttt caatattatt gaagcattta tcagggttat tgtctcatga gcggatacat    3120
atttgaatgt atttagaaaa ataaacaaat aggggttccg cgcacatttc cccgaaaagt    3180
gccacctgac gtctaagaaa ccattattat catgacatta acctataaaa ataggcgtat    3240
cacgaggccc tttcgtctcg cgcgtttcgg tgatgacggt gaaaacctct gacacatgca    3300
gctcccggag acggtcacag cttgtctgta agcggatgcc aagcttgcat gctgcaggt    3360
ggcgcgccta gggggagga ttttatgatc ggatgttgag tcagtctgag tggtctaaaa    3420
ttcctacggt gggaattgtg tttgcggccg ccagggtgga tactctccct agggatagtt    3480
gggaccagcc tttggcggcg gtttgtacag aggagggtat atgggagttt ccaaaataac    3540
ttctggtggg ggggcaaatt atcgggcgat cgccacttat atggtattaa ttgctatagc    3600
gatcgctatg ctatttcccc tattttggtt ggtgggaact gcctttaaat cccctaccga    3660
aaacatcttt caggttcccc cccagtttat tccaagggaa cctactttca ctaattttgt    3720
cagagtttgg caaaccaatc cctttggtcg ctatttattt aatagtaccc tcgtcgccct    3780
tttaaccgtc ggattaaatc tgctattttg ttccttggcg gcctatcctt tggcgcgctt    3840
aaacttttgg ggtcgcgatt ttctcctaag tgcgatcgtt tccaccatca tgataccctt    3900
tcagattgtc atgattcccc tgtatattct agcagtacag ttaggattaa gaaatactta    3960
tttaggcatt atttttccat ctttagcctc cgcttttggc atctttctat tgcgacaggc    4020
atttatggga gttcccaaag agttagaaga agccgccaga attgatggct gttcagaatt    4080
agggatttgg tggcatatta tgatccctc agtccgtccc gccttaatga ccttagccat    4140
ttttgtattt atcgggtctt ggagtgattt tctctggccc ttaattgtag tcgatcgccc    4200
agaatattat accatcccctt taggcgtggc aaatctagcc ggaactttt ctctcgattg    4260
gcggatagtc gccgccggtt ccgtcatttc tatcgctcct gtgttactac tattttttaat    4320
cgtacaacgg tatattgtgc ctacagatac agctacgggg gttaaaggtt gaatgaggat    4380
tattaatctc agtcctaata atcaaaatca tatccaccag gcggcgactt tattagtcgc    4440
agaatttcgg gaaaattggc cgaatgcttg gccgacttat gaacgtggtt tagccgaggt    4500
tatggagtct tttggcgacg atagagttaa tctagtcgcc gtcgatgaaa atgataatct    4560
tctaggctgg attggtggta ttagccaata tcaaggccat gtttgggaat tacatccttt    4620
ggtagtcaaa agcgattatc aagggttagg aataggcga aaattggtcg ccaatttaga    4680
ggattatgtc cgctcacaag gagggttaac cttatggttg ggtaccgatg acgaaaataa    4740
tttaacctcc ctatctggtg tcgaattata cccccatttt ttggaaaata ttgctaacat    4800
aaaaaaccat ggtcgtcatc cctatgaatt ttatcagaaa tgcggttttg tgattatggg    4860
agtagtcccc gatgctaacg gtatcgggaa acctgatatt ttgatggcta aatctctgag    4920
aattgacaat catcctaaat ccaactgaat gttgtcagtt aagtttatag gctgctatg    4980
gtatgataaa aaaatccccc cagcagttgg gggggaatga ttaattaggt attgaattgg    5040
ttaaattgga ggtgtgttgg ggctgacttt tgctgccttg ttggggggg cgattttaac    5100
```

```
tgaggtcact ttttcttggc cgggattggc taatcgcttg tatgaggcta tccgtctgcg    5160
ggattatccc acggttcaag gggtggtggt attttggcc gttattgtgg tggcggctag     5220
tttggcgatc gatattttga atgcttgtat tgacccacgg attcgctatt aattccctgt    5280
cagaaaatat acttagttat taatacttag ttattttct taataaattt taacaaacca    5340
aagggcgttg gcagtgtata aaggatattt gaaggggtga aaggaaggc gaatgttgat     5400 ttatgaagtt tgattaacat ttgtatcaaa atataaaatt cttctcataa accctgtaca    5460
atcttttaag atttcggaaa gtgttctagg atactgaaga atgaaccac ggggcaattg     5520 ttaaaagcct ttgtcgatgg ttcgccccgg aaggggtctt aggaggtgac accgatggat    5580
tgattgtcgt gatcattcat ggtgtgtcca atcccaactc aactctaagc aagtcaacaa    5640
gtaggagata aatctatgtt agatgccttt gccaaggtgg ttgctcaagc tgatgctcgc    5700
ggcgaattcc tgactaatgc tcaatttgat gcactgtcga acttagtgaa agagggaaat    5760
aaaagactag atgctgtcaa taggattaca tccaatgcga gcacaatcgt agcgaatgcc    5820
gctcgcgccc tctttgccga acaaccacaa ttaattcagc ctggcggaaa tgcgtatacc    5880
aatcgacgga tggccgcctg tttacgcgat atggaaatta ttttgagata cgttacttat    5940
gcaattctcg ccggtgattc gagtgtttta gatgataggt gcttaaacgg tttgcgcgaa    6000
acctatcaag ccctcggaac ccccgggagt tcagtagctg tcgccatcca gaaaatgaag    6060
gatgccgcta tcgccattgc taatgatcca aacggtatta ctccaggaga ttgttctgcg    6120
ctaatgtccg agatcgccgg atactttgat agagcagctg ctgctgttgc gtaatcaagc    6180
agatccatag catataacaa ttgaaacagt ttagctgaag tctaagtgac tggacttctg    6240
tttgttacct aatttttgt aaaccaatcg ggagataact cgagaatgaa accccccata    6300
accgaagcaa tcgcggctgc tgcacacaca ggaagatttc tatctaacac tgaattacag    6360
gccgttgatg gaaggtttaa aagagcggtg gctagcatgg aatgcgcccg ggctttgaca    6420
aacaacgcac agtctttaat agatggagca gcccaggcgg tctatcaaaa atttccctat    6480
acaacgacaa tgcaagggag tcaatatgct tctacgcctg aaggtaaagc caaatgtgca    6540
cgcgatattg gctattatct ccggatgatt acttactgtt tagtagcggg tggtacaggc    6600
cctatggatg aatatctcat tgccggttta agtgaaatca attccacttt cgatctatca    6660
ccctcctggt acatcgaagc tctcaagtat attaaagcta atcatgggct cactggacaa    6720
tgtgccgttg aagcaaatgc gtacatagat tacgctatta atgctttaag ctaacagcca    6780
aataaaacga aaggctcagt cgaaagactg ggcctttcgt tttatctgtt gtttgtcggt    6840
gaacgctctc ctgagtagga caaatccgcc gggagcggat ttgaacgttg cgaagcaacg    6900
gcccggaggg tggcgggcag gacgcccgcc ataaactgcc aggcatcaaa ttaagcagaa    6960
ggccatcctg acggatggcc ttttgcgtt tctacaaact ccggatccgg ccggcttgaa      7020
gacagaatgc                                                            7030
```

<210> SEQ ID NO 6
<211> LENGTH: 519
<212> TYPE: DNA
<213> ORGANISM: Artificial Sequence
<220> FEATURE:
<223> OTHER INFORMATION: Thermosynechococcus vulcanus cpcB D3C codon
      optimized DNA sequence

<400> SEQUENCE: 6

```
atgttatgtg cctttgccaa ggtggttgct caagctgatg ctcgcggcga attcctgact     60
```

```
aatgctcaat tgatgcact gtcgaactta gtgaaagagg gaaataaaag actagatgct    120
gtcaatagga ttacatccaa tgcgagcaca atcgtagcga atgccgctcg cgccctcttt    180
gccgaacaac cacaattaat tcagcctggc ggaaatgcgt ataccaatcg acggatggcc    240
gcctgtttac gcgatatgga aattattttg agatacgtta cttatgcaat tctcgccggt    300
gattcgagtg ttttagatga taggtgctta aacggtttgc gcgaaaccta tcaagccctc    360 ggaaccccg ggagttcagt agctgtcgcc atccagaaaa tgaaggatgc cgctatcgcc    420
attgctaatg atccaaacgg tattactcca ggagattgtt ctgcgctaat gtccgagatc    480
gccggatact ttgatagagc agctgctgct gttgcgtaa                          519
```

```
<210> SEQ ID NO 7
<211> LENGTH: 172
<212> TYPE: PRT
<213> ORGANISM: Artificial Sequence
<220> FEATURE:
<223> OTHER INFORMATION: Thermosynechococcus vulcanus cpcB D3C codon
      optimized

<400> SEQUENCE: 7

Met Leu Cys Ala Phe Ala Lys Val Val Ala Gln Ala Asp Ala Arg Gly
1               5                   10                  15

Glu Phe Leu Thr Asn Ala Gln Phe Asp Ala Leu Ser Asn Leu Val Lys
            20                  25                  30

Glu Gly Asn Lys Arg Leu Asp Ala Val Asn Arg Ile Thr Ser Asn Ala
        35                  40                  45

Ser Thr Ile Val Ala Asn Ala Ala Arg Ala Leu Phe Ala Glu Gln Pro
    50                  55                  60

Gln Leu Ile Gln Pro Gly Gly Asn Ala Tyr Thr Asn Arg Arg Met Ala
65                  70                  75                  80

Ala Cys Leu Arg Asp Met Glu Ile Ile Leu Arg Tyr Val Thr Tyr Ala
                85                  90                  95

Ile Leu Ala Gly Asp Ser Ser Val Leu Asp Asp Arg Cys Leu Asn Gly
            100                 105                 110

Leu Arg Glu Thr Tyr Gln Ala Leu Gly Thr Pro Gly Ser Ser Val Ala
        115                 120                 125

Val Ala Ile Gln Lys Met Lys Asp Ala Ala Ile Ala Ile Ala Asn Asp
    130                 135                 140

Pro Asn Gly Ile Thr Pro Gly Asp Cys Ser Ala Leu Met Ser Glu Ile
145                 150                 155                 160

Ala Gly Tyr Phe Asp Arg Ala Ala Ala Ala Val Ala
                165                 170
```

```
<210> SEQ ID NO 8
<211> LENGTH: 489
<212> TYPE: DNA
<213> ORGANISM: Artificial Sequence
<220> FEATURE:
<223> OTHER INFORMATION: Thermosynechococcus vulcanus cpcA I5C codon
      optimized DNA sequence

<400> SEQUENCE: 8
atgaaaaccc cctgtaccga agcaatcgcg gctgctgaca cacaaggaag atttctatct    60
aacactgaat tacaggccgt tgatggaagg tttaaaagag cggtggctag catggaagct    120
gcccgggctt tgacaaacaa cgcacagtct ttaatagatg agcagcccca ggcggtctat    180
caaaaatttc cctatacaac gacaatgcaa gggagtcaat atgcttctac gcctgaaggt    240
```

```
aaagccaaat gtgcacgcga tattggctat tatctccgga tgattactta ctgtttagta    300
gcgggtggta caggccctat ggatgaatat ctcattgccg gtttaagtga atcaattcc     360 actttcgatc tatcaccctc ctggtacatc gaagctctca agtatattaa agctaatcat    420
gggctcactg acaagccgc cgttgaagca aatgcgtaca tagattacgc tattaatgct    480
ttaagctaa                                                            489
```

<210> SEQ ID NO 9
<211> LENGTH: 162
<212> TYPE: PRT
<213> ORGANISM: Artificial Sequence
<220> FEATURE:
<223> OTHER INFORMATION: Thermosynechococcus vulcanus cpcA I5C codon optimized

<400> SEQUENCE: 9

```
Met Lys Thr Pro Cys Thr Glu Ala Ile Ala Ala Ala Asp Thr Gln Gly
1               5                   10                  15

Arg Phe Leu Ser Asn Thr Glu Leu Gln Ala Val Asp Gly Arg Phe Lys
            20                  25                  30

Arg Ala Val Ala Ser Met Glu Ala Ala Arg Ala Leu Thr Asn Asn Ala
        35                  40                  45

Gln Ser Leu Ile Asp Gly Ala Ala Gln Ala Val Tyr Gln Lys Phe Pro
    50                  55                  60

Tyr Thr Thr Thr Met Gln Gly Ser Gln Tyr Ala Ser Thr Pro Glu Gly
65                  70                  75                  80

Lys Ala Lys Cys Ala Arg Asp Ile Gly Tyr Tyr Leu Arg Met Ile Thr
                85                  90                  95

Tyr Cys Leu Val Ala Gly Gly Thr Gly Pro Met Asp Glu Tyr Leu Ile
            100                 105                 110

Ala Gly Leu Ser Glu Ile Asn Ser Thr Phe Asp Leu Ser Pro Ser Trp
        115                 120                 125

Tyr Ile Glu Ala Leu Lys Tyr Ile Lys Ala Asn His Gly Leu Thr Gly
    130                 135                 140

Gln Ala Val Glu Ala Asn Ala Tyr Ile Asp Tyr Ala Ile Asn Ala
145                 150                 155                 160

Leu Ser
```

<210> SEQ ID NO 10
<211> LENGTH: 7030
<212> TYPE: DNA
<213> ORGANISM: Artificial Sequence
<220> FEATURE:
<223> OTHER INFORMATION: Plasmid pLM659 complete sequence

<400> SEQUENCE: 10

```
ggaatcatga atcatcccac aactaagcat caaaaaatta catcctgtta ctggggaatt     60
tctgaactac ctgggttaga tacaggtaat attaaactcc tgaatcaatg tggtattgaa    120
aacacccagc aactgctcac gcgcgggagt aataatgcta ataaaatcgc cttatctaac    180
caactaggta tcaacatcag agatatcagt aaatgggtcg caatgtccga cttagccagg    240
gttcccagta ttggctatca atattgtggt gtccttttgc atagtggcgt aagttcagtt    300
aaccaactat ctcagatgtc tattcaacaa ctgcataaac agattttacg gctctatgta    360
ggaaccttgc aatctcgcca actctgtcca tctgttgatg tcatccaaac ctggattaaa    420
caagctaaaa ttttgcataa aattaattaa taattactag atgaaatcat gaattttttcc    480
```

```
gaagatttgc gacaaaatgc accagccacc gaaagaaacc gcgaacctat tttagaggtc    540
ttaaaaaggg tgttgcccgc cacgggaacc gttttagaag tagccagcgg cacaggacaa    600
cacgcggttt tttttgctcc ccgtctctcc cctaggcggt ggctaccttc cgacccgcaa    660
cctttgttac aacagagtat taaagcatgg caaattcatt caccttcaga taatctttac    720 cctccectac agttaaatgt agaagctaat ccttggccag tggaagggaa tgatttaccc    780
tgggaattat cggaatttcc catcactgct attgtagcaa ttaacctgat tcatatttcg    840
ccttggtcgg cttgtgaagg gttaatggcg ggaagcgatc gcattttgaa accggggga    900 attttatatc tctatggacc ctataaaata gctggaaaac acaccgcacc tagtaacgct    960
tcctttgatg aatatttgcg aacttctaac cctaagtggg gtgtcagaaa ccttgatgat   1020
tcacatacgc ggccgcctgg gccttgagct cgaatttcct gcattaatga atcggccaac   1080
gcgcggggag aggcggtttg cgtattgggc gctcttccgc ttcctcgctc actgactcgc   1140
tgcgctcggt cgttcggctg cggcgagcgg tatcagctca ctcaaaggcg gtaatacggt   1200
tatccacaga atcaggggat aacgcaggaa agaacatgtg agcaaaaggc cagcaaaagg   1260
ccaggaaccg taaaaatagc ggagtgtata ctggcttact atgttggcac tgatgagggt   1320
gtcagtgaag tgcttcatgt ggcaggagaa aaaaggctgc accggtgcgt cagcagaata   1380
tgtgatacag gatatattcc gcttcctcgc tcactgactc gctacgctcg gtcgttcgac   1440
tgcggcgagc ggaaatggct tacgaacggg gcggagattt cctggaagat gccaggaaga   1500
tacttaacag ggaagtgaga gggccgcggc aaagccgttt ttccataggc tccgcccccc   1560
tgacaagcat cacgaaatct gacgctcaaa tcagtggtgg cgaaacccga caggactata   1620
aagataccag gcgtttcccc ctggcggctc cctcgtgcgc tctcctgttc ctgcctttcg   1680
gtttaccggt gtcattccgc tgttatggcc gcgtttgtct cattccacgc ctgacactca   1740
gttccgggta ggcagttcgc tccaagctgg actgtatgca cgaaccccc attcagtccg   1800 accgctgcgc cttatccggt aactatcgtc ttgagtccaa cccggaaaga catgcaaaag   1860
caccactggc agcagccact ggtaattgat ttagaggagt tagtcttgaa gtcatgcgcc   1920
ggttaaggct aaactgaaag gacaagtttt ggtgactgcg ctcctccaag ccagttacct   1980
cggttcaaag agttggtagc tcagagaacc ttcgaaaaac cgccctgcaa ggcggttttt   2040
tcgttttcag agcaagagat tacgcgcaga ccaaaacgat ctcaagaaga tcatcttatt   2100
aagattatca aaaggatct tcacctagat cctttaaat taaaaatgaa gttttaaatc    2160
aatctaaagt atatatgagt aaacttggtc tgacagttac caatgcttaa tcagtgaggc   2220
acctatctca gcgatctgtc tatttcgttc atccatagtt gcctgactcc ccgtcgtgta   2280
gataactacg atacgggagg gcttaccatc tggccccagt gctgcaatga taccgcggga   2340
cccacgctca ccggctccag atttatcagc aataaaccag ccagccggaa gggccgagcg   2400
cagaagtggt cctgcaactt tatccgcctc catccagtct attaattgtt gccgggaagc   2460
tagagtaagt agttcgccag ttaatagttt gcgcaacgtt gttgccattg ctacaggcat   2520
cgtggtgtca cgctcgtcgt ttggtatggc ttcattcagc tccggttccc aacgatcaag   2580
gcgagttaca tgatccccca tgttgtgcaa aaaagcggtt agctccttcg gtcctccgat   2640
cgttgtcaga agtaagttgg ccgcagtgtt atcactcatg gttatggcag cactgcataa   2700
ttctcttact gtcatgccat ccgtaagatg cttttctgtg actggtgagt actcaaccaa   2760
gtcattctga gaatagtgta tgcggcgacc gagttgctct tgcccggcgt caatacggga   2820
```

-continued

```
taataccgcg ccacatagca gaactttaaa agtgctcatc attggaaaac gttcttcggg      2880
gcgaaaactc tcaaggatct taccgctgtt gagatccagt tcgatgtaac ccactcgtgc      2940
acccaactga tcttcagcat cttttacttt caccagcgtt tctgggtgag caaaaacagg      3000
aaggcaaaat gccgcaaaaa agggaataag ggcgacacgg aaatgttgaa tactcatact      3060
cttccttttt caatattatt gaagcattta tcagggttat tgtctcatga gcggatacat      3120
atttgaatgt atttagaaaa ataaacaaat aggggttccg cgcacatttc cccgaaaagt      3180
gccacctgac gtctaagaaa ccattattat catgacatta acctataaaa ataggcgtat      3240
cacgaggccc tttcgtctcg cgcgtttcgg tgatgacggt gaaaacctct gacacatgca      3300
gctcccggag acggtcacag cttgtctgta agcggatgcc aagcttgcat gcctgcaggt      3360
ggcgcgccta tggggaggga ttttatgatc ggatgttgag tcagtctgag tggtctaaaa      3420
ttcctacggt gggaattgtg tttgcggccg ccagggtgga tactctccct agggatagtt      3480
gggaccagcc tttggcggcg gtttgtacag aggagggtat atgggagttt ccaaaataac      3540
ttctggtggg ggggcaaatt atcgggcgat cgccacttat atggtattaa ttgctatagc      3600
gatcgctatg ctatttcccc tattttggtt ggtgggaact gcctttaaat ccctaccga      3660 aaacatcttt caggttcccc cccagtttat tccaagggaa cctactttca ctaatttgt      3720 cagagtttgg caaccaatc cctttggtcg ctatttattt aatagtaccc tcgtcgccct      3780
tttaaccgtc ggattaaatc tgctattttg ttccttggcg gcctatcctt ggcgcgctt      3840 aaacttttgg ggtcgcgatt ttctcctaag tgcgatcgtt tccaccatca tgatacccctt     3900 tcagattgtc atgattcccc tgtatattct agcagtacag ttaggattaa gaaatactta     3960
tttaggcatt atttttccat ctttagcctc cgcttttggc atctttctat tgcgacaggc     4020
atttatggga gttcccaaag agttagaaga agccgccaga attgatggct gttcagaatt     4080
agggatttgg tggcatatta tgatccctc agtccgtccc gccttaatga ccttagccat      4140
ttttgtattt atcgggtctt ggagtgattt tctctggccc ttaattgtag tcgatcgccc     4200
agaatattat accatccctt taggcgtggc aaatctagcc ggaactttt ctctcgattg      4260 gcggatagtc gccgccggtt ccgtcatttc tatcgctcct gtgttactac tatttttaat     4320
cgtacaacgg tatattgtgc ctacagatac agctacgggg gttaaaggtt gaatgaggat     4380
tattaatctc agtcctaata atcaaaatca tatccaccag gcggcgactt tattagtcgc     4440
agaatttcgg gaaaattggc cgaatgcttg gccgacttat gaacgtggtt tagccgaggt     4500
tatggagtct tttggcgacg atagagttaa tctagtcgcc gtcgatgaaa atgataatct     4560
tctaggctgg attggtggta ttagccaata tcaaggccat gtttgggaat tacatccttt     4620
ggtagtcaaa agcgattatc aagggttagg aataggggcga aaattggtcg ccaatttaga     4680
ggattatgtc cgctcacaag gagggttaac cttatggttg ggtaccgatg acgaaaataa     4740
tttaacctcc ctatctggtg tcgaattata cccccatttt ttggaaaata ttgctaacat     4800
aaaaaaccat ggtcgtcatc cctatgaatt ttatcagaaa tgcggttttg tgattatggg     4860
agtagtcccc gatgctaacg gtatcggaa acctgatatt ttgatggcta aatctctgag     4920
aattgacaat catcctaaat ccaactgaat gttgtcagtt aagtttatag gctgctatg      4980 gtatgataaa aaaatccccc cagcagttgg gggggaatga ttaattaggt attgaattgg     5040
ttaaattgga ggtgtgttgg ggctgacttt tgctgccttg ttggggggggg cgattttaac     5100 tgaggtcact ttttcttggc cgggattggc taatcgcttg tatgaggcta tccgtctgcg     5160
ggattatccc acggttcaag gggtggtggt atttttggcc gttattgtgg tggcggctag     5220
```

```
tttggcgatc gatattttga atgcttgtat tgacccacgg attcgctatt aattccctgt    5280
cagaaaatat acttagttat taatacttag ttatttttct taataaattt taacaaacca    5340
aagggcgttg gcagtgtata aaggatattt gaaggggtga aaggaaggc gaatgttgat    5400 ttatgaagtt tgattaacat ttgtatcaaa atataaaatt cttctcataa accctgtaca    5460
atcttttaag atttcggaaa gtgttctagg atactgaaga atgaaccac ggggcaattg    5520 ttaaaagcct ttgtcgatgg ttcgccccgg aaggggtctt aggaggtgac accgatggat    5580
tgattgtcgt gatcattcat ggtgtgtcca atcccaactc aactctaagc aagtcaacaa    5640
gtaggagata aatctatgtt atgtgccttt gccaaggtgg ttgctcaagc tgatgctcgc    5700
ggcgaattcc tgactaatgc tcaatttgat gcactgtcga acttagtgaa agagggaaat    5760
aaaagactag atgctgtcaa taggattaca tccaatgcga gcacaatcgt agcgaatgcc    5820
gctcgcgccc tctttgccga acaaccacaa ttaattcagc ctggcggaaa tgcgtatacc    5880
aatcgacgga tggccgcctg tttacgcgat atggaaatta ttttgagata cgttacttat    5940
gcaattctcg ccggtgattc gagtgtttta gatgataggt gcttaaacgg tttgcgcgaa    6000
acctatcaag ccctcggaac ccccgggagt tcagtagctg tcgccatcca gaaaatgaag    6060
gatgccgcta tcgccattgc taatgatcca aacggtatta ctccaggaga ttgttctgcg    6120
ctaatgtccg agatcgccgg atactttgat agagcagctg ctgctgttgc gtaatcaagc    6180
agatccatag catataacaa ttgaaacagt ttagctgaag tctaagtgac tggacttctg    6240
tttgttacct aatttttttgt aaaccaatcg ggagataact cgagaatgaa accccctgt    6300 accgaagcaa tcgcggctgc tgacacacaa ggaagatttc tatctaacac tgaattacag    6360
gccgttgatg gaaggtttaa aagagcggtg gctagcatgg aagctgcccg ggctttgaca    6420
aacaacgcac agtctttaat agatggagca gcccaggcgg tctatcaaaa atttccctat    6480
acaacgacaa tgcaagggag tcaatatgct tctacgcctg aaggtaaagc caaatgtgca    6540
cgcgatattg gctattatct ccggatgatt acttactgtt tagtagcggg tggtacaggc    6600
cctatggatg aatatctcat tgccggttta agtgaaatca attccacttt cgatctatca    6660
ccctcctggt acatcgaagc tctcaagtat attaaagcta atcatgggct cactggacaa    6720
gccgccgttg aagcaaatgc gtacatagat tacgctatta atgctttaag ctaacagcca    6780
aataaaacga aaggctcagt cgaaagactg ggcctttcgt tttatctgtt gtttgtcggt    6840
gaacgctctc ctgagtagga caaatccgcc gggagcggat ttgaacgttg cgaagcaacg    6900 gccccggaggg tggcgggcag gacgcccgcc ataaactgcc aggcatcaaa ttaagcagaa    6960
ggccatcctg acggatggcc tttttgcgtt tctacaaact ccggatccgg ccggcttgaa    7020
gacagaatgc                                                           7030
```

<210> SEQ ID NO 11
<211> LENGTH: 489
<212> TYPE: DNA
<213> ORGANISM: Artificial Sequence
<220> FEATURE:
<223> OTHER INFORMATION: Thermosynechococcus vulcanus cpcA I5C A40C
      A146C codon optimized DNA sequence

<400> SEQUENCE: 11

```
atgaaaaccc cctgtaccga agcaatcgcg gctgctgaca cacaaggaag atttctatct     60
aacactgaat tacaggccgt tgatggaagg tttaaaagag cggtggctag catggaatgc    120
gcccgggctt tgacaaacaa cgcacagtct ttaatagatg gagcagccca ggcggtctat    180
```

```
caaaaatttc cctatacaac gacaatgcaa gggagtcaat atgcttctac gcctgaaggt    240
aaagccaaat gtgcacgcga tattggctat tatctccgga tgattactta ctgtttagta    300
gcgggtggta caggccctat ggatgaatat ctcattgccg gtttaagtga aatcaattcc    360
actttcgatc tatcaccctc ctggtacatc gaagctctca agtatattaa agctaatcat    420
gggctcactg gacaatgtgc cgttgaagca aatgcgtaca tagattacgc tattaatgct    480
ttaagctaa                                                            489
```

<210> SEQ ID NO 12
<211> LENGTH: 162
<212> TYPE: PRT
<213> ORGANISM: Artificial Sequence
<220> FEATURE:
<223> OTHER INFORMATION: Thermosynechococcus vulcanus cpcA I5C A40C
      A146C

<400> SEQUENCE: 12

```
Met Lys Thr Pro Cys Thr Glu Ala Ile Ala Ala Asp Thr Gln Gly
 1               5                  10                  15

Arg Phe Leu Ser Asn Thr Glu Leu Gln Ala Val Asp Gly Arg Phe Lys
                20                  25                  30

Arg Ala Val Ala Ser Met Glu Cys Ala Arg Ala Leu Thr Asn Asn Ala
            35                  40                  45

Gln Ser Leu Ile Asp Gly Ala Ala Gln Ala Val Tyr Gln Lys Phe Pro
        50                  55                  60

Tyr Thr Thr Thr Met Gln Gly Ser Gln Tyr Ala Ser Thr Pro Glu Gly
 65                  70                  75                  80

Lys Ala Lys Cys Ala Arg Asp Ile Gly Tyr Tyr Leu Arg Met Ile Thr
                85                  90                  95

Tyr Cys Leu Val Ala Gly Gly Thr Gly Pro Met Asp Glu Tyr Leu Ile
           100                 105                 110

Ala Gly Leu Ser Glu Ile Asn Ser Thr Phe Asp Leu Ser Pro Ser Trp
       115                 120                 125

Tyr Ile Glu Ala Leu Lys Tyr Ile Lys Ala Asn His Gly Leu Thr Gly
   130                 135                 140

Gln Cys Ala Val Glu Ala Asn Ala Tyr Ile Asp Tyr Ala Ile Asn Ala
145                 150                 155                 160

Leu Ser
```

<210> SEQ ID NO 13
<211> LENGTH: 7030
<212> TYPE: DNA
<213> ORGANISM: Artificial Sequence
<220> FEATURE:
<223> OTHER INFORMATION: Plasmid pLM658 complete sequence

<400> SEQUENCE: 13

```
ggaatcatga atcatcccac aactaagcat caaaaaatta catcctgtta ctggggaatt     60
tctgaactac ctgggttaga tacaggtaat attaaactcc tgaatcaatg tggtattgaa    120
aacacccagc aactgctcac gcgcgggagt aataatgcta ataaaatcgc cttatctaac    180
caactaggta tcaacatcag agatatcagt aaatgggtcg caatgtccga cttagccagg    240
gttcccagta ttggctatca atattgtggt gtccttttgc atagtggcgt aagttcagtt    300
aaccaactat ctcagatgtc tattcaacaa ctgcataaac agattttacg gctctatgta    360
ggaaccttgc aatctcgcca actctgtcca tctgttgatg tcatccaaac ctggattaaa    420
```

```
caagctaaaa ttttgcataa aattaattaa taattactag atgaaatcat gaattttttcc      480 gaagatttgc gacaaaatgc accagccacc gaaagaaacc gcgaacctat tttagaggtc      540
ttaaaaaggg tgttgcccgc cacgggaacc gttttagaag tagccagcgg cacaggacaa      600
cacgcggttt ttttgctcc ccgtctctcc cctaggcgt ggctaccttc cgacccgcaa        660
cctttgttac aacagagtat taaagcatgg caaattcatt caccttcaga taatctttac      720
cctcccctac agttaaatgt agaagctaat ccttggccag tggaagggaa tgatttaccc      780
tgggaattat cggaatttcc catcactgct attgtagcaa ttaacctgat tcatatttcg      840
ccttggtcgg cttgtgaagg gttaatggcg ggaagcgatc gcattttgaa accgggggga      900
attttatatc tctatggacc ctataaaata gctggaaaac acaccgcacc tagtaacgct      960
tcctttgatg aatatttgcg aacttctaac cctaagtggg gtgtcagaaa ccttgatgat     1020
tcacatacgc ggccgcctgg gccttgagct cgaatttcct gcattaatga atcggccaac     1080
gcgcggggag aggcggtttg cgtattgggc gctcttccgc ttcctcgctc actgactcgc     1140
tgcgctcggt cgttcggctg cggcgagcgg tatcagctca ctcaaaggcg gtaatacggt     1200
tatccacaga atcaggggat aacgcaggaa agaacatgtg agcaaaaggc cagcaaaagg     1260
ccaggaaccg taaaaatagc ggagtgtata ctggcttact atgttggcac tgatgagggt     1320
gtcagtgaag tgcttcatgt ggcaggagaa aaaaggctgc accggtgcgt cagcagaata     1380
tgtgatacag gatatattcc gcttcctcgc tcactgactc gctacgctcg gtcgttcgac     1440
tgcggcgagc ggaaatggct tacgaacggg gcggagattt cctggaagat gccaggaaga     1500
tacttaacag ggaagtgaga gggccgcggc aaagccgttt ttccataggc tccgcccccc     1560
tgacaagcat cacgaaatct gacgctcaaa tcagtggtgg cgaaacccga caggactata     1620
aagataccag gcgtttcccc ctggcggctc cctcgtgcgc tctcctgttc ctgcctttcg     1680
gtttaccggt gtcattccgc tgttatggcc gcgtttgtct cattccacgc ctgacactca     1740
gttccgggta ggcagttcgc tccaagctgg actgtatgca cgaaccccc attcagtccg      1800 accgctgcgc cttatccggt aactatcgtc ttgagtccaa cccggaaaga catgcaaaag     1860
caccactggc agcagccact ggtaattgat ttagaggagt tagtcttgaa gtcatgcgcc     1920
ggttaaggct aaactgaaag gacaagtttt ggtgactgcg ctcctccaag ccagttacct     1980
cggttcaaag agttggtagc tcagagaacc ttcgaaaaac cgccctgcaa ggcggttttt     2040
tcgttttcag agcaagagat tacgcgcaga ccaaaacgat ctcaagaaga tcatcttatt     2100
aagattatca aaaggatct tcacctagat ccttttaaat taaaaatgaa gttttaaatc      2160
aatctaaagt atatatgagt aaacttggtc tgacagttac caatgcttaa tcagtgaggc     2220
acctatctca gcgatctgtc tatttcgttc atccatagtt gcctgactcc ccgtcgtgta     2280
gataactacg atacgggagg gcttaccatc tggccccagt gctgcaatga taccgcggga     2340
cccacgctca ccggctccag atttatcagc aataaaccag ccagccggaa gggccgagcg     2400
cagaagtggt cctgcaactt tatccgcctc catccagtct attaattgtt gccgggaagc     2460
tagagtaagt agttcgccag ttaatagttt gcgcaacgtt gttgccattg ctacaggcat     2520
cgtggtgtca cgctcgtcgt ttggtatggc ttcattcagc tccggttccc aacgatcaag     2580
gcgagttaca tgatccccca tgttgtgcaa aaaagcggtt agctccttcg gtcctccgat     2640
cgttgtcaga agtaagttgg ccgcagtgtt atcactcatg gttatggcag cactgcataa     2700
ttctcttact gtcatgccat ccgtaagatg cttttctgtg actggtgagt actcaaccaa     2760
```

```
gtcattctga gaatagtgta tgcggcgacc gagttgctct tgcccggcgt caatacggga   2820
taataccgcg ccacatagca gaactttaaa agtgctcatc attggaaaac gttcttcggg   2880
gcgaaaactc tcaaggatct taccgctgtt gagatccagt tcgatgtaac ccactcgtgc   2940
acccaactga tcttcagcat cttttacttt caccagcgtt tctgggtgag caaaaacagg   3000
aaggcaaaat gccgcaaaaa agggaataag gcgacacgg aaatgttgaa tactcatact    3060
cttccttttt caatattatt gaagcattta tcagggttat tgtctcatga gcggatacat   3120
atttgaatgt atttagaaaa ataaacaaat aggggttccg cgcacatttc cccgaaaagt   3180
gccacctgac gtctaagaaa ccattattat catgacatta acctataaaa ataggcgtat   3240
cacgaggccc tttcgtctcg cgcgtttcgg tgatgacggt gaaaacctct gacacatgca   3300
gctcccggag acggtcacag cttgtctgta agcggatgcc aagcttgcat gcctgcaggt   3360
ggcgcgccta tggggagga ttttatgatc ggatgttgag tcagtctgag tggtctaaaa    3420
ttcctacggt gggaattgtg tttgcggccg ccagggtgga tactctccct agggatagtt   3480
gggaccagcc tttggcggcg gtttgtacag aggagggtat atgggagttt ccaaaataac   3540
ttctggtggg gggcaaatt atcgggcgat cgccacttat atggtattaa ttgctatagc    3600
gatcgctatg ctatttcccc tattttggtt ggtgggaact gcctttaaat cccctaccga   3660
aaacatcttt caggttcccc cccagtttat tccaagggaa cctactttca ctaattttgt   3720
cagagtttgg caaccaatc cctttggtcg ctatttattt aatagtaccc tcgtcgccct    3780
tttaaccgtc ggattaaatc tgctattttg ttccttggcg gcctatcctt ggcgcgctt    3840 aaacttttgg ggtcgcgatt ttctcctaag tgcgatcgtt tccaccatca tgatacccett  3900 tcagattgtc atgattcccc tgtatattct agcagtacag ttaggattaa gaaatactta   3960
tttaggcatt ttttttccat ctttagcctc cgcttttggc atctttctat tgcgacaggc   4020
atttatggga gttcccaaag agttagaaga agccgccaga attgatggct gttcagaatt   4080
agggattggg tggcatatta tgatcccctc agtccgtccc gccttaatga ccttagccat   4140
ttttgtattt atcgggtctt ggagtgattt tctctggccc ttaattgtag tcgatcgccc   4200
agaatattat accatccctt taggcgtggc aaatctagcc ggaactttt ctctcgattg    4260 gcggatagtc gccgccggtt ccgtcatttc tatcgctcct gtgttactac tatttttaat   4320
cgtacaacgg tatattgtgc ctacagatac agctacgggg gttaaaggtt gaatgaggat   4380
tattaatctc agtcctaata atcaaaatca tatccaccag gcggcgactt tattagtcgc   4440
agaatttcgg gaaaattggc cgaatgcttg gccgacttat gaacgtggtt tagccgaggt   4500
tatggagtct tttggcgacg atagagttaa tctagtcgcc gtcgatgaaa atgataatct   4560
tctaggctgg attggtggta ttagccaata tcaaggccat gtttgggaat tacatccttt   4620
ggtagtcaaa agcgattatc aagggttagg aatagggcga aaattggtcg ccaatttaga   4680
ggattatgtc cgctcacaag gagggttaac cttatggttg gtaccgatg acgaaaataa    4740 tttaacctcc ctatctggtg tcgaattata ccccccatttt ttggaaaata ttgctaacat   4800
aaaaaaccat ggtcgtcatc cctatgaatt ttatcagaaa tgcggttttg tgattatggg   4860
agtagtcccc gatgctaacg gtatcgggaa acctgatatt ttgatggcta aatctctgag   4920
aattgacaat catcctaaat ccaactgaat gttgtcagtt aagtttatag ggctgctatg   4980
gtatgataaa aaaatccccc cagcagttgg gggggaatga ttaattaggt attgaattgg   5040
ttaaattgga ggtgtgttgg ggctgacttt tgctgccttg ttgggggggg cgattttaac   5100
tgaggtcact ttttcttggc cgggattggc taatcgcttg tatgaggcta tccgtctgcg   5160
```

```
ggattatccc acggttcaag gggtggtggt attttggcc gttattgtgg tggcggctag      5220
tttggcgatc gatattttga atgcttgtat tgacccacgg attcgctatt aattccctgt      5280
cagaaaatat acttagttat taatacttag ttattttct taataaattt taacaaacca       5340
aagggcgttg gcagtgtata aaggatattt gaaggggtga gaaggaaggc gaatgttgat      5400
ttatgaagtt tgattaacat ttgtatcaaa atataaaatt cttctcataa accctgtaca      5460
atcttttaag atttcggaaa gtgttctagg atactgaaga aatgaaccac ggggcaattg      5520
ttaaaagcct ttgtcgatgg ttcgccccgg aaggggtctt aggaggtgac accgatggat      5580
tgattgtcgt gatcattcat ggtgtgtcca atcccaactc aactctaagc aagtcaacaa      5640
gtaggagata aatctatgtt atgtgccttt gccaaggtgg ttgctcaagc tgatgctcgc      5700
ggcgaattcc tgactaatgc tcaatttgat gcactgtcga acttagtgaa agagggaaat      5760
aaaagactag atgctgtcaa taggattaca tccaatgcga gcacaatcgt agcgaatgcc      5820
gctcgcgccc tctttgccga acaaccacaa ttaattcagc ctggcggaaa tgcgtatacc      5880
aatcgacgga tggccgcctg tttacgcgat atggaaatta ttttgagata cgttacttat      5940
gcaattctcg ccggtgattc gagtgtttta gatgataggt gcttaaacgg tttgcgcgaa      6000
acctatcaag ccctcggaac ccccgggagt tcagtagctg tcgccatcca gaaaatgaag      6060
gatgccgcta tcgccattgc taatgatcca aacggtatta ctccaggaga ttgttctgcg      6120
ctaatgtccg agatcgccgg atactttgat agagcagctg ctgctgttgc gtaatcaagc      6180
agatccatag catataacaa ttgaaacagt ttagctgaag tctaagtgac tggacttctg      6240
tttgttacct aatttttgt aaaccaatcg ggagataact cgagaatgaa acccccctgt       6300
accgaagcaa tcgcggctgc tgacacacaa ggaagatttc tatctaacac tgaattacag      6360
gccgttgatg gaaggtttaa aagagcggtg gctagcatgg aatgcgcccg ggctttgaca      6420
aacaacgcac agtctttaat agatggagca gcccaggcgg tctatcaaaa atttccctat      6480
acaacgacaa tgcaagggag tcaatatgct tctacgcctg aaggtaaagc caaatgtgca      6540
cgcgatattg gctattatct ccggatgatt acttactgtt tagtagcggg tggtacaggc      6600
cctatggatg aatatctcat tgccggttta agtgaaatca attccacttt cgatctatca      6660
ccctcctggt acatcgaagc tctcaagtat attaaagcta atcatgggct cactggacaa      6720
tgtgccgttg aagcaaatgc gtacatagat tacgctatta atgctttaag ctaacagcca      6780
aataaaacga aaggctcagt cgaaagactg ggcctttcgt tttatctgtt gtttgtcggt      6840
gaacgctctc ctgagtagga caaatccgcc gggagcggat ttgaacgttg cgaagcaacg      6900
gcccggaggg tggcgggcag gacgcccgcc ataaactgcc aggcatcaaa ttaagcagaa      6960
ggccatcctg acggatggcc tttttgcgtt tctacaaact ccggatccgg ccggcttgaa      7020
gacagaatgc                                                             7030
```

<210> SEQ ID NO 14
<211> LENGTH: 519
<212> TYPE: DNA
<213> ORGANISM: Arthrospira platensis
<220> FEATURE:
<221> NAME/KEY: misc_feature
<222> LOCATION: (1)..(519)
<223> OTHER INFORMATION: A. platensis cpcB DNA sequence

<400> SEQUENCE: 14

```
atgtttgatg ccttcaccaa ggtggtttct caagctgata ctcgcggcga aatgctgagt         60
```

| | |
|---|---|
| acagctcaaa tcgatgctct gagccaaatg gttgctgaaa gcaacaaacg tttggattct | 120 |
| gttaaccgca ttaccagcaa cgcttccacc attgtttcca acgctgctcg ttctttgttc | 180 |
| gcagagcaac cccaactgat tgctcccggt ggaaacgcct acaccagccg tcgtatggct | 240 |
| gcttgcttgc gtgacatgga aatcatcctg cgctatgtaa cctacgctgt gtttgctggc | 300 |
| gatgcaagtg ttctcgaaga tcgttgcttg aacggtttgc gtgaaactta cctggctttg | 360 |
| ggaactcccg gttcttccgt tgctgtcggt gttggcaaaa tgaaagaagc tgctctggcg | 420 |
| atcgttaacg atcccgcagg tatcactcct ggtgattgta gcgctttggc ttcagaaatc | 480 |
| gctggttact tgaccgtgc tgctgcagca gtttcctaa | 519 |

```
<210> SEQ ID NO 15
<211> LENGTH: 172
<212> TYPE: PRT
<213> ORGANISM: Arthrospira platensis
<220> FEATURE:
<221> NAME/KEY: SITE
<222> LOCATION: (1)..(172)
<223> OTHER INFORMATION: A. platensis cpcB protein sequence

<400> SEQUENCE: 15
```

Met Phe Asp Ala Phe Thr Lys Val Val Ser Gln Ala Asp Thr Arg Gly
1               5                   10                  15

Glu Met Leu Ser Thr Ala Gln Ile Asp Ala Leu Ser Gln Met Val Ala
            20                  25                  30

Glu Ser Asn Lys Arg Leu Asp Ser Val Asn Arg Ile Thr Ser Asn Ala
        35                  40                  45

Ser Thr Ile Val Ser Asn Ala Ala Arg Ser Leu Phe Ala Glu Gln Pro
    50                  55                  60

Gln Leu Ile Ala Pro Gly Gly Asn Ala Tyr Thr Ser Arg Arg Met Ala
65                  70                  75                  80

Ala Cys Leu Arg Asp Met Glu Ile Ile Leu Arg Tyr Val Thr Tyr Ala
                85                  90                  95

Val Phe Ala Gly Asp Ala Ser Val Leu Glu Asp Arg Cys Leu Asn Gly
            100                 105                 110

Leu Arg Glu Thr Tyr Leu Ala Leu Gly Thr Pro Gly Ser Ser Val Ala
        115                 120                 125

Val Gly Val Gly Lys Met Lys Glu Ala Ala Leu Ala Ile Val Asn Asp
    130                 135                 140

Pro Ala Gly Ile Thr Pro Gly Asp Cys Ser Ala Leu Ala Ser Glu Ile
145                 150                 155                 160

Ala Gly Tyr Phe Asp Arg Ala Ala Ala Ala Val Ser
                165                 170

```
<210> SEQ ID NO 16
<211> LENGTH: 489
<212> TYPE: DNA
<213> ORGANISM: Artificial Sequence
<220> FEATURE:
<223> OTHER INFORMATION: Arthrospira platensis cpcA A40C A146C DNA
      sequence

<400> SEQUENCE: 16
```

| | |
|---|---|
| atgaaaaccc ccctaaccga agcagtttct atcgctgatt cccaaggtcg tttcctaagc | 60 |
| agcaccgaaa tccaagtagc ttttggccgt tttcgtcaag ccaaagctgg tctggaatgc | 120 |
| gctaaagctt tgacctctaa agctgatagt ctgatcagtg gtgctgccca agcagtgtac | 180 |
| aacaagttcc cctacaccac ccaaatgcag ggacctaact acgcggcaga ccaacgcggt | 240 |

```
aaggacaaat gtgctcgtga cataggctac tacctgcgga tggtaactta ttgcctgatt    300
gctggtggaa ctggccccat ggatgagtac ctgattgccg gtattgatga atcaaccgg    360 actttcgagc tttctccaag ctggtacatt gaagccctga atacatcaa agctaaccac    420 ggtttgtctg gtgactgtgc tgttgaagct aactcctacc tcgactacgc gatcaacgcc    480
ctgagctag                                                            489
```

```
<210> SEQ ID NO 17
<211> LENGTH: 162
<212> TYPE: PRT
<213> ORGANISM: Artificial Sequence
<220> FEATURE:
<223> OTHER INFORMATION: Arthrospira platensis cpcA A40C A146C protein
      sequence

<400> SEQUENCE: 17
```

```
Met Lys Thr Pro Leu Thr Glu Ala Val Ser Ile Ala Asp Ser Gln Gly
1               5                   10                  15

Arg Phe Leu Ser Ser Thr Glu Ile Gln Val Ala Phe Gly Arg Phe Arg
            20                  25                  30

Gln Ala Lys Ala Gly Leu Glu Cys Ala Lys Ala Leu Thr Ser Lys Ala
        35                  40                  45

Asp Ser Leu Ile Ser Gly Ala Ala Gln Ala Val Tyr Asn Lys Phe Pro
    50                  55                  60

Tyr Thr Thr Gln Met Gln Gly Pro Asn Tyr Ala Ala Asp Gln Arg Gly
65                  70                  75                  80

Lys Asp Lys Cys Ala Arg Asp Ile Gly Tyr Tyr Leu Arg Met Val Thr
                85                  90                  95

Tyr Cys Leu Ile Ala Gly Gly Thr Gly Pro Met Asp Glu Tyr Leu Ile
            100                 105                 110

Ala Gly Ile Asp Glu Ile Asn Arg Thr Phe Glu Leu Ser Pro Ser Trp
        115                 120                 125

Tyr Ile Glu Ala Leu Lys Tyr Ile Lys Ala Asn His Gly Leu Ser Gly
    130                 135                 140

Asp Cys Ala Val Glu Ala Asn Ser Tyr Leu Asp Tyr Ala Ile Asn Ala
145                 150                 155                 160

Leu Ser
```

```
<210> SEQ ID NO 18
<211> LENGTH: 7030
<212> TYPE: DNA
<213> ORGANISM: Artificial Sequence
<220> FEATURE:
<223> OTHER INFORMATION: Plasmid pLM665 complete sequence

<400> SEQUENCE: 18
```

```
ggaatcatga atcatcccac aactaagcat caaaaaatta catcctgtta ctggggaatt     60
tctgaactac ctgggttaga tacaggtaat attaaactcc tgaatcaatg tggtattgaa    120
aacacccagc aactgctcac gcgcgggagt aataatgcta ataaaatcgc cttatctaac    180
caactaggta tcaacatcag agatatcagt aaatgggtcg caatgtccga cttagccagg    240
gttcccagta ttggctatca atattgtggt gtccttttgc atagtggcgt aagttcagtt    300
aaccaactat ctcagatgtc tattcaacaa ctgcataaac agattttacg gctctatgta    360
ggaaccttgc aatctcgcca actctgtcca tctgttgatg tcatccaaac ctggattaaa    420
caagctaaaa ttttgcataa aattaattaa taattactag atgaaatcat gaattttttcc    480
```

```
gaagatttgc gacaaaatgc accagccacc gaaagaaacc gcgaacctat tttagaggtc    540
ttaaaaaggg tgttgcccgc cacgggaacc gttttagaag tagccagcgg cacaggacaa    600
cacgcggttt tttttgctcc ccgtctctcc cctaggcggt ggctaccttc cgacccgcaa    660
cctttgttac aacagagtat aaagcatgg  caaattcatt caccttcaga taatctttac    720
cctcccctac agttaaatgt agaagctaat ccttggccag tggaagggaa tgatttaccc    780
tgggaattat cggaatttcc catcactgct attgtagcaa ttaacctgat tcatatttcg    840
ccttggtcgg cttgtgaagg gttaatggcg ggaagcgatc gcattttgaa accgggggga    900
attttatatc tctatggacc ctataaaata gctggaaaac acaccgcacc tagtaacgct    960
tcctttgatg aatatttgcg aacttctaac cctaagtggg gtgtcagaaa ccttgatgat   1020
tcacatacgc ggccgcctgg gccttgagct cgaatttcct gcattaatga atcggccaac   1080
gcgcggggag aggcggtttg cgtattgggc gctcttccgc ttcctcgctc actgactcgc   1140
tgcgctcggt cgttcggctg cggcgagcgg tatcagctca ctcaaaggcg gtaatacggt   1200
tatccacaga atcaggggat aacgcaggaa agaacatgtg agcaaaaggc cagcaaaagg   1260
ccaggaaccg taaaaatagc ggagtgtata ctggcttact atgttggcac tgatgagggt   1320
gtcagtgaag tgcttcatgt ggcaggagaa aaaaggctgc accggtgcgt cagcagaata   1380
tgtgatacag gatatattcc gcttcctcgc tcactgactc gctacgctcg gtcgttcgac   1440
tgcggcgagc ggaaatggct tacgaacggg gcggagattt cctggaagat gccaggaaga   1500
tacttaacag ggaagtgaga gggccgcggc aaagccgttt ttccataggc tccgcccccc   1560
tgacaagcat cacgaaatct gacgctcaaa tcagtggtgg cgaaacccga caggactata   1620
aagataccag gcgtttcccc ctggcggctc cctcgtgcgc tctcctgttc ctgcctttcg   1680
gtttaccggt gtcattccgc tgttatggcc gcgtttgtct cattccacgc ctgacactca   1740
gttccgggta ggcagttcgc tccaagctgg actgtatgca cgaaccccccc attcagtccg   1800 accgctgcgc cttatccggt aactatcgtc ttgagtccaa cccggaaaga catgcaaaag   1860
caccactggc agcagccact ggtaattgat ttagaggagt tagtcttgaa gtcatgcgcc   1920
ggttaaggct aaactgaaag gacaagtttt ggtgactgcg ctcctccaag ccagttacct   1980
cggttcaaag agttggtagc tcagagaacc ttcgaaaaac cgccctgcaa ggcggttttt   2040
tcgttttcag agcaagagat tacgcgcaga ccaaaacgat ctcaagaaga tcatcttatt   2100
aagattatca aaaggatct  tcacctagat ccttttaaat taaaaatgaa gttttaaatc   2160
aatctaaagt atatatgagt aaacttggtc tgacagttac caatgcttaa tcagtgaggc   2220
acctatctca gcgatctgtc tatttcgttc atccatagtt gcctgactcc ccgtcgtgta   2280
gataactacg atacgggagg gcttaccatc tggccccagt gctgcaatga taccgcggga   2340
cccacgctca ccggctccag atttatcagc aataaaccag ccagccggaa gggccgagcg   2400
cagaagtggt cctgcaactt tatccgcctc catccagtct attaattgtt gccgggaagc   2460
tagagtaagt agttcgccag ttaatagttt gcgcaacgtt gttgccattg ctacaggcat   2520
cgtggtgtca cgctcgtcgt ttggtatggc ttcattcagc tccggttccc aacgatcaag   2580
gcgagttaca tgatccccca tgttgtgcaa aaaagcggtt agctccttcg gtcctccgat   2640
cgttgtcaga agtaagttgg ccgcagtgtt atcactcatg gttatggcag cactgcataa   2700
ttctcttact gtcatgccat ccgtaagatg ctttttctgtg actggtgagt actcaaccaa   2760
gtcattctga gaatagtgta tgcggcgacc gagttgctct tgcccggcgt caatacggga   2820
```

-continued

```
taataccgcg ccacatagca gaactttaaa agtgctcatc attggaaaac gttcttcggg    2880
gcgaaaactc tcaaggatct taccgctgtt gagatccagt tcgatgtaac ccactcgtgc    2940
acccaactga tcttcagcat cttttacttt caccagcgtt tctgggtgag caaaaacagg    3000
aaggcaaaat gccgcaaaaa agggaataag ggcgacacgg aaatgttgaa tactcatact    3060
cttccttttt caatattatt gaagcattta tcagggttat tgtctcatga gcggatacat    3120
atttgaatgt atttagaaaa ataaacaaat aggggttccg cgcacatttc cccgaaaagt    3180
gccacctgac gtctaagaaa ccattattat catgacatta acctataaaa ataggcgtat    3240
cacgaggccc tttcgtctcg cgcgtttcgg tgatgacggt gaaaacctct gacacatgca    3300
gctcccggag acggtcacag cttgtctgta agcggatgcc aagcttgcat gcctgcaggt    3360
ggcgcgccta tggggaggga ttttatgatc ggatgttgag tcagtctgag tggtctaaaa    3420
ttcctacggt gggaattgtg tttgcggccg ccagggtgga tactctccct agggatagtt    3480
gggaccagcc tttggcggcg gtttgtacag aggagggtat atgggagttt ccaaaataac    3540
ttctggtggg ggggcaaatt atcgggcgat cgccacttat atggtattaa ttgctatagc    3600
gatcgctatg ctatttcccc tatttttggtt ggtgggaact gcctttaaat cccctaccga    3660
aaacatcttt caggttcccc cccagtttat tccaagggaa cctactttca ctaatttgt     3720 cagagtttgg caaccaatc cctttggtcg ctatttattt aatagtaccc tcgtcgccct     3780
tttaaccgtc ggattaaatc tgctattttg ttccttggcg gcctatcctt tggcgcgctt    3840
aaacttttgg ggtcgcgatt ttctcctaag tgcgatcgtt tccaccatca tgataccctt    3900
tcagattgtc atgattcccc tgtatattct agcagtacag ttaggattaa gaaatactta    3960
tttaggcatt attttttccat ctttagcctc cgcttttggc atctttctat tgcgacaggc   4020
atttatggga gttcccaaag agttagaaga agccgccaga attgatggct gttcagaatt    4080
agggatttgg tggcatatta tgatccctc agtccgtccc gccttaatga ccttagccat     4140
ttttgtattt atcgggtctt ggagtgattt tctctggccc ttaattgtag tcgatcgccc    4200
agaatattat accatcccctt taggcgtggc aaatctagcc ggaactttt ctctcgattg     4260 gcggatagtc gccgccggtt ccgtcatttc tatcgctcct gtgttactac tatttttaat    4320
cgtacaacgg tatattgtgc ctacagatac agctacgggg gttaaaggtt gaatgaggat    4380
tattaatctc agtcctaata atcaaaatca tatccaccag gcggcgactt tattagtcgc    4440
agaatttcgg gaaaattggc cgaatgcttg gccgacttat gaacgtggtt tagccgaggt    4500
tatggagtct tttggcgacg atagagttaa tctagtcgcc gtcgatgaaa atgataatct    4560
tctaggctgg attggtggta ttagccaata tcaaggccat gtttgggaat tacatccttt    4620
ggtagtcaaa agcgattatc aagggttagg aatagggcga aaattggtcg ccaatttaga    4680
ggattatgtc cgctcacaag gagggttaac cttatggttg ggtaccgatg acgaaaataa    4740
tttaacctcc ctatctggtg tcgaattata cccccatttt ttggaaaata ttgctaacat    4800
aaaaaaccat ggtcgtcatc cctatgaatt ttatcagaaa tgcggttttg tgattatggg    4860
agtagtcccc gatgctaacg gtatcgggaa acctgatatt ttgatggcta aatctctgag    4920
aattgacaat catcctaaat ccaactgaat gttgtcagtt aagtttatag gctgctatg    4980 gtatgataaa aaaatccccc cagcagttgg ggggggaatga ttaattaggt attgaattgg    5040
ttaaattgga ggtgtgttgg ggctgacttt tgctgccttg ttgggggggg cgattttaac    5100
tgaggtcact ttttcttggc cgggattggc taatcgcttg tatgaggcta ccgtctgcg     5160 ggattatccc acggttcaag gggtggtggt attttttggcc gttattgtgg tggcggctag    5220
```

```
tttggcgatc gatattttga atgcttgtat tgacccacgg attcgctatt aattccctgt   5280
cagaaaatat acttagttat taatacttag ttatttttct taataaattt taacaaacca   5340
aagggcgttg gcagtgtata aaggatattt gaaggggtga aaggaaggc gaatgttgat    5400 ttatgaagtt tgattaacat ttgtatcaaa atataaaatt cttctcataa accctgtaca   5460
atcttttaag atttcggaaa gtgttctagg atactgaaga aatgaaccac ggggcaattg   5520
ttaaaagcct ttgtcgatgg ttcgccccgg aaggggtctt aggaggtgac accgatggat   5580
tgattgtcgt gatcattcat ggtgtgtcca atcccaactc aactctaagc aagtcaacaa   5640
gtaggagata aatctatgtt tgatgccttc accaaggtgg tttctcaagc tgatactcgc   5700
ggcgaaatgc tgagtacagc tcaaatcgat gctctgagcc aaatggttgc tgaaagcaac   5760
aaacgtttgg attctgttaa ccgcattacc agcaacgctt ccaccattgt ttccaacgct   5820
gctcgttctt tgttcgcaga gcaaccccaa ctgattgctc ccggtggaaa cgcctacacc   5880
agccgtcgta tggctgcttg cttgcgtgac atggaaatca tcctgcgcta tgtaacctac   5940
gctgtgtttg ctggcgatgc aagtgttctc gaagatcgtt gcttgaacgg tttgcgtgaa   6000
acttacctgg ctttgggaac tcccggttct tccgttgctg tcggtgttgg caaaatgaaa   6060
gaagctgctc tggcgatcgt taacgatccc gcaggtatca ctcctggtga ttgtagcgct   6120
ttggcttcag aaatcgctgg ttactttgac cgtgctgctg cagcagtttc ctaatcaagc   6180
agatccatag catataacaa ttgaaacagt ttagctgaag tctaagtgac tggacttctg   6240
tttgttacct aattttttgt aaaccaatcg ggagataact cgagaatgaa acccccccta   6300
accgaagcag tttctatcgc tgattcccaa ggtcgtttcc taagcagcac cgaaatccaa   6360
gtagcttttg gccgttttcg tcaagccaaa gctggtctgg aatgcgctaa agctttgacc   6420
tctaaagctg atagtctgat cagtggtgct gcccaagcag tgtacaacaa gttcccctac   6480
accacccaaa tgcagggacc taactacgcg cagaccaaac gcggtaagga caaatgtgct   6540
cgtgacatag gctactacct gcggatggta acttattgcc tgattgctgg tggaactggc   6600
cccatggatg agtacctgat tgccggtatt gatgaaatca accggacttt cgagcttcct   6660
ccaagctggt acattgaagc cctgaaatac atcaaagcta ccacggtttt gtctggtgac   6720
tgtgctgttg aagctaactc ctacctcgac tacgcgatca acgccctgag ctagcagcca   6780
aataaaacga aaggctcagt cgaaagactg ggcctttcgt tttatctgtt gtttgtcggt   6840
gaacgctctc ctgagtagga caaatccgcc gggagcggat ttgaacgttg cgaagcaacg   6900
gcccggaggg tggcgggcag gacgcccgcc ataaactgcc aggcatcaaa ttaagcagaa   6960
ggccatcctg acggatggcc ttttttgcgtt tctacaaact ccggatccgg ccggcttgaa   7020
gacagaatgc                                                         7030
```

<210> SEQ ID NO 19
<211> LENGTH: 489
<212> TYPE: DNA
<213> ORGANISM: Artificial Sequence
<220> FEATURE:
<223> OTHER INFORMATION: Thermosynechococcus vulcanus cpcA codon
      optimized DNA sequence

<400> SEQUENCE: 19

```
atgaaaaccc ccataaccga agcaatcgcg gctgctgaca cacaaggaag atttctatct      60
aacactgaat tacaggccgt tgatggaagg tttaaaagag cggtggctag catggaagct    120 gcccggggctt tgacaaacaa cgcacagtct ttaatagatg gagcagccca ggcggtctat   180
```

```
caaaaatttc cctatacaac gacaatgcaa gggagtcaat atgcttctac gcctgaaggt        240
aaagccaaat gtgcacgcga tattggctat tatctccgga tgattactta ctgtttagta        300
gcgggtggta caggccctat ggatgaatat ctcattgccg gtttaagtga aatcaattcc        360
actttcgatc tatcaccctc ctggtacatc gaagctctca agtatattaa agctaatcat        420
gggctcactg gacaagccgc cgttgaagca aatgcgtaca tagattacgc tattaatgct        480
ttaagctaa                                                                489
```

```
<210> SEQ ID NO 20
<211> LENGTH: 162
<212> TYPE: PRT
<213> ORGANISM: Thermosynechococcus vulcanus
<220> FEATURE:
<221> NAME/KEY: SITE
<222> LOCATION: (1)..(162)
<223> OTHER INFORMATION: Thermosynechococcus vulcanus cpcA codon
      optimized protein sequence

<400> SEQUENCE: 20
```

Met Lys Thr Pro Ile Thr Glu Ala Ile Ala Ala Ala Asp Thr Gln Gly
1               5                   10                  15

Arg Phe Leu Ser Asn Thr Glu Leu Gln Ala Val Asp Gly Arg Phe Lys
            20                  25                  30

Arg Ala Val Ala Ser Met Glu Ala Ala Arg Ala Leu Thr Asn Asn Ala
        35                  40                  45

Gln Ser Leu Ile Asp Gly Ala Ala Gln Ala Val Tyr Gln Lys Phe Pro
    50                  55                  60

Tyr Thr Thr Thr Met Gln Gly Ser Gln Tyr Ala Ser Thr Pro Glu Gly
65                  70                  75                  80

Lys Ala Lys Cys Ala Arg Asp Ile Gly Tyr Tyr Leu Arg Met Ile Thr
                85                  90                  95

Tyr Cys Leu Val Ala Gly Gly Thr Gly Pro Met Asp Glu Tyr Leu Ile
            100                 105                 110

Ala Gly Leu Ser Glu Ile Asn Ser Thr Phe Asp Leu Ser Pro Ser Trp
        115                 120                 125

Tyr Ile Glu Ala Leu Lys Tyr Ile Lys Ala Asn His Gly Leu Thr Gly
    130                 135                 140

Gln Ala Ala Val Glu Ala Asn Ala Tyr Ile Asp Tyr Ala Ile Asn Ala
145                 150                 155                 160

Leu Ser

```
<210> SEQ ID NO 21
<211> LENGTH: 6957
<212> TYPE: DNA
<213> ORGANISM: Artificial Sequence
<220> FEATURE:
<223> OTHER INFORMATION: Plasmid pLM718 complete sequence

<400> SEQUENCE: 21
gtgttggggc tgacttttgc tgccttgttg ggggggcga ttttaactga ggtcactttt        60
tcttggccgg gattgctaa tcgcttgtat gaggctatcc gtctgcggga ttatcccacg       120
gttcaagggg tggtggtatt tttggccgtt attgtggtgg cggctagttt ggcgatcgat       180
attttgaatg cttgtattga cccacggatt cgctattaat tccctgtcag aaaatatact       240
tagttattaa tacttagtta ttttttcttaa taaattttaa caaaccaaag ggcgttggca       300
gtgtataaag gatatttgaa ggggtgagaa ggaaggcgaa tgttgattta tgaagtttga       360
```

```
ttaacatttg tatcaaaata taaaattctt ctcataaacc ctgtacaatc ttttaagatt      420
tcggaaagtg ttctaggata ctgaagaaat gaaccacggg gcaattgtta aaagcctttg      480
tcgatggttc gccccggaag gggtcttagg aggtgacacc gatggattga ttgtcgtgat      540
cattcatggt gtgtccaatc ccaactcaac tctaagcaag tcaacaagta ggagataaat      600
ctatgttaga tgcctttgcc aaggtggttg ctcaagctga tgctcgcggc gaattcctga      660
ctaatgctca atttgatgca ctgtcgaact tagtgaaaga gggaaataaa agactagatg      720
ctgtcaatag gattacatcc aatgcgagca caatcgtagc gaatgccgct cgcgccctct      780
ttgccgaaca accacaatta attcagcctg gcggaaatgc gtataccaat cgacggatgg      840
ccgcctgttt acgcgatatg gaaattattt tgagatacgt tacttatgca attctcgccg      900
gtgattcgag tgttttagat gataggtgct taaacggttt gcgcgaaacc tatcaagccc      960
tcggaacccc cgggagttca gtagctgtcg ccatccagaa aatgaaggat gccgctatcg     1020
ccattgctaa tgatccaaac ggtattactc caggagattg ttctgcgcta atgtccgaga     1080
tcgccggata ctttgataga gcagctgctg ctgttgcgta atcaagcaga tccatagcat     1140
ataacaattg aaacagtttta gctgaagtct aagtgactgg acttctgttt gttacctaat     1200
tttttgtaaa ccaatcggga gataactcga gaatgaaaac ccccataacc gaagcaatcg     1260
cggctgctga cacacaagga agatttctat ctaacactga attacaggcc gttgatggaa     1320
ggtttaaaag agcggtggct agcatggaag ctgcccgggc tttgacaaac aacgcacagt     1380
ctttaataga tggagcagcc caggcggtct atcaaaaatt tccctataca acgacaatgc     1440
aagggagtca atatgcttct acgcctgaag gtaaagccaa atgtgcacgc gatattggct     1500
attatctccg gatgattact tactgtttag tagcgggtgg tacaggccct atggatgaat     1560
atctcattgc cggtttaagt gaaatcaatt ccactttcga tctatcaccc tcctggtaca     1620
tcgaagctct caagtatatt aaagctaatc atgggctcac tggacaagcc gccgttgaag     1680
caaatgcgta catagattac gctattaatg ctttaagcta acagccatcg agctagcaag     1740
cttggccgga tccggccgga tccgagtttt gtagaaacgc aaaaaggcca tccgtcagga     1800
tggccttctg cttaatttga tgcctggcag tttatggcgg gcgtcctgcc cgccacccct     1860
cgggccgttg cttcgcaacg ttcaaatccg ctcccggcgg atttgtccta ctcaggagag     1920
cgttcaccga caaacaacag ataaaacgaa aggcccagtc tttcgactga gcctttcgtt     1980
ttatttgaag tcaccccaac cgccttagtc ggtattcccc actgggtggg cgatacacga     2040
tttcccggaa aaattgaaaa aaattttgt ggcaggtgat atgatttgcg atcgaggtgg      2100
gtaagttaga actacagaaa acaaataacc tcatttcacc ccgaggagaa cgaattatga     2160
gggaagcggt gatcgccgaa gtatcgactc aactatcaga ggtagttggc gtcatcgagc     2220
gccatctcga accgacgttg ctggccgtac atttgtacgg ctccgcagtg gatggcggcc     2280
tgaagccaca cagtgatatt gatttgctgg ttacggtgac cgtaaggctt gatgaaacaa     2340
cgcggcgagc tttgatcaac gaccttttgg aaacttcggc ttccctggag agagcgaga      2400 ttctccgcgc tgtagaagtc accattgttg tgcacgacga catcattccg tggcgttatc     2460
cagctaagcg cgaactgcaa tttggagaat ggcagcgcaa tgacattctt gcaggtatct     2520
tcgagccagc cacgatcgac attgatctgg ctatcttgct gacaaaagca agagaacata     2580
gcgttgcctt ggtaggtcca gcggcggagg aactctttga tccggttcct gaacaggatc     2640
tatttgaggc gctaaatgaa accttaacgc tatggaactc gccgcccgac tgggctggcg     2700
```

```
atgagcgaaa tgtagtgctt acgttgtccc gcatttggta cagcgcagta accggcaaaa   2760
tcgcgccgaa ggatgtcgct gccgactggg caatggagcg cctgccggcc cagtatcagc   2820
ccgtcatact tgaagctaga caggcttatc ttggacaaga agaagatcgc ttggcctcgc   2880
gcgcagatca gttggaagaa tttgtccact acgtgaaagg cgagatcacc aaggtagtcg   2940
gcaaataaat gttgtcagtt aagtttatag gctgctatg gtatgataaa aaaatccccc   3000
cagcagttgg gggggaatga ttaattaggt attgaattgg ttaaattggt taattaaagg   3060
tgaaaacgta aaaatttatg aacttttggg attatatgtg aacttttta acgctaactc   3120
ccatttttgt cgatagtttg cacagggctg cttaaaatat gagcttaaca cctgaactca   3180
agatttttaa gcgaacagga gaaaaatcag tatggttggt ttagcagaag caagtcgcct   3240
aggaatcaga gcttttgaag agtctgagcg agtggaactg cgccctaact tcaccgaggg   3300
tgatgtccaa gctgtgattt gggctgcata tcgtcaggtg atgggtaatg aacacctgat   3360
gcaacgggag cgcttaacta gtgctgagtc tttgttgcgc cagggtgaaa ttacggtgcg   3420
ggattttgtg cgagccttag ctgtttcgga actgtaccgg aaaaagtttt tttatggcaa   3480
tagccaagtt cggtttattg aactgaacta taagcatttg ctgggtcggg ctcctttgga   3540
tgagtcagaa atggcgtttc acgttgatct gtataacgag gaaggctacg aggcggaaat   3600
taattcttac ctggattctc ctgagtattt ggagagtttc ggtgaaaatg tggtcccta   3660
ctaccgtggt tttgctaccc aacggggtca gtggactgtg gaatttaacc ggatttttcca  3720
actttaccgg ggatacgcga atagcgatcg cgcccagaac caaacccaag gacgtttaac   3780
ttgggaagtc gctcgcaata cttcttcgcc gatttgtcca gcaggtagcg gacaggctct   3840
ggtgggggcc aatggtggcg atcgcggtca attatatcgt gtggtagtag tacaaaaacc   3900
cacgcagttg acaccgagaa tgcgtaaagc tacagcagag tacacagtag cctacgagca   3960
actttcagga cagttgcagc ggatcaaccg catgggcgga cgggtcatca gcgtgacccc   4020
tgcttagaac agcaagttgt taactgttaa ccagttaata acaatagcat aatcaagtta   4080
gattgtctag gactaaagcc gcaagtaatt ccgttgtgat tataggagga tttaagtggc   4140
cattacaacc caatcgtctc ggttagggac aacagctttc caggagagtt ctccggtaga   4200
gttgcgtccc aattcacata cgcggccgcc tgggccttga gctcgaattt cctgcattaa   4260
tgaatcggcc aacgcgcggg gagaggcggt ttgcgtattg ggcgctcttc cgcttcctcg   4320
ctcactgact cgctgcgctc ggtcgttcgg ctgcggcgag cggtatcagc tcactcaaag   4380
gcggtaatac ggttatccac agaatcaggg gataacgcag gaaagaacat gtgagcaaaa   4440
ggccagcaaa aggccaggaa ccgtaaaaat agcggagtgt atactggctt actatgttgg   4500
cactgatgag ggtgtcagtg aagtgcttca tgtggcagga gaaaaaaggc tgcaccggtg   4560
cgtcagcaga atatgtgata caggatatat tccgcttcct cgctcactga ctcgctacgc   4620
tcggtcgttc gactgcggcg agcggaaatg gcttacgaac ggggcggaga tttcctggaa   4680
gatgccagga agatacttaa cagggaagtg agagggccgc ggcaaagccg ttttttccata   4740
ggctccgccc cctgacaag catcacgaaa tctgacgctc aaatcagtgg tggcgaaacc   4800
cgacaggact ataaagatac caggcgtttc cccctggcgg ctcccctcgtg cgctctcctg   4860
ttcctgcctt tcggtttacc ggtgtcattc cgctgttatg gccgcgtttg tctcattcca   4920
cgcctgacac tcagttccgg gtaggcagtt cgctccaagc tggactgtat gcacgaaccc   4980
cccattcagt ccgaccgctg cgccttatcc ggtaactatc gtcttgagtc caacccgaa   5040
agacatgcaa aagcaccact ggcagcagcc actggtaatt gatttagagg agttagtctt   5100
```

```
gaagtcatgc gccggttaag gctaaactga aggacaagt tttggtgact gcgctcctcc      5160
aagccagtta cctcggttca aagagttggt agctcagaga accttcgaaa aaccgccctg      5220
caaggcggtt ttttcgtttt cagagcaaga gattacgcgc agaccaaaac gatctcaaga      5280
agatcatctt attaagatta tcaaaaagga tcttcaccta gatccttta aattaaaaat       5340 gaagttttaa atcaatctaa agtatatatg agtaaacttg gtctgacagt taccaatgct      5400
taatcagtga ggcacctatc tcagcgatct gtctatttcg ttcatccata gttgcctgac      5460
tccccgtcgt gtagataact acgatacggg agggcttacc atctggcccc agtgctgcaa      5520
tgataccgcg ggacccacgc tcaccggctc cagatttatc agcaataaac cagccagccg      5580
gaagggccga gcgcagaagt ggtcctgcaa ctttatccgc ctccatccag tctattaatt       5640
gttgccggga agctagagta agtagttcgc cagttaatag tttgcgcaac gttgttgcca      5700
ttgctacagg catcgtggtg tcacgctcgt cgtttggtat ggcttcattc agctccggtt      5760
cccaacgatc aaggcgagtt acatgatccc ccatgttgtg caaaaaagcg gttagctcct      5820
tcggtcctcc gatcgttgtc agaagtaagt tggccgcagt gttatcactc atggttatgg      5880
cagcactgca taattctctt actgtcatgc catccgtaag atgcttttct gtgactggtg      5940
agtactcaac caagtcattc tgagaatagt gtatgcggcg accgagttgc tcttgcccgg      6000
cgtcaatacg ggataatacc gcgccacata gcagaacttt aaaagtgctc atcattggaa      6060
aacgttcttc ggggcgaaaa ctctcaagga tcttaccgct gttgagatcc agttcgatgt       6120
aacccactcg tgcacccaac tgatcttcag catcttttac tttcaccagc gtttctgggt      6180
gagcaaaaac aggaaggcaa aatgccgcaa aaagggaat aagggcgaca cggaaatgtt       6240
gaatactcat actcttcctt tttcaatatt attgaagcat ttatcagggt tattgtctca      6300
tgagcggata catatttgaa tgtatttaga aaaataaaca aatagggtt ccgcgcacat       6360 ttccccgaaa agtgccacct gacgtctaag aaaccattat tatcatgaca ttaacctata      6420
aaaataggcg tatcacgagg cccttcgtc tcgcgcgttt cggtgatgac ggtgaaaacc       6480
tctgacacat gcagctcccg gagacggtca cagcttgtct gtaagcggat gccaagcttg      6540
catgcctgca ggtggcgcgc cggggacgc ttatttggaa ttattactta ttcggttccc       6600 gcttttggg cggggatgct gttgcagttg attttttgcag tctggctggg ctggtttcct       6660
ttggggaatc gttttccggt gaccgtgact cctcctccta cttatagcgg actttatacc      6720
gttgatagtt tgttgagtgg caatttgggg actttctgga cgactatata ttatctgtgt      6780
ctaccctgtg tgactttggg cattttgctc agtgggattt tgagcgcat tgtccgcgtc       6840 aatttgagac aaactctaca agctgattat gtcgaggcgg cacgggcgcg aggagtgccg      6900
gagttacgga ttttgctggc tcatgctctc aaaaatgcca tgattcccgt tattact          6957
```

<210> SEQ ID NO 22
<211> LENGTH: 486
<212> TYPE: DNA
<213> ORGANISM: Artificial Sequence
<220> FEATURE:
<223> OTHER INFORMATION: Thermosynechococcus vulcanus apcA codon
      optimized DNA sequence

<400> SEQUENCE: 22

```
atgtccgtgg ttaccaagag catcgttaat gctgacgctg aagctcgtta cctgtccccc        60
ggcgaactgg atcgtatcaa aaacttcgtt tctaccggcg aacgtcgttt cgcgcattgct      120 caaaccctga ctgaaaaccg tgagcgtatc gttaaacagg ctggcgacca actgttccag      180
```

```
aagcgccctg atgttgtttc tcctggcggt aacgcttacg gtgaagaaat gactgctacc    240
tgcttgcgcg atctggatta ttacttgcgt ctggttactt atggtattgt ggctggtgac    300
gttactccta tcgaggaaat tggtctggtt ggcgttcgtg aaatgtataa ttctctgggt    360
actcccatcc ctgctgtggc tgaaggtatc cgcgctatga aaaatgttgc ttgctctctg    420
ttgtctgccg aagatgctgc cgaagctggc tcttatttcg acttcgttat tggcgctatg    480
caataa                                                              486
```

```
<210> SEQ ID NO 23
<211> LENGTH: 161
<212> TYPE: PRT
<213> ORGANISM: Thermosynechococcus vulcanus
<220> FEATURE:
<221> NAME/KEY: SITE
<222> LOCATION: (1)..(161)
<223> OTHER INFORMATION: Thermosynechococcus vulcanus apcA codon
      optimized protein sequence

<400> SEQUENCE: 23
```

```
Met Ser Val Val Thr Lys Ser Ile Val Asn Ala Asp Ala Glu Ala Arg
1               5                   10                  15

Tyr Leu Ser Pro Gly Glu Leu Asp Arg Ile Lys Asn Phe Val Ser Thr
            20                  25                  30

Gly Glu Arg Arg Leu Arg Ile Ala Gln Thr Leu Thr Glu Asn Arg Glu
        35                  40                  45

Arg Ile Val Lys Gln Ala Gly Asp Gln Leu Phe Gln Lys Arg Pro Asp
    50                  55                  60

Val Val Ser Pro Gly Gly Asn Ala Tyr Gly Glu Met Thr Ala Thr
65                  70                  75                  80

Cys Leu Arg Asp Leu Asp Tyr Tyr Leu Arg Leu Val Thr Tyr Gly Ile
                85                  90                  95

Val Ala Gly Asp Val Thr Pro Ile Glu Glu Ile Gly Leu Val Gly Val
            100                 105                 110

Arg Glu Met Tyr Asn Ser Leu Gly Thr Pro Ile Pro Ala Val Ala Glu
        115                 120                 125

Gly Ile Arg Ala Met Lys Asn Val Ala Cys Ser Leu Leu Ser Ala Glu
    130                 135                 140

Asp Ala Ala Glu Ala Gly Ser Tyr Phe Asp Phe Val Ile Gly Ala Met
145                 150                 155                 160

Gln
```

```
<210> SEQ ID NO 24
<211> LENGTH: 486
<212> TYPE: DNA
<213> ORGANISM: Artificial Sequence
<220> FEATURE:
<223> OTHER INFORMATION: Thermosynechococcus vulcanus apcB codon
      optimized DNA sequence

<400> SEQUENCE: 24
```

```
atgcaagatg ccatcaccgc tgttattaac gcttctgatg ttcaaggcaa atacctggac    60
accgctgcta tggaaaaact gaaagcttac ttcgccactg gcgaattgcg tgttcgtgcc   120
gcttctgtta tttccgccaa cgccgccaat atcgttaaag aagctgttgc taagagcctg   180
ctgtattctg acattactcg tcccggtggt aatatgtata ccaccccgtcg ttacgctgcc   240 tgtatccgcg atctggatta ctacttgcgt tatgctactt atgctatgct ggctggcgac   300
```

```
cccagcattc tggacgaacg tgtgctgaac ggtctgaaag aaacttacaa ctccctgggc    360
gttcccatcg ctgccactgt gcaggctatt caggctatga agaagtgac tgcctccttg     420 gttggtgccg atgccggtaa ggaaatgggc atctactttg actatatttg ttccggcctg    480
tcttaa                                                                486
```

```
<210> SEQ ID NO 25
<211> LENGTH: 161
<212> TYPE: PRT
<213> ORGANISM: Thermosynechococcus vulcanus
<220> FEATURE:
<221> NAME/KEY: SITE
<222> LOCATION: (1)..(161)
<223> OTHER INFORMATION: Thermosynechococcus vulcanus apcB codon
      optimized protein sequence

<400> SEQUENCE: 25

Met Gln Asp Ala Ile Thr Ala Val Ile Asn Ala Ser Asp Val Gln Gly
1               5                   10                  15

Lys Tyr Leu Asp Thr Ala Ala Met Glu Lys Leu Lys Ala Tyr Phe Ala
            20                  25                  30

Thr Gly Glu Leu Arg Val Arg Ala Ala Ser Val Ile Ser Ala Asn Ala
        35                  40                  45

Ala Asn Ile Val Lys Glu Ala Val Ala Lys Ser Leu Leu Tyr Ser Asp
    50                  55                  60

Ile Thr Arg Pro Gly Gly Asn Met Tyr Thr Thr Arg Arg Tyr Ala Ala
65                  70                  75                  80

Cys Ile Arg Asp Leu Asp Tyr Tyr Leu Arg Tyr Ala Thr Tyr Ala Met
                85                  90                  95

Leu Ala Gly Asp Pro Ser Ile Leu Asp Glu Arg Val Leu Asn Gly Leu
            100                 105                 110

Lys Glu Thr Tyr Asn Ser Leu Gly Val Pro Ile Ala Ala Thr Val Gln
        115                 120                 125

Ala Ile Gln Ala Met Lys Glu Val Thr Ala Ser Leu Val Gly Ala Asp
    130                 135                 140

Ala Gly Lys Glu Met Gly Ile Tyr Phe Asp Tyr Ile Cys Ser Gly Leu
145                 150                 155                 160

Ser
```

```
<210> SEQ ID NO 26
<211> LENGTH: 6967
<212> TYPE: DNA
<213> ORGANISM: Artificial Sequence
<220> FEATURE:
<223> OTHER INFORMATION: Plasmid plm655 sequence

<400> SEQUENCE: 26
ggaatcatga atcatcccac aactaagcat caaaaaatta catcctgtta ctggggaatt     60
tctgaactac ctgggttaga tacaggtaat attaaactcc tgaatcaatg tggtattgaa    120
aacacccagc aactgctcac gcgcgggagt aataatgcta ataaaatcgc cttatctaac    180
caactaggta tcaacatcag agatatcagt aaatgggtcg caatgtccga cttagccagg    240
gttcccagta ttggctatca atattgtggt gtccttttgc atagtggcgt aagttcagtt    300
aaccaactat ctcagatgtc tattcaacaa ctgcataaac agattttacg gctctatgta    360
ggaaccttgc aatctcgcca actctgtcca tctgttgatg tcatccaaac ctggattaaa    420
caagctaaaa ttttgcataa aattaattaa taattactag atgaaatcat gaattttcc     480
```

```
gaagatttgc gacaaaatgc accagccacc gaaagaaacc gcgaacctat tttagaggtc   540
ttaaaaaggg tgttgcccgc cacgggaacc gttttagaag tagccagcgg cacaggacaa   600
cacgcggttt ttttgctcc ccgtctctcc cctaggcggt ggctaccttc cgacccgcaa    660
cctttgttac aacagagtat taaagcatgg caaattcatt caccttcaga taatctttac   720
cctcccctac agttaaatgt agaagctaat ccttggccag tggaagggaa tgatttaccc   780
tgggaattat cggaatttcc catcactgct attgtagcaa ttaacctgat tcatatttcg   840
ccttggtcgg cttgtgaagg gttaatggcg ggaagcgatc gcattttgaa accgggggga   900
attttatatc tctatggacc ctataaaata gctggaaaac acaccgcacc tagtaacgct   960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaaccccccc attcagtccg  1800 accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaggatctt tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700 ttctccttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
```

```
gcgaaaactc tcaaggatct taccgctgtt gagatccagt tcgatgtaac ccactcgtgc    2940
acccaactga tcttcagcat cttttacttt caccagcgtt tctgggtgag caaaaacagg    3000
aaggcaaaat gccgcaaaaa agggaataag ggcgacacgg aaatgttgaa tactcatact    3060
cttccttttt caatattatt gaagcattta tcagggttat tgtctcatga gcggatacat    3120
atttgaatgt atttagaaaa ataaacaaat aggggttccg cgcacatttc cccgaaaagt    3180
gccacctgac gtctaagaaa ccattattat catgacatta acctataaaa ataggcgtat    3240
cacgaggccc tttcgtctcg cgcgtttcgg tgatgacggt gaaaacctct gacacatgca    3300
gctcccggag acggtcacag cttgtctgta agcggatgcc aagcttgcat gcctgcaggt    3360
ggcgcgccta gggggagga ttttatgatc ggatgttgag tcagtctgag tggtctaaaa    3420
ttcctacggt gggaattgtg tttgcggccg ccagggtgga tactctccct agggatagtt    3480
gggaccagcc tttggcggcg gtttgtacag aggagggtat atgggagttt ccaaaataac    3540
ttctggtggg ggggcaaatt atcgggcgat cgccacttat atggtattaa ttgctatagc    3600
gatcgctatg ctatttcccc tattttggtt ggtgggaact gcctttaaat cccctaccga    3660
aaacatcttt caggttcccc cccagtttat tccaagggaa cctactttca ctaattttgt    3720
cagagtttgg caaccaatc cctttggtcg ctatttattt aatagtaccc tcgtcgccct    3780
tttaaccgtc ggattaaatc tgctatttg ttccttggcg gcctatcctt tggcgcgctt    3840
aaacttttgg ggtcgcgatt ttctcctaag tgcgatcgtt tccaccatca tgatcccttt    3900
tcagattgtc atgattcccc tgtatattct agcagtacag ttaggattaa gaaatactta    3960
tttaggcatt atttttccat ctttagcctc cgcttttggc atctttctat tgcgacaggc    4020
atttatggga gttcccaaag agttagaaga agccgccaga attgatggct gttcagaatt    4080
agggatttgg tggcatatta tgatccctc agtccgtccc gccttaatga ccttagccat    4140
ttttgtattt atcgggtctt ggagtgattt tctctggccc ttaattgtag tcgatcgccc    4200
agaatattat accatcccct taggcgtggc aaatctagcc ggaactttt ctctcgattg    4260 gcggatagtc gccgccggtt ccgtcatttc tatcgctcct gtgttactac tatttttaat    4320
cgtacaacgg tatattgtgc ctacagatac agctacgggg gttaaggtt gaatgaggat    4380 tattaatctc agtcctaata atcaaaatca tatccaccag gcggcgactt tattagtcgc    4440
agaatttcgg gaaaattggc cgaatgcttg gccgacttat gaacgtggtt tagccgaggt    4500
tatggagtct tttggcgacg atagagttaa tctagtcgcc gtcgatgaaa atgataatct    4560
tctaggctgg attggtggta ttagccaata tcaaggccat gtttgggaat tacatccttt    4620
ggtagtcaaa agcgattatc aagggttagg aataggcga aaattggtcg ccaatttaga    4680
ggattatgtc cgctcacaag gagggttaac cttatggttg ggtaccgatg acgaaaataa    4740
tttaacctcc ctatctggtg tcgaattata ccccattttt ttggaaaata ttgctaacat    4800
aaaaaaccat ggtcgtcatc cctatgaatt ttatcagaaa tgcggttttg tgattatggg    4860
agtagtcccc gatgctaacg gtatcgggaa acctgatatt ttgatggcta aatctctgag    4920
aattgacaat catcctaaat ccaactgaat gttgtcagtt aagtttatag gctgctatg    4980 gtatgataaa aaaatccccc cagcagttgg ggggaatga ttaattaggt attgaattgg    5040
ttaaattgga ggtgtgttgg ggctgacttt tgctgccttg ttgggggggg cgattttaac    5100
tgaggtcact ttttcttggc cgggattggc taatcgcttg tatgaggcta tccgtctgcg    5160
ggattatccc acggttcaag gggtggtggt attttttggcc gttattgtgg tggcggctag    5220
```

```
tttggcgatc gatattttga atgcttgtat tgacccacgg attcgctatt aattccctgt    5280
cagaaaatat acttagttat taatacttag ttattttct taataaattt taacaaacca    5340
aagggcgttg gcagtgtata aaggatattt gaaggggtga gaaggaaggc gaatgttgat    5400
ttatgaagtt tgattaacat ttgtatcaaa atataaaatt cttctcataa accctgtaca    5460
atcttttaag atttcggaaa gtgttctagg atactgaaga aatgaaccac ggggcaattg    5520
ttaaaagcct ttgtcgatgg ttcgccccgg aaggggtctt aggaggtgac accgatggat    5580
tgattgtcgt gatcattcat ggtgtgtcca atcccaactc aactctaagc aagtcaacaa    5640
gtaggagata aatctatgtc cgtggttacc aagagcatcg ttaatgctga cgctgaagct    5700
cgttacctgt cccccggcga actggatcgt atcaaaaact tcgtttctac cggcgaacgt    5760
cgtttgcgca ttgctcaaac cctgactgaa accgtgagc gtatcgttaa acaggctggc    5820
gaccaactgt tccagaagcg ccctgatgtt gtttctcctg gcggtaacgc ttacggtgaa    5880
gaaatgactg ctacctgctt gcgcgatctg gattattact tgcgtctggt tacttatggt    5940
attgtggctg gtgacgttac tcctatcgag gaaattggtc tggttggcgt tcgtgaaatg    6000
tataattctc tgggtactcc catccctgct gtggctgaag gtatccgcgc tatgaaaaat    6060
gttgcttgct ctctgttgtc tgccgaagat gctgccgaag ctggctctta tttcgacttc    6120
gttattggcg ctatgcaata agcactggcg attatctctt atcaatcgac caagattcat    6180
ctaaacaatt cctagatcaa gcgaccatta gcaaacgaaa ccatcatgca agatgccatc    6240
accgctgtta ttaacgcttc tgatgttcaa ggcaaatacc tggacaccgc tgctatggaa    6300
aaactgaaag cttacttcgc cactggcgaa ttgcgtgttc gtgccgcttc tgttatttcc    6360
gccaacgccg ccaatatcgt taaagaagct gttgctaaga gcctgctgta ttctgacatt    6420
actcgtcccg gtggtaatat gtataccacc cgtcgttacg ctgcctgtat ccgcgatctg    6480
gattactact tgcgttatgc tacttatgct atgctggctg gcgacccag cattctggac    6540 gaacgtgtgc tgaacggtct gaaagaaact tacaactccc tgggcgttcc catcgctgcc    6600
actgtgcagg ctattcaggc tatgaaagaa gtgactgcct ccttggttgg tgccgatgcc    6660
ggtaaggaaa tgggcatcta ctttgactat atttgttccg gcctgtctta acagccaaat    6720
aaaacgaaag gctcagtcga aagactgggc cttttcgtttt atctgttgtt tgtcggtgaa    6780
cgctctcctg agtaggacaa atccgccggg agcggatttg aacgttgcga agcaacggcc    6840
cggagggtgg cgggcaggac gcccgccata aactgccagg catcaaatta gcagaaggc    6900 catcctgacg gatggccttt ttgcgtttct acaaactccg gatccggccg gcttgaagac    6960
agaatgc                                                             6967
```

<210> SEQ ID NO 27
<211> LENGTH: 486
<212> TYPE: DNA
<213> ORGANISM: Thermosynechococcus vulcanus
<220> FEATURE:
<221> NAME/KEY: misc_feature
<222> LOCATION: (1)..(486)
<223> OTHER INFORMATION: Thermosynechococcus vulcanus apcA DNA sequence

<400> SEQUENCE: 27

```
atgagcgtcg tcacgaaatc gatcgtgaat gcagatgccg aggcccgtta cctcagcccc     60
ggtgaactgg atcgcatcaa aaactttgtc agcaccggtg agcgccgtct gcgcattgcc    120 caaacccga cggaaaaccg cgagcgcatt gtcaagcaag cgggcgatca actcttccaa    180
aaacggcctg atgtggtatc ccccggtggc aatgcctacg gtgaagaaat gaccgccacc    240
```

```
tgcctgcgtg acctcgacta ttacctgcgg cttgtgacct acggtatcgt tgctggtgat        300 gtcacccca tcgaagaaat tggtttggtg ggtgtgcgtg aaatgtacaa ctccctcggt         360 accccattc cgctgtggc cgaagggatt cgcgccatga agaacgttgc ttgctcgctg          420
ctgtctgcgg aagatgccgc tgaagccggt tcttactttg acttcgtgat tggcgccatg       480
cagtag                                                                   486
```

```
<210> SEQ ID NO 28
<211> LENGTH: 161
<212> TYPE: PRT
<213> ORGANISM: Thermosynechococcus vulcanus
<220> FEATURE:
<221> NAME/KEY: SITE
<222> LOCATION: (1)..(161)
<223> OTHER INFORMATION: Thermosynechococcus vulcanus apcA protein
      sequence

<400> SEQUENCE: 28

Met Ser Val Val Thr Lys Ser Ile Val Asn Ala Asp Ala Glu Ala Arg
1               5                   10                  15

Tyr Leu Ser Pro Gly Glu Leu Asp Arg Ile Lys Asn Phe Val Ser Thr
            20                  25                  30

Gly Glu Arg Arg Leu Arg Ile Ala Gln Thr Leu Thr Glu Asn Arg Glu
        35                  40                  45

Arg Ile Val Lys Gln Ala Gly Asp Gln Leu Phe Gln Lys Arg Pro Asp
    50                  55                  60

Val Val Ser Pro Gly Gly Asn Ala Tyr Gly Glu Glu Met Thr Ala Thr
65                  70                  75                  80

Cys Leu Arg Asp Leu Asp Tyr Tyr Leu Arg Leu Val Thr Tyr Gly Ile
                85                  90                  95

Val Ala Gly Asp Val Thr Pro Ile Glu Glu Ile Gly Leu Val Gly Val
            100                 105                 110

Arg Glu Met Tyr Asn Ser Leu Gly Thr Pro Ile Pro Ala Val Ala Glu
        115                 120                 125

Gly Ile Arg Ala Met Lys Asn Val Ala Cys Ser Leu Leu Ser Ala Glu
    130                 135                 140

Asp Ala Glu Ala Gly Ser Tyr Phe Asp Phe Val Ile Gly Ala Met
145                 150                 155                 160

Gln
```

```
<210> SEQ ID NO 29
<211> LENGTH: 486
<212> TYPE: DNA
<213> ORGANISM: Thermosynechococcus vulcanus
<220> FEATURE:
<221> NAME/KEY: misc_feature
<222> LOCATION: (1)..(486)
<223> OTHER INFORMATION: Thermosynechococcus vulcanus apcB DNA sequence

<400> SEQUENCE: 29
atgcaagacg cgattaccgc tgtcatcaac gcctctgacg tacaaggcaa ataccttgac       60
actgccgcca tggagaagct gaaagcttac ttcgccactg cgaactgcg gtgcgggct        120 gcgagtgtaa tcagtgccaa tgccgccaac attgtcaaag aagcagtggc caaatccctg     180
ctgtactctg acatcacccg tcccggtggc aatatgtaca ccactcgtcg ctatgcagcc     240
tgtatccgcg acctcgacta ctacctgcgc tatgccacct atgccatgtt ggcggggat      300 ccttctatcc tcgatgagcg ggtgctcaat gggttgaaag aaacctacaa ctccttgggc     360
```

```
gtgcccatcg ctgccacggt gcaagccatc caagccatga agaagtcac tgccagcttg      420 gtgggtgcgg atgccggcaa agaaatgggc atctactttg actacatctg ctctggctta      480
agctag                                                                  486
```

```
<210> SEQ ID NO 30
<211> LENGTH: 161
<212> TYPE: PRT
<213> ORGANISM: Thermosynechococcus vulcanus
<220> FEATURE:
<221> NAME/KEY: SITE
<222> LOCATION: (1)..(161)
<223> OTHER INFORMATION: Thermosynechococcus vulcanus apcB protein
      sequence

<400> SEQUENCE: 30

Met Gln Asp Ala Ile Thr Ala Val Ile Asn Ala Ser Asp Val Gln Gly
1               5                   10                  15

Lys Tyr Leu Asp Thr Ala Ala Met Glu Lys Leu Lys Ala Tyr Phe Ala
            20                  25                  30

Thr Gly Glu Leu Arg Val Arg Ala Ala Ser Val Ile Ser Ala Asn Ala
        35                  40                  45

Ala Asn Ile Val Lys Glu Ala Val Ala Lys Ser Leu Leu Tyr Ser Asp
    50                  55                  60

Ile Thr Arg Pro Gly Gly Asn Met Tyr Thr Thr Arg Arg Tyr Ala Ala
65                  70                  75                  80

Cys Ile Arg Asp Leu Asp Tyr Tyr Leu Arg Tyr Ala Thr Tyr Ala Met
                85                  90                  95

Leu Ala Gly Asp Pro Ser Ile Leu Asp Glu Arg Val Leu Asn Gly Leu
            100                 105                 110

Lys Glu Thr Tyr Asn Ser Leu Gly Val Pro Ile Ala Ala Thr Val Gln
        115                 120                 125

Ala Ile Gln Ala Met Lys Glu Val Thr Ala Ser Leu Val Gly Ala Asp
    130                 135                 140

Ala Gly Lys Glu Met Gly Ile Tyr Phe Asp Tyr Ile Cys Ser Gly Leu
145                 150                 155                 160

Ser
```

```
<210> SEQ ID NO 31
<211> LENGTH: 6652
<212> TYPE: DNA
<213> ORGANISM: Artificial Sequence
<220> FEATURE:
<223> OTHER INFORMATION: Plasmid pLM1007 sequence

<400> SEQUENCE: 31
ggaatcatga atcatcccac aactaagcat caaaaaatta catcctgtta ctggggaatt       60
tctgaactac ctgggttaga tacaggtaat attaaactcc tgaatcaatg tggtattgaa      120
aacacccagc aactgctcac gcgcgggagt aataatgcta ataaaatcgc cttatctaac      180
caactaggta tcaacatcag agatatcagt aaatgggtcg caatgtccga cttagccagg      240
gttcccagta ttggctatca atattgtggt gtccttttgc atagtggcgt aagttcagtt      300
aaccaactat ctcagatgtc tattcaacaa ctgcataaac agattttacg gctctatgta      360
ggaaccttgc aatctcgcca actctgtcca tctgttgatg tcatccaaac ctggattaaa      420
caagctaaaa ttttgcataa aattaattaa taattactag atgaaatcat gaattttcc      480 gaagatttgc gacaaaatgc accagccacc gaaagaaacc gcgaacctat tttagaggtc      540
```

```
ttaaaaaggg tgttgcccgc cacgggaacc gttttagaag tagccagcgg cacaggacaa    600
cacgcggttt ttttgctcc ccgtctctcc cctaggcggt ggctaccttc cgacccgcaa     660
cctttgttac aacagagtat taaagcatgg caaattcatt caccttcaga taatctttac    720
cctcccctac agttaaatgt agaagctaat ccttggccag tggaagggaa tgatttaccc    780
tgggaattat cggaatttcc catcactgct attgtagcaa ttaacctgat tcatatttcg    840
ccttggtcgg cttgtgaagg gttaatggcg ggaagcgatc gcattttgaa accgggggga    900
attttatatc tctatggacc ctataaaata gctggaaaac acaccgcacc tagtaacgct    960
tcctttgatg aatatttgcg aacttctaac cctaagtggg gtgtcagaaa ccttgatgat   1020
tcacatacgc ggccgcctgg gccttgagct cgaatttcct gcattaatga atcggccaac   1080
gcgcggggag aggcggtttg cgtattgggc gctcttccgc ttcctcgctc actgactcgc   1140
tgcgctcggt cgttcggctg cggcgagcgg tatcagctca ctcaaaggcg gtaatacggt   1200
tatccacaga atcaggggat aacgcaggaa agaacatgtg agcaaaaggc cagcaaaagg   1260
ccaggaaccg taaaaatagc ggagtgtata ctggcttact atgttggcac tgatgagggt   1320
gtcagtgaag tgcttcatgt ggcaggagaa aaaaggctgc accggtgcgt cagcagaata   1380
tgtgatacag gatatattcc gcttcctcgc tcactgactc gctacgctcg gtcgttcgac   1440
tgcggcgagc ggaaatggct tacgaacggg gcggagattt cctggaagat gccaggaaga   1500
tacttaacag ggaagtgaga gggccgcggc aaagccgttt ttccataggc tccgcccccc   1560
tgacaagcat cacgaaatct gacgctcaaa tcagtggtgg cgaaacccga caggactata   1620
aagataccag gcgtttcccc ctggcggctc cctcgtgcgc tctcctgttc ctgcctttcg   1680
gtttaccggt gtcattccgc tgttatggcc gcgtttgtct cattccacgc ctgacactca   1740
gttccgggta ggcagttcgc tccaagctgg actgtatgca cgaaccccc attcagtccg    1800 accgctgcgc cttatccggt aactatcgtc ttgagtccaa cccggaaaga catgcaaaag   1860
caccactggc agcagccact ggtaattgat ttagaggagt tagtcttgaa gtcatgcgcc   1920
ggttaaggct aaactgaaag gacaagtttt ggtgactgcg ctcctccaag ccagttacct   1980
cggttcaaag agttggtagc tcagagaacc ttcgaaaaac cgccctgcaa ggcggttttt   2040
tcgttttcag agcaagagat tacgcgcaga ccaaaacgat ctcaagaaga tcatcttatt   2100
aagattatca aaaggatctt tcacctagat cctttttaaat taaaaatgaa gttttaaatc   2160
aatctaaagt atatatgagt aaacttggtc tgacagttac caatgcttaa tcagtgaggc   2220
acctatctca gcgatctgtc tatttcgttc atccatagtt gcctgactcc ccgtcgtgta   2280
gataactacg atacgggagg gcttaccatc tggccccagt gctgcaatga taccgcggga   2340
cccacgctca ccggctccag atttatcagc aataaaccag ccagccggaa gggccgagcg   2400
cagaagtggt cctgcaactt tatccgcctc catccagtct attaattgtt gccgggaagc   2460
tagagtaagt agttcgccag ttaatagttt gcgcaacgtt gttgccattg ctacaggcat   2520
cgtggtgtca cgctcgtcgt ttggtatggc ttcattcagc tccggttccc aacgatcaag   2580
gcgagttaca tgatcccca tgttgtgcaa aaaagcggtt agctccttcg gtcctccgat   2640
cgttgtcaga agtaagttgg ccgcagtgtt atcactcatg gttatggcag cactgcataa   2700
ttctcttact gtcatgccat ccgtaagatg cttttctgtg actggtgagt actcaaccaa   2760
gtcattctga atagtgtata tgcggcgacc gagttgctct tgcccggcgt caatacggga   2820
taataccgcg ccacatagca gaactttaaa agtgctcatc attggaaaac gttcttcggg   2880
```

```
gcgaaaactc tcaaggatct taccgctgtt gagatccagt tcgatgtaac ccactcgtgc   2940
acccaactga tcttcagcat cttttacttt caccagcgtt tctgggtgag caaaaacagg   3000
aaggcaaaat gccgcaaaaa agggaataag ggcgacacgg aaatgttgaa tactcatact   3060 cttcctttt caatattatt gaagcattta tcagggttat tgtctcatga gcggatacat   3120
atttgaatgt atttagaaaa ataaacaaat aggggttccg cgcacatttc cccgaaaagt   3180
gccacctgac gtctaagaaa ccattattat catgacatta acctataaaa ataggcgtat   3240
cacgaggccc tttcgtctcg cgcgtttcgg tgatgacggt gaaaacctct gacacatgca   3300
gctcccggag acggtcacag cttgtctgta agcggatgcc aagcttgcat gcctgcaggt   3360
ggcgcgccta tggggaggga ttttatgatc ggatgttgag tcagtctgag tggtctaaaa   3420
ttcctacggt gggaattgtg tttgcggccg ccagggtgga tactctccct agggatagtt   3480
gggaccagcc tttggcggcg gtttgtacag aggagggtat atgggagttt ccaaaataac   3540
ttctggtggg ggggcaaatt atcgggcgat cgccacttat atggtattaa ttgctatagc   3600
gatcgctatg ctatttcccc tattttggtt ggtgggaact gcctttaaat ccctaccga   3660 aaacatcttt caggttcccc cccagtttat tccaagggaa cctactttca ctaattttgt   3720
cagagtttgg caaccaatc cctttggtcg ctatttattt aatagtaccc tcgtcgccct   3780
tttaaccgtc ggattaaatc tgctattttg ttccttggcg gcctatcctt ggcgcgctt   3840 aaacttttgg ggtcgcgatt ttctcctaag tgcgatcgtt tccaccatca tgataccctt   3900
tcagattgtc atgattcccc tgtatattct agcagtacag ttaggattaa gaaatactta   3960
tttaggcatt atttttccat cttagcctc cgcttttggc atctttctat gcgacaggc   4020 atttatggga gttcccaaag agttagaaga agccgccaga attgatggct gttcagaatt   4080
agggatttgg tggcatatta tgatcccctc agtccgtccc gccttaatga ccttagccat   4140 ttttgtatttt atcgggtctt ggagtgattt tctctggccc ttaattgtag tcgatcgccc   4200
agaatattat accatccctt taggcgtggc aaatctagcc ggaacttttt ctctcgattg   4260
gcggatagtc gccgccggtt ccgtcatttc tatcgctcct gtgttactac tattttaat   4320 cgtacaacgg tatattgtgc ctacagatac agctacgggg gttaaaggtt gaatgaggat   4380
tattaatctc agtcctaata atcaaaatca tatccaccag gcggcgactt tattagtcgc   4440
agaatttcgg gaaaattggc cgaatgcttg gccgacttat gaacgtggtt tagccgaggt   4500
tatggagtct tttggcgacg atagagttaa tctagtcgcc gtcgatgaaa atgataatct   4560
tctaggctgg attggtggta ttagccaata tcaaggccat gttttgggaat tacatccttt   4620 ggtagtcaaa agcgattatc aagggttagg aatagggcga aaattggtcg ccaatttaga   4680
ggattatgtc cgctcacaag gagggttaac cttatggttg ggtaccgatg acgaaaataa   4740
tttaacctcc ctatctggtg tcgaattata cccccatttt ttggaaaata ttgctaacat   4800
aaaaaaccat ggtcgtcatc cctatgaatt ttatcagaaa tgcggttttg tgattatggg   4860
agtagtcccc gatgctaacg gtatcgggaa acctgatatt ttgatggcta aatctctgag   4920
aattgacaat catcctaaat ccaactgaat gttgtcagtt aagtttatag ggctgctatg   4980
gtatgataaa aaaatccccc cagcagttgg ggggaatga ttaattaggt attgaattgg   5040
ttaaattgga ggtttgaagg ggtgagaagg aaggcgaatg ttgatttatg aagtttgatt   5100
aacatttgta tcaaaatata aaattcttct cataaaccct gtacaatctt ttaagatttc   5160
ggaaagtgtt ctaggatact gaagaaatga accacgggc aattgttaaa agcctttgtc   5220
gatggttcgc cccggaaggg gtcttaggag gtgacaccga tggattgatt gtcgtgatca   5280
```

```
                                      -continued ttcatggtgt gtccaatccc aactcaactc taagcaagtc aacaagtagg agataaatct    5340
atgagcgtcg tcacgaaatc gatcgtgaat gcagatgccg aggcccgtta cctcagcccc    5400
ggtgaactgg atcgcatcaa aaactttgtc agcaccggtg agcgccgtct gcgcattgcc    5460
caaaccctga cggaaaaccg cgagcgcatt gtcaagcaag cgggcgatca actcttccaa    5520
aaacggcctg atgtggtatc ccccggtggc aatgcctacg gtgaagaaat gaccgccacc    5580
tgcctgcgtg acctcgacta ttacctgcgg cttgtgacct acggtatcgt tgctggtgat    5640
gtcaccccca tcgaagaaat tggtttggtg ggtgtgcgtg aaatgtacaa ctccctcggt    5700 accccccattc ccgctgtggc cgaagggatt cgcgccatga agaacgttgc ttgctcgctg    5760
ctgtctgcgg aagatgccgc tgaagccggt tcttactttg acttcgtgat ggcgccatg    5820 cagtaggcac tggcgattat ctcttatcaa tcgaccaaga ttcatctaaa caattcctag    5880
atcaagcgac cattagcaaa cgaaaccatc atgcaagacg cgattaccgc tgtcatcaac    5940
gcctctgacg tacaaggcaa ataccctcgac actgccgcca tggagaagct gaaagcttac    6000
ttcgccactg gcgaactgcg ggtgcgggct gcgagtgtaa tcagtgccaa tgccgccaac    6060
attgtcaaag aagcagtggc caaatccctg ctgtactctg acatcacccg tcccggtggc    6120
aatatgtaca ccactcgtcg ctatgcagcc tgtatccgcg acctcgacta ctacctgcgc    6180
tatgccacct atgccatgtt ggcggggat ccttctatcc tcgatgagcg ggtgctcaat    6240
gggttgaaag aaacctacaa ctccttgggc gtgcccatcg ctgccacggt gcaagccatc    6300
caagccatga agaagtcac tgccagcttg gtgggtgcgg atgccggcaa agaaatgggc    6360
atctactttg actacatctg ctctggctta agctagcagc caaataaaac gaaaggctca    6420
gtcgaaagac tgggccttc gttttatctg ttgtttgtcg gtgaacgctc tcctgagtag    6480
gacaaatccg ccgggagcgg atttgaacgt tgcgaagcaa cggcccggag ggtggcgggc    6540
aggacgcccg ccataaactg ccaggcatca aattaagcag aaggccatcc tgacggatgg    6600 ccttttttgcg tttctacaaa ctccggatcc ggccggcttg aagacagaat gc           6652

<210> SEQ ID NO 32
<211> LENGTH: 486
<212> TYPE: DNA
<213> ORGANISM: Artificial Sequence
<220> FEATURE:
<223> OTHER INFORMATION: Thermosynechococcus vulcanus apcB codon
      optimized DNA sequence

<400> SEQUENCE: 32
atgcaagatg ccatcaccgc tgttattaac gcttctgatg ttcaaggcaa ataccctggac     60 accgctgcta tggaaaaact gaaagcttac ttcgccactg gcgaattgcg tgttcgtgcc    120
gcttctgtta tttccgccaa cgccgccaat atcgttaaag aagctgttgc taagagcctg    180
ctgtattctg acattactcg tcccggtggt aatatgtata ccacccgtcg ttacgctgcc    240
tgtatccgcg atctggatta ctacttgcgt tatgctactt atgctatgct ggctggcgac    300
cccagcattc tggacgaacg tgtgctgaac ggtctgaaag aaacttacaa ctccctgggc    360
gttcccatcg ctgccactgt gcaggctatt caggctatga aagaagtgac tgcctccttg    420
gttggtgccg atgccggtaa ggaaatgggc atctactttg actatatttg ttccggcctg    480
tcttaa                                                              486

<210> SEQ ID NO 33
<211> LENGTH: 161
```

```
<212> TYPE: PRT
<213> ORGANISM: Thermosynechococcus vulcanus
<220> FEATURE:
<221> NAME/KEY: SITE
<222> LOCATION: (1)..(161)
<223> OTHER INFORMATION: Thermosynechococcus vulcanus apcB codon
      optimized protein sequence

<400> SEQUENCE: 33

Met Gln Asp Ala Ile Thr Ala Val Ile Asn Ala Ser Asp Val Gln Gly
1               5                   10                  15

Lys Tyr Leu Asp Thr Ala Ala Met Glu Lys Leu Lys Ala Tyr Phe Ala
            20                  25                  30

Thr Gly Glu Leu Arg Val Arg Ala Ala Ser Val Ile Ser Ala Asn Ala
        35                  40                  45

Ala Asn Ile Val Lys Glu Ala Val Ala Lys Ser Leu Leu Tyr Ser Asp
    50                  55                  60

Ile Thr Arg Pro Gly Gly Asn Met Tyr Thr Thr Arg Arg Tyr Ala Ala
65                  70                  75                  80

Cys Ile Arg Asp Leu Asp Tyr Tyr Leu Arg Tyr Ala Thr Tyr Ala Met
                85                  90                  95

Leu Ala Gly Asp Pro Ser Ile Leu Asp Glu Arg Val Leu Asn Gly Leu
            100                 105                 110

Lys Glu Thr Tyr Asn Ser Leu Gly Val Pro Ile Ala Ala Thr Val Gln
        115                 120                 125

Ala Ile Gln Ala Met Lys Glu Val Thr Ala Ser Leu Val Gly Ala Asp
    130                 135                 140

Ala Gly Lys Glu Met Gly Ile Tyr Phe Asp Tyr Ile Cys Ser Gly Leu
145                 150                 155                 160

Ser

<210> SEQ ID NO 34
<211> LENGTH: 6652
<212> TYPE: DNA
<213> ORGANISM: Artificial Sequence
<220> FEATURE:
<223> OTHER INFORMATION: Plasmid pLM1008 sequence

<400> SEQUENCE: 34
ggaatcatga atcatcccac aactaagcat caaaaaatta catcctgtta ctggggaatt      60
tctgaactac ctgggttaga tacaggtaat attaaactcc tgaatcaatg tggtattgaa     120
aacacccagc aactgctcac gcgcgggagt aataatgcta ataaaatcgc cttatctaac     180
caactaggta tcaacatcag agatatcagt aaatgggtcg caatgtccga cttagccagg     240
gttcccagta ttggctatca atattgtggt gtccttttgc atagtggcgt aagttcagtt     300
aaccaactat ctcagatgtc tattcaacaa ctgcataaac agattttacg gctctatgta     360
ggaaccttgc aatctcgcca actctgtcca tctgttgatg tcatccaaac ctggattaaa     420
caagctaaaa ttttgcataa aattaattaa taattactag atgaaatcat gaattttttcc    480 gaagatttgc gacaaaatgc accagccacc gaaagaaacc gcgaacctat tttagaggtc     540
ttaaaagggt gttgcccgc cacgggaacc gttttagaag tagccagcgg cacaggacaa      600
cacgcggttt ttttgctcc ccgtctctcc cctaggcggt ggctaccttc gacccgcaa       660 ccttttgttac aacagagtat taaagcatgg caaattcatt caccttcaga taatctttac    720
cctcccctac agttaaatgt agaagctaat ccttggccag tggaagggaa tgatttaccc     780
tgggaattat cggaatttcc catcactgct attgtagcaa ttaacctgat tcatatttcg     840
```

```
ccttggtcgg cttgtgaagg gttaatggcg ggaagcgatc gcattttgaa accgggggga      900
attttatatc tctatggacc ctataaaata gctggaaaac acaccgcacc tagtaacgct      960
tcctttgatg aatatttgcg aacttctaac cctaagtggg gtgtcagaaa ccttgatgat     1020
tcacatacgc ggccgcctgg gccttgagct cgaatttcct gcattaatga atcggccaac     1080
gcgcggggag aggcggtttg cgtattgggc gctcttccgc ttcctcgctc actgactcgc     1140
tgcgctcggt cgttcggctg cggcgagcgg tatcagctca ctcaaaggcg gtaatacggt     1200
tatccacaga atcaggggat aacgcaggaa agaacatgtg agcaaaaggc cagcaaaagg     1260
ccaggaaccg taaaaatagc ggagtgtata ctggcttact atgttggcac tgatgagggt     1320
gtcagtgaag tgcttcatgt ggcaggagaa aaaaggctgc accggtgcgt cagcagaata     1380
tgtgatacag gatatattcc gcttcctcgc tcactgactc gctacgctcg gtcgttcgac     1440
tgcggcgagc ggaaatggct tacgaacggg gcggagattt cctggaagat gccaggaaga     1500
tacttaacag ggaagtgaga gggccgcggc aaagccgttt ttccataggc tccgccccc      1560
tgacaagcat cacgaaatct gacgctcaaa tcagtggtgg cgaaacccga caggactata     1620
aagataccag gcgtttcccc ctggcggctc cctcgtgcgc tctcctgttc ctgcctttcg     1680
gtttaccggt gtcattccgc tgttatggcc gcgtttgtct cattccacgc ctgacactca     1740
gttccgggta ggcagttcgc tccaagctgg actgtatgca cgaaccccc  attcagtccg     1800
accgctgcgc cttatccggt aactatcgtc ttgagtccaa cccggaaaga catgcaaaag     1860
caccactggc agcagccact ggtaattgat ttagaggagt tagtcttgaa gtcatgcgcc     1920
ggttaaggct aaactgaaag gacaagtttt ggtgactgcg ctcctccaag ccagttacct     1980
cggttcaaag agttggtagc tcagagaacc ttcgaaaaac cgccctgcaa ggcggttttt     2040
tcgttttcag agcaagagat tacgcgcaga ccaaaacgat ctcaagaaga tcatcttatt     2100
aagattatca aaaaggatct tcacctagat ccttttaaat taaaaatgaa gttttaaatc     2160
aatctaaagt atatatgagt aaacttggtc tgacagttac caatgcttaa tcagtgaggc     2220
acctatctca gcgatctgtc tatttcgttc atccatagtt gcctgactcc ccgtcgtgta     2280
gataactacg atacgggagg gcttaccatc tggccccagt gctgcaatga taccgcggga     2340
cccacgctca ccggctccag atttatcagc aataaaccag ccagccggaa gggccgagcg     2400
cagaagtggt cctgcaactt tatccgcctc catccagtct attaattgtt gccgggaagc     2460
tagagtaagt agttcgccag ttaatagttt gcgcaacgtt gttgccattg ctacaggcat     2520
cgtggtgtca cgctcgtcgt ttggtatggc ttcattcagc tccggttccc aacgatcaag     2580
gcgagttaca tgatccccca tgttgtgcaa aaaagcggtt agctccttcg gtcctccgat     2640
cgttgtcaga agtaagttgg ccgcagtgtt atcactcatg gttatggcag cactgcataa     2700
ttctcttact gtcatgccat ccgtaagatg cttttctgtg actggtgagt actcaaccaa     2760
gtcattctga gaatagtgta tgcggcgacc gagttgctct tgcccggcgt caatacggga     2820
taataccgcg ccacatagca gaactttaaa agtgctcatc attggaaaac gttcttcggg     2880
gcgaaaactc tcaaggatct taccgctgtt gagatccagt tcgatgtaac ccactcgtgc     2940
acccaactga tcttcagcat cttttacttt caccagcgtt tctgggtgag caaaaacagg     3000
aaggcaaaat gccgcaaaaa agggaataag ggcgacacgg aaatgttgaa tactcatact     3060
cttcctttt  caatattatt gaagcattta tcagggttat tgtctcatga gcggatacat     3120
atttgaatgt atttagaaaa ataaacaaat aggggttccg cgcacatttc cccgaaaagt     3180
```

```
gccacctgac gtctaagaaa ccattattat catgacatta acctataaaa ataggcgtat    3240
cacgaggccc tttcgtctcg cgcgtttcgg tgatgacggt gaaaacctct gacacatgca    3300
gctcccggag acggtcacag cttgtctgta agcggatgcc aagcttgcat gcctgcaggt    3360
ggcgcgccta tggggagga ttttatgatc ggatgttgag tcagtctgag tggtctaaaa    3420
ttcctacggt gggaattgtg tttgcggccg ccagggtgga tactctccct agggatagtt    3480
gggaccagcc tttggcggcg gtttgtacag aggagggtat atgggagttt ccaaaataac    3540
ttctggtggg ggggcaaatt atcgggcgat cgccacttat atggtattaa ttgctatagc    3600
gatcgctatg ctatttcccc tattttggtt ggtgggaact gcctttaaat cccctaccga    3660
aaacatcttt caggttcccc cccagtttat tccaagggaa cctactttca ctaattttgt    3720
cagagtttgg caaaccaatc cctttggtcg ctatttattt aatagtaccc tcgtcgccct    3780
tttaaccgtc ggattaaatc tgctattttg ttccttggcg gcctatcctt tggcgcgctt    3840
aaacttttgg ggtcgcgatt ttctcctaag tgcgatcgtt tccaccatca tgataccctt    3900
tcagattgtc atgattcccc tgtatattct agcagtacag ttaggattaa gaaatactta    3960
tttaggcatt attttccat ctttagcctc cgcttttggc atctttctat tgcgacaggc    4020
atttatggga gttcccaaag agttagaaga agccgccaga attgatggct gttcagaatt    4080
agggatttgg tggcatatta tgatcccctc agtccgtccc gccttaatga ccttagccat    4140
ttttgtattt atcgggtctt ggagtgattt tctctggccc ttaattgtag tcgatcgccc    4200
agaatattat accatccctt taggcgtggc aaatctagcc ggaacttttt ctctcgattg    4260
gcggatagtc gccgccggtt ccgtcatttc tatcgctcct gtgttactac tatttttaat    4320
cgtacaacgg tatattgtgc ctacagatac agctacgggg gttaaaggtt gaatgaggat    4380
tattaatctc agtcctaata atcaaaatca tatccaccag gcggcgactt tattagtcgc    4440
agaatttcgg gaaaattggc cgaatgcttg gccgacttat gaacgtggtt tagccgaggt    4500 tatgagtct tttggcgacg atagagttaa tctagtcgcc gtcgatgaaa atgataatct    4560
tctaggctgg attggtggta ttagccaata tcaaggccat gtttgggaat tacatccttt    4620
ggtagtcaaa agcgattatc aagggttagg aatagggcga aaattggtcg ccaatttaga    4680
ggattatgtc cgctcacaag gagggttaac cttatggttg ggtaccgatg acgaaaataa    4740
tttaacctcc ctatctggtg tcgaattata cccccatttt ttggaaaata ttgctaacat    4800
aaaaaaccat ggtcgtcatc cctatgaatt ttatcagaaa tgcggttttg tgattatggg    4860
agtagtcccc gatgctaacg gtatcgggaa acctgatatt ttgatggcta atctctgag    4920 aattgacaat catcctaaat ccaactgaat gttgtcagtt aagtttatag ggctgctatg    4980
gtatgataaa aaaatccccc cagcagttgg ggggaatga ttaattaggt attgaattgg    5040
ttaaattgga ggtttgaagg ggtgagaagg aaggcgaatg ttgatttatg aagtttgatt    5100
aacatttgta tcaaaatata aaattcttct cataaaccct gtacaatctt ttaagatttc    5160
ggaaagtgtt ctaggatact gaagaaatga accacgggc aattgttaaa agcctttgtc    5220
gatggttcgc cccggaaggg gtcttaggag gtgacaccga tggattgatt gtcgtgatca    5280
ttcatggtgt gtccaatccc aactcaactc taagcaagtc aacaagtagg agataaatct    5340
atgtccgtgg ttaccaagag catcgttaat gctgacgctg aagctcgtta cctgtccccc    5400
ggcgaactgg atcgtatcaa aaacttcgtt tctaccggcg aacgtcgttt gcgcattgct    5460
caaaccctga ctgaaaaccg tgagcgtatc gttaaacagg ctggcgacca actgttccag    5520
aagcgccctg atgttgtttc tcctggcggt aacgcttacg gtgaagaaat gactgctacc    5580
```

```
tgcttgcgcg atctggatta ttacttgcgt ctggttactt atggtattgt ggctggtgac    5640
gttactccta tcgaggaaat tggtctggtt ggcgttcgtg aaatgtataa ttctctgggt    5700
actcccatcc ctgctgtggc tgaaggtatc cgcgctatga aaatgttgc ttgctctctg     5760 ttgtctgccg aagatgctgc cgaagctggc tcttatttcg acttcgttat tggcgctatg    5820
caataagcac tggcgattat ctcttatcaa tcgaccaaga ttcatctaaa caattcctag    5880
atcaagcgac cattagcaaa cgaaaccatc atgcaagatg ccatcaccgc tgttattaac    5940
gcttctgatg ttcaaggcaa atacctggac accgctgcta tggaaaaact gaaagcttac    6000
ttcgccactg gcgaattgcg tgttcgtgcc gcttctgtta tttccgccaa cgccgccaat    6060
atcgttaaag aagctgttgc taagagcctg ctgtattctg acattactcg tcccggtggt    6120
aatatgtata ccacccgtcg ttacgctgcc tgtatccgcg atctggatta ctacttgcgt    6180
tatgctactt atgctatgct ggctggcgac cccagcattc tggacgaacg tgtgctgaac    6240
ggtctgaaag aaacttacaa ctccctgggc gttcccatcg ctgccactgt gcaggctatt    6300
caggctatga agaagtgac tgcctccttg gttggtgccg atgccggtaa ggaaatgggc    6360
atctactttg actatatttg ttccggcctg tcttaacagc caaataaaac gaaaggctca    6420
gtcgaaagac tgggcctttc gttttatctg ttgtttgtcg gtgaacgctc tcctgagtag    6480
gacaaatccg ccgggagcgg atttgaacgt tgcgaagcaa cggccggag ggtggcgggc     6540 aggacgcccg ccataaactg ccaggcatca aattaagcag aaggccatcc tgacggatgg    6600 ccttttttgcg tttctacaaa ctccggatcc ggccggcttg aagacagaat gc            6652
```

<210> SEQ ID NO 35
<211> LENGTH: 162
<212> TYPE: PRT
<213> ORGANISM: Pseudanabaena sp.

<400> SEQUENCE: 35

```
Met Lys Thr Pro Leu Thr Glu Ala Val Ser Ala Ala Asp Ser Gln Gly
 1               5                  10                  15

Arg Phe Leu Ser Thr Thr Glu Thr Gln Val Ala Phe Gly Arg Phe Arg
            20                  25                  30

Gln Ala Thr Ser Gly Leu Ala Ala Ala Lys Ala Leu Ser Glu Lys Ala
        35                  40                  45

Glu Ser Leu Ala Ser Gly Ala Ala Asn Ala Val Tyr Ser Lys Phe Pro
    50                  55                  60

Tyr Thr Thr Ser Met Thr Gly Ala Asn Tyr Ala Ser Ser Gln Thr Gly
65                  70                  75                  80

Lys Asp Lys Cys Val Arg Asp Ile Gly Tyr Tyr Ile Arg Met Val Thr
                85                  90                  95

Tyr Cys Cys Val Val Gly Gly Thr Gly Pro Met Asp Asp Tyr Leu Val
            100                 105                 110

Ala Gly Ile Ala Glu Ile Asn Arg Thr Phe Asp Leu Ser Pro Ser Trp
        115                 120                 125

Tyr Val Glu Ala Leu Lys Tyr Val Lys Ala Asn His Gly Leu Ser Gly
    130                 135                 140

Asp Ser Ala Val Glu Ala Asn Ser Tyr Ile Asp Tyr Ala Ile Asn Ala
145                 150                 155                 160

Leu Ser
```

<210> SEQ ID NO 36

-continued

```
<211> LENGTH: 162
<212> TYPE: PRT
<213> ORGANISM: Arthrospira platensis

<400> SEQUENCE: 36

Met Lys Thr Pro Leu Thr Glu Ala Val Ser Val Ala Asp Ser Gln Gly
1               5                   10                  15

Arg Phe Leu Ser Ser Thr Glu Ile Gln Val Ala Phe Gly Arg Phe Arg
                20                  25                  30

Gln Ala Lys Ala Gly Leu Glu Ala Ala Lys Ala Leu Thr Ser Lys Ala
            35                  40                  45

Asp Ser Leu Ile Ser Gly Ala Ala Gln Ala Val Tyr Asn Lys Phe Pro
        50                  55                  60

Tyr Thr Thr Gln Met Gln Gly Pro Asn Tyr Ala Ala Asp Gln Arg Gly
65                  70                  75                  80

Lys Asp Lys Cys Ala Arg Asp Ile Gly Tyr Tyr Leu Arg Met Val Thr
                85                  90                  95

Tyr Cys Leu Ile Ala Gly Gly Thr Gly Pro Met Asp Glu Tyr Leu Ile
                100                 105                 110

Ala Gly Ile Asp Glu Ile Asn Arg Thr Phe Glu Leu Ser Pro Ser Trp
            115                 120                 125

Tyr Ile Glu Ala Leu Lys Tyr Ile Lys Ala Asn His Gly Leu Ser Gly
        130                 135                 140

Asp Ala Ala Val Glu Ala Asn Ser Tyr Leu Asp Tyr Ala Ile Asn Ala
145                 150                 155                 160

Leu Ser

<210> SEQ ID NO 37
<211> LENGTH: 172
<212> TYPE: PRT
<213> ORGANISM: Pseudanabaena sp.

<400> SEQUENCE: 37

Met Tyr Asp Ala Phe Ala Lys Val Val Ser Gln Ala Asp Ser Arg Gly
1               5                   10                  15

Ala Tyr Ile Ser Ala Ser Gln Ile Asp Ala Leu Ser Ala Met Val Ala
                20                  25                  30

Asp Gly Ser Lys Arg Leu Asp Ala Val Asn Arg Ile Thr Ser Asn Ser
            35                  40                  45

Ser Ala Ile Val Ala Asn Ala Ala Arg Ala Leu Phe Ala Glu Gln Pro
        50                  55                  60

Ala Leu Ile Ala Pro Gly Gly Asn Ala Tyr Thr Ser Arg Arg Met Ala
65                  70                  75                  80

Ala Cys Leu Arg Asp Met Glu Ile Val Leu Arg Tyr Val Thr Tyr Ala
                85                  90                  95

Ile Tyr Ser Gly Asp Ala Ser Ile Leu Glu Asp Arg Cys Leu Asn Gly
                100                 105                 110

Leu Lys Glu Thr Tyr Leu Ala Leu Gly Thr Pro Gly Ser Ser Val Ala
            115                 120                 125

Val Gly Ile Gly Lys Met Lys Asp Ala Ala Ile Ala Ile Ala Asn Asp
            130                 135                 140

Pro Asn Gly Val Thr Arg Gly Asp Cys Ser Ala Leu Met Ser Glu Ile
145                 150                 155                 160

Gly Ser Tyr Phe Asp Lys Ala Ala Ala Val Ala
                165                 170
```

<210> SEQ ID NO 38
<211> LENGTH: 172
<212> TYPE: PRT
<213> ORGANISM: Arthrospira platensis

<400> SEQUENCE: 38

```
Met Phe Asp Ala Phe Thr Lys Val Val Ser Gln Ala Asp Thr Arg Gly
1               5                   10                  15

Glu Met Leu Ser Thr Ala Gln Ile Asp Ala Leu Ser Gln Met Val Ala
            20                  25                  30

Glu Ser Asn Lys Arg Leu Asp Val Val Asn Arg Ile Thr Ser Asn Ala
        35                  40                  45

Ser Thr Ile Val Ser Asn Ala Ala Arg Ser Leu Phe Ala Glu Gln Pro
    50                  55                  60

Gln Leu Ile Ala Pro Gly Gly Asn Ala Tyr Thr Ser Arg Arg Met Ala
65                  70                  75                  80

Ala Cys Leu Arg Asp Met Glu Ile Ile Leu Arg Tyr Val Thr Tyr Ala
                85                  90                  95

Val Phe Ala Gly Asp Ala Ser Val Leu Glu Asp Arg Cys Leu Asn Gly
            100                 105                 110

Leu Arg Glu Thr Tyr Leu Ala Leu Gly Thr Pro Gly Ser Ser Val Ala
        115                 120                 125

Val Gly Val Gly Lys Met Lys Glu Ala Ala Leu Ala Ile Val Asn Asp
    130                 135                 140

Pro Ala Gly Ile Thr Pro Gly Asp Cys Ser Ala Leu Ala Ser Glu Ile
145                 150                 155                 160

Ala Gly Tyr Phe Asp Arg Ala Ala Ala Val Ser
                165                 170
```

<210> SEQ ID NO 39
<211> LENGTH: 172
<212> TYPE: PRT
<213> ORGANISM: Thermosynechococcus vulcanus

<400> SEQUENCE: 39

```
Met Leu Asp Ala Phe Ala Lys Val Val Ala Gln Ala Asp Ala Arg Gly
1               5                   10                  15

Glu Phe Leu Thr Asn Ala Gln Phe Asp Ala Leu Ser Asn Leu Val Lys
            20                  25                  30

Glu Gly Asn Lys Arg Leu Asp Ala Val Asn Arg Ile Thr Ser Asn Ala
        35                  40                  45

Ser Thr Ile Val Ala Asn Ala Ala Arg Ala Leu Phe Ala Glu Gln Pro
    50                  55                  60

Gln Leu Ile Gln Pro Gly Gly Asn Ala Tyr Thr Asn Arg Arg Met Ala
65                  70                  75                  80

Ala Cys Leu Arg Asp Met Glu Ile Ile Leu Arg Tyr Val Thr Tyr Ala
                85                  90                  95

Ile Leu Ala Gly Asp Ser Ser Val Leu Asp Asp Arg Cys Leu Asn Gly
            100                 105                 110

Leu Arg Glu Thr Tyr Gln Ala Leu Gly Thr Pro Gly Ser Ser Val Ala
        115                 120                 125

Val Ala Ile Gln Lys Met Lys Asp Ala Ala Ile Ala Ile Ala Asn Asp
    130                 135                 140

Pro Asn Gly Ile Thr Pro Gly Asp Cys Ser Ala Leu Met Ser Glu Ile
145                 150                 155                 160
```

Ala Gly Tyr Phe Asp Arg Ala Ala Ala Val Ala
            165                 170

<210> SEQ ID NO 40
<211> LENGTH: 172
<212> TYPE: PRT
<213> ORGANISM: Arthrospira platensis

<400> SEQUENCE: 40

Met Phe Asp Ala Phe Thr Lys Val Val Ser Gln Ala Asp Thr Arg Gly
1               5                   10                  15

Glu Met Leu Ser Thr Ala Gln Ile Asp Ala Leu Ser Gln Met Val Ala
            20                  25                  30

Glu Ser Asn Lys Arg Leu Asp Ser Val Asn Arg Ile Thr Ser Asn Ala
        35                  40                  45

Ser Thr Ile Val Ser Asn Ala Ala Arg Ser Leu Phe Ala Glu Gln Pro
    50                  55                  60

Gln Leu Ile Ala Pro Gly Gly Asn Ala Tyr Thr Ser Arg Arg Met Ala
65                  70                  75                  80

Ala Cys Leu Arg Asp Met Glu Ile Ile Leu Arg Tyr Val Thr Tyr Ala
                85                  90                  95

Val Phe Ala Gly Asp Ala Ser Val Leu Glu Asp Arg Cys Leu Asn Gly
            100                 105                 110

Leu Arg Glu Thr Tyr Leu Ala Leu Gly Thr Pro Gly Ser Ser Val Ala
        115                 120                 125

Val Gly Val Gly Lys Met Lys Glu Ala Ala Leu Ala Ile Val Asn Asp
    130                 135                 140

Pro Ala Gly Ile Thr Pro Gly Asp Cys Ser Ala Leu Ala Ser Glu Ile
145                 150                 155                 160

Ala Gly Tyr Phe Asp Arg Ala Ala Ala Val Ser
            165                 170

<210> SEQ ID NO 41
<211> LENGTH: 162
<212> TYPE: PRT
<213> ORGANISM: Thermosynechococcus vulcanus

<400> SEQUENCE: 41

Met Lys Thr Pro Ile Thr Glu Ala Ile Ala Ala Ala Asp Thr Gln Gly
1               5                   10                  15

Arg Phe Leu Ser Asn Thr Glu Leu Gln Ala Val Asp Gly Arg Phe Lys
            20                  25                  30

Arg Ala Val Ala Ser Met Glu Ala Ala Arg Ala Leu Thr Asn Asn Ala
        35                  40                  45

Gln Ser Leu Ile Asp Gly Ala Gln Ala Val Tyr Gln Lys Phe Pro
    50                  55                  60

Tyr Thr Thr Thr Met Gln Gly Ser Gln Tyr Ala Ser Thr Pro Glu Gly
65                  70                  75                  80

Lys Ala Lys Cys Ala Arg Asp Ile Gly Tyr Tyr Leu Arg Met Ile Thr
                85                  90                  95

Tyr Cys Leu Val Ala Gly Gly Thr Gly Pro Met Asp Glu Tyr Leu Ile
            100                 105                 110

Ala Gly Leu Ser Glu Ile Asn Ser Thr Phe Asp Leu Ser Pro Ser Trp
        115                 120                 125

Tyr Ile Glu Ala Leu Lys Tyr Ile Lys Ala Asn His Gly Leu Thr Gly
    130                 135                 140

```
Gln Ala Ala Val Glu Ala Asn Ala Tyr Ile Asp Tyr Ala Ile Asn Ala
145                 150                 155                 160

Leu Ser

<210> SEQ ID NO 42
<211> LENGTH: 162
<212> TYPE: PRT
<213> ORGANISM: Arthrospira platensis

<400> SEQUENCE: 42

Met Lys Thr Pro Leu Thr Glu Ala Val Ser Ile Ala Asp Ser Gln Gly
1               5                   10                  15

Arg Phe Leu Ser Ser Thr Glu Ile Gln Val Ala Phe Gly Arg Phe Arg
                20                  25                  30

Gln Ala Lys Ala Gly Leu Glu Ala Ala Lys Ala Leu Thr Ser Lys Ala
            35                  40                  45

Asp Ser Leu Ile Ser Gly Ala Ala Gln Ala Val Tyr Asn Lys Phe Pro
50                  55                  60

Tyr Thr Thr Gln Met Gln Gly Pro Asn Tyr Ala Ala Asp Gln Arg Gly
65                  70                  75                  80

Lys Asp Lys Cys Ala Arg Asp Ile Gly Tyr Tyr Leu Arg Met Val Thr
                85                  90                  95

Tyr Cys Leu Ile Ala Gly Gly Thr Gly Pro Met Asp Glu Tyr Leu Ile
            100                 105                 110

Ala Gly Ile Asp Glu Ile Asn Arg Thr Phe Glu Leu Ser Pro Ser Trp
            115                 120                 125

Tyr Ile Glu Ala Leu Lys Tyr Ile Lys Ala Asn His Gly Leu Ser Gly
    130                 135                 140

Asp Ala Ala Val Glu Ala Asn Ser Tyr Leu Asp Tyr Ala Ile Asn Ala
145                 150                 155                 160

Leu Ser
```